(12) United States Patent
Hirschmann et al.

(10) Patent No.: US 9,376,622 B2
(45) Date of Patent: Jun. 28, 2016

(54) LIQUID-CRYSTALLINE MEDIUM

(71) Applicant: Merck Patent GmbH, Darmstadt (DE)

(72) Inventors: Harald Hirschmann, Darmstadt (DE); Andreas Pohle, Pfungstadt (DE); Markus Czanta, Darmstadt (DE); Christian Schoenefeld, Darmstadt (DE); Elvira Montenegro, Wienheim (DE); Volker Reiffenrath, Rossdorf (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/654,069

(22) PCT Filed: Dec. 9, 2013

(86) PCT No.: PCT/EP2013/003713
§ 371 (c)(1),
(2) Date: Jun. 19, 2015

(87) PCT Pub. No.: WO2014/094999
PCT Pub. Date: Jun. 26, 2014

(65) Prior Publication Data
US 2015/0315472 A1    Nov. 5, 2015

(30) Foreign Application Priority Data
Dec. 20, 2012 (DE) .......... 10 2012 024 900

(51) Int. Cl.
| | | |
|---|---|---|
| *G02F 1/1333* | (2006.01) | |
| *C09K 19/34* | (2006.01) | |
| *C09K 19/02* | (2006.01) | |
| *C07D 401/04* | (2006.01) | |
| *C09K 19/04* | (2006.01) | |

(52) U.S. Cl.
CPC .......... *C09K 19/3444* (2013.01); *C07D 401/04* (2013.01); *C09K 19/0208* (2013.01); *C09K 19/3458* (2013.01); *C09K 19/3466* (2013.01); *C09K 2019/0448* (2013.01)

(58) Field of Classification Search
CPC .......... C09K 19/3444; C09K 19/0208; C09K 19/3458; C09K 19/3466; C09K 2019/0448; G02F 1/1333; C07D 401/04

USPC .............. 252/299.01, 299.6, 299.61, 299.63; 428/1.1; 349/182; 544/224, 333
See application file for complete search history.

(56) References Cited

U.S. PATENT DOCUMENTS

| | | | |
|---|---|---|---|
| 4,668,425 A | 5/1987 | Nigorikawa et al. | |
| 5,269,965 A * | 12/1993 | Matsumura .......... | C07D 239/38 252/299.61 |
| 5,453,218 A * | 9/1995 | Wand ..................... | C07C 69/92 252/299.01 |
| 5,919,930 A | 7/1999 | Haber et al. | |
| 6,861,107 B2 | 3/2005 | Klasen-Memmer et al. | |
| 2010/0327226 A1 | 12/2010 | Czanta et al. | |
| 2011/0019119 A1 | 1/2011 | Shu et al. | |

FOREIGN PATENT DOCUMENTS

DE     4030603 A1     4/1992

OTHER PUBLICATIONS

International Search Report dated Feb. 25, 2014 issued in corresponding PCT/EP2013/003713 application (pp. 1-3).
English Translation Abstract of DE 4030603 A1 published Apr. 2, 1992.

\* cited by examiner

*Primary Examiner* — Geraldina Visconti
(74) *Attorney, Agent, or Firm* — Millen White Zeland and Branigan, PC; Csaba Henter; John Sopp

(57) ABSTRACT

The invention relates to compounds of the formula I and to a liquid-crystalline medium which comprises one or more compounds of the formula I,

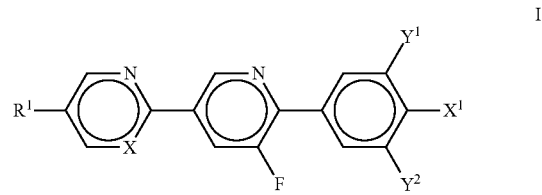

in which $R^1$, $X^1$, X, $Y^1$ and $Y^2$ have the meanings indicated in Claim 1, and to the use thereof for electro-optical purposes, in particular for shutter glasses, 3D applications, in TN, PS-TN, STN, TN-TFT, OCB, IPS, PS-IPS, FFS, PS-FFS and PS-VA-IPS displays.

18 Claims, No Drawings

LIQUID-CRYSTALLINE MEDIUM

The present invention relates to a liquid-crystalline medium (LC medium), to the use thereof for electro-optical purposes, and to LC displays containing this medium.

Liquid crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (superbirefringence effect) cells and OMI (optical mode interference) cells. The commonest display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapour pressure are desired.

Matrix liquid-crystal displays of this type are known. Examples of non-linear elements which can be used to individually switch the individual pixels are active elements (i.e. transistors). The term "active matrix" is then used, where a distinction can be made between two types:
1. MOS (metal oxide semiconductor) or other diodes on silicon wafers as substrate.
2. Thin-film transistors (TFTs) on a glass plate as substrate.

The use of single-crystal silicon as substrate material restricts the display size, since even modular assembly of various part-displays results in problems at the joints.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is opposite each switchable pixel.

The TFT displays usually operate as TN cells with crossed polarisers in transmission and are backlit.

The term MLC displays here encompasses any matrix display with integrated non-linear elements, i.e., besides the active matrix, also displays with passive elements, such as varistors or diodes (MIM=metal-insulator-metal).

MLC displays of this type are particularly suitable for TV applications (for example pocket televisions) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, pp. 141 ff, Paris; STROMER, M., Proc. Eurodisplay 84, September 1984: Design of Thin Film Transistors for Matrix Addressing of Television Liquid Crystal Displays, pp. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable lifetimes. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not satisfy today's requirements.

Besides liquid-crystal displays which use backlighting, i.e. are operated transmissively and if desired transflectively, reflective liquid-crystal displays are also particularly interesting. These reflective liquid-crystal displays use the ambient light for information display. They thus consume significantly less energy than backlit liquid-crystal displays having a corresponding size and resolution. Since the TN effect is characterised by very good contrast, reflective displays of this type can even be read well in bright ambient conditions. This is already known of simple reflective TN displays, as used, for example, in watches and pocket calculators. However, the principle can also be applied to high-quality, higher-resolution active matrix-addressed displays, such as, for example, TFT displays. Here, as already in the transmissive TFT-TN displays which are generally conventional, the use of liquid crystals of low birefringence ($\Delta n$) is necessary in order to achieve low optical retardation ($d \cdot \Delta n$). This low optical retardation results in usually acceptable low viewing-angle dependence of the contrast (cf. DE 30 22 818). In reflective displays, the use of liquid crystals of low birefringence is even more important than in transmissive displays since the effective layer thickness through which the light passes is approximately twice as large in reflective displays as in transmissive displays having the same layer thickness.

In order to achieve 3D effects by means of shutter glasses, fast-switching mixtures having low rotational viscosities and correspondingly high optical anisotropy ($\Delta n$), in particular, are employed. Electro-optical lens systems, by means of which a 2-dimensional representation of a display can be switched to a 3-dimensional autostereoscopic representation, can be achieved using mixtures having high optical anisotropy (Δn).

Thus, there continues to be a great demand for MLC displays having very high specific resistance at the same time as a large working-temperature range, short response times, even at low temperatures, and a low threshold voltage which do not exhibit these disadvantages or only do so to a lesser extent.

In the case of TN (Schadt-Helfrich) cells, media are desired which facilitate the following advantages in the cells:
- extended nematic phase range (in particular down to low temperatures)
- switchability at extremely low temperatures (outdoor use, automobiles, avionics)
- increased resistance to UV radiation (longer life)
- low threshold voltage.

The media available from the prior art do not enable these advantages to be achieved while simultaneously retaining the other parameters.

In the case of supertwisted (STN) cells, media are desired which facilitate greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

In particular in the case of LC displays for TV and video applications (for example LCD-TVs, monitors, PDAs, notebooks, games consoles), a significant reduction in the response times is desired. This requires LC mixtures having low rotational viscosities and high values for the birefringence Δn.

The invention has the object of providing media, in particular for MLC, FFS, IPS, TN, positive VA or STN displays of this type, which do not exhibit the disadvantages indicated above or only do so to a lesser extent and preferably have fast response times and low rotational viscosities at the same time as a high clearing point, as well as high dielectric anisotropy and a low threshold voltage.

It has now been found that this object can be achieved if LC media comprising one or more compounds of the formula I are used. The compounds of the formula I result in LC mixtures having the desired properties indicated above.

The invention relates to a liquid-crystalline medium, characterised in that it comprises one or more compounds of the formula I

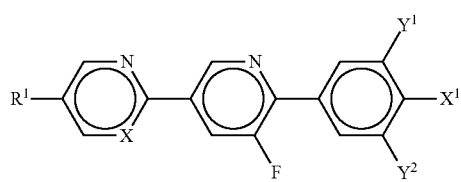

I in which
R$^1$ denotes a halogenated or unsubstituted alkyl or alkoxy radical having 1 to 15 C atoms, where, in addition, one or more CH$_2$ groups in these radicals may each be replaced, independently of one another, by —C≡C—, —CF$_2$O—, —CH=CH—,

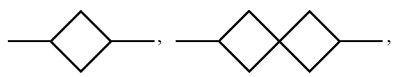

—O—, —CO—O— or —O—CO— in such a way that O atoms are not linked directly to one another,
X$^1$ denotes F, Cl, CN, SF$_5$, SCN, NCS, a halogenated alkyl radical, a halogenated alkenyl radical, a halogenated alkoxy radical or a halogenated alkenyloxy radical, each having up to 6 C atoms, and
X denotes C—H or N, and
Y$^1$ and Y$^2$ each, independently of one another, denote H or F.

Surprisingly, it has been found that mixtures comprising one or more compounds of the formulae I have high dielectric anisotropy Δε and at the same time have an advantageous rotational viscosity γ$_1$/clearing point ratio. They are therefore particularly suitable for achieving liquid-crystal mixtures having low γ$_1$ and high Δn values. In addition, the compounds of the formula I exhibit good solubility in LC media. LC media according to the invention comprising one or more compounds of the formula I have a low rotational viscosity, fast response times, very high positive dielectric anisotropy, high birefringence and a broad nematic phase range. They are therefore particularly suitable for lenses, 2D/3D applications, mobile telephones, TV and video applications.

The compounds of the formula I have a broad range of applications. Depending on the choice of substituents, they can serve as base materials of which liquid-crystalline media are predominantly composed; however, liquid-crystalline base materials from other classes of compound can also be added to the compounds of the formula I in order, for example, to modify the dielectric and/or optical anisotropy of a dielectric of this type and/or to optimise its threshold voltage and/or its viscosity.

In the pure state, the compounds of the formula I are colourless and form liquid-crystalline mesophases in a temperature range which is favourably located for electro-optical use. They are stable chemically, thermally and to light.

If R$^1$ in the formulae above and below denotes an alkyl radical and/or an alkoxy radical, this may be straight-chain or branched. It is preferably straight-chain, has 2, 3, 4, 5, 6 or 7 C atoms and accordingly preferably denotes ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If R$^1$ denotes an alkyl radical in which one CH$_2$ group has been replaced by —CH=CH—, this may be straight-chain or branched. It is preferably straight-chain and has 2 to 10 C atoms. Accordingly, it denotes, in particular, vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, dec-1-, -2-, -3-, -4-, -5-, -6-, -7-, -8- or -9-enyl.

If R$^1$ denotes an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

$R^1$ preferably denotes straight-chain alkyl having 1 to 6 C atoms, in particular ethyl, propyl and pentyl, furthermore alkenyl having 2 to 6 C atoms.

In the formulae above and below, $X^1$ is preferably F, Cl or a mono- or polyfluorinated alkyl or alkoxy radical having 1, 2 or 3 C atoms or a mono- or polyfluorinated alkenyl radical having 2 or 3 C atoms. $X^1$ is particularly preferably F, Cl, $CF_3$, $CHF_2$, $OCF_3$, $OCHF_2$, $OCFHCF_3$, $OCFHCHF_2$, $OCFHCHF_2$, $OCF_2CH_3$, $OCF_2CHF_2$, $OCF_2CHF_2$, $OCF_2CF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$, $OCH=CF_2$ or $CH=CF_2$, very particularly preferably F or $OCF_3$, furthermore $CF_3$, $OCF=CF_2$, $OCHF_2$ or $OCH=CF_2$.

Particular preference is given to compounds of the formula I in which $X^1$ denotes F or $OCF_3$, preferably F. Preferred compounds of the formula I are those in which $Y^1$ and/or $Y^2$ each denote H.

Very particularly preferred compounds of the formula I are mentioned below:

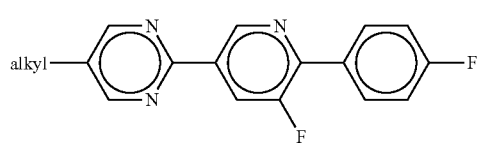

I-1

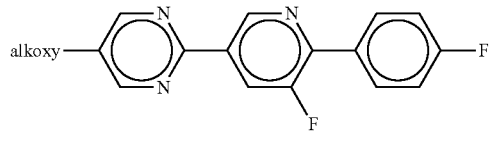

I-2

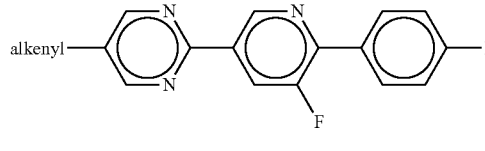

I-3

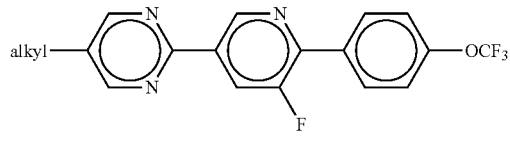

I-4

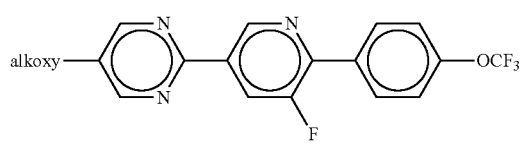

I-5

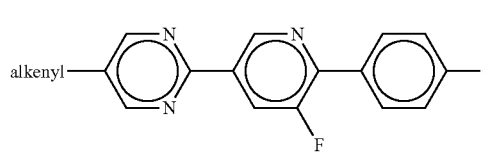

I-6

-continued

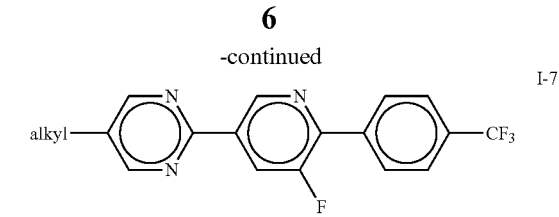

I-7

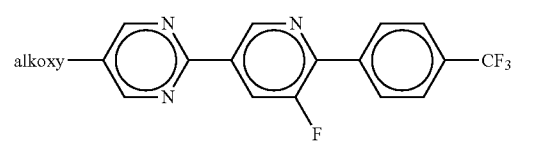

I-8

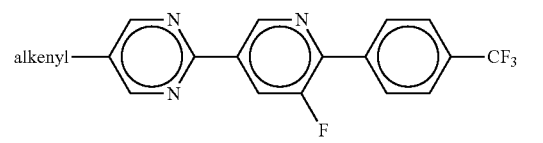

I-9

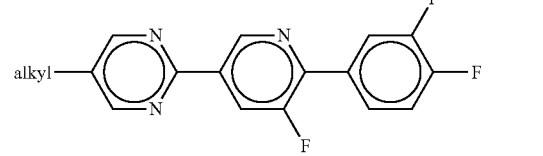

I-10

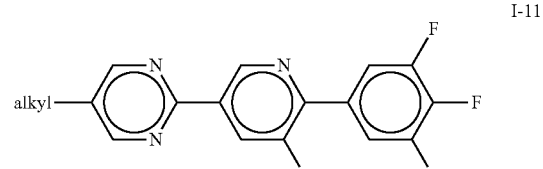

I-11

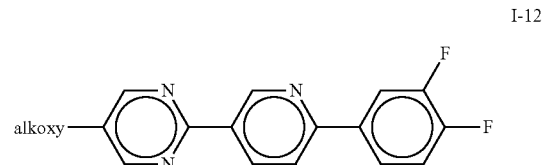

I-12

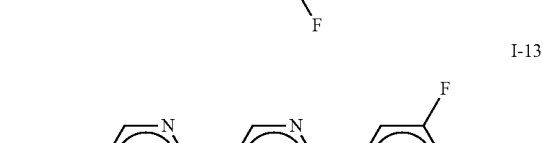

I-13

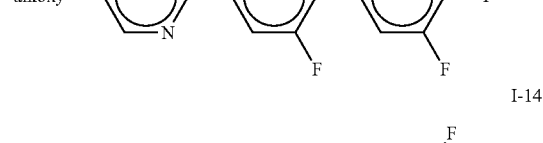

I-14

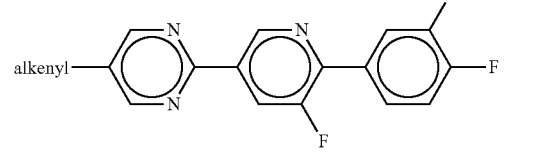

I-15

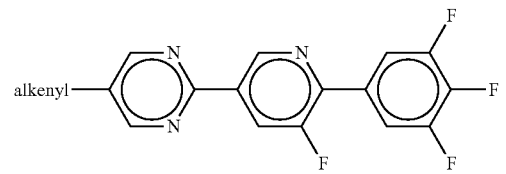

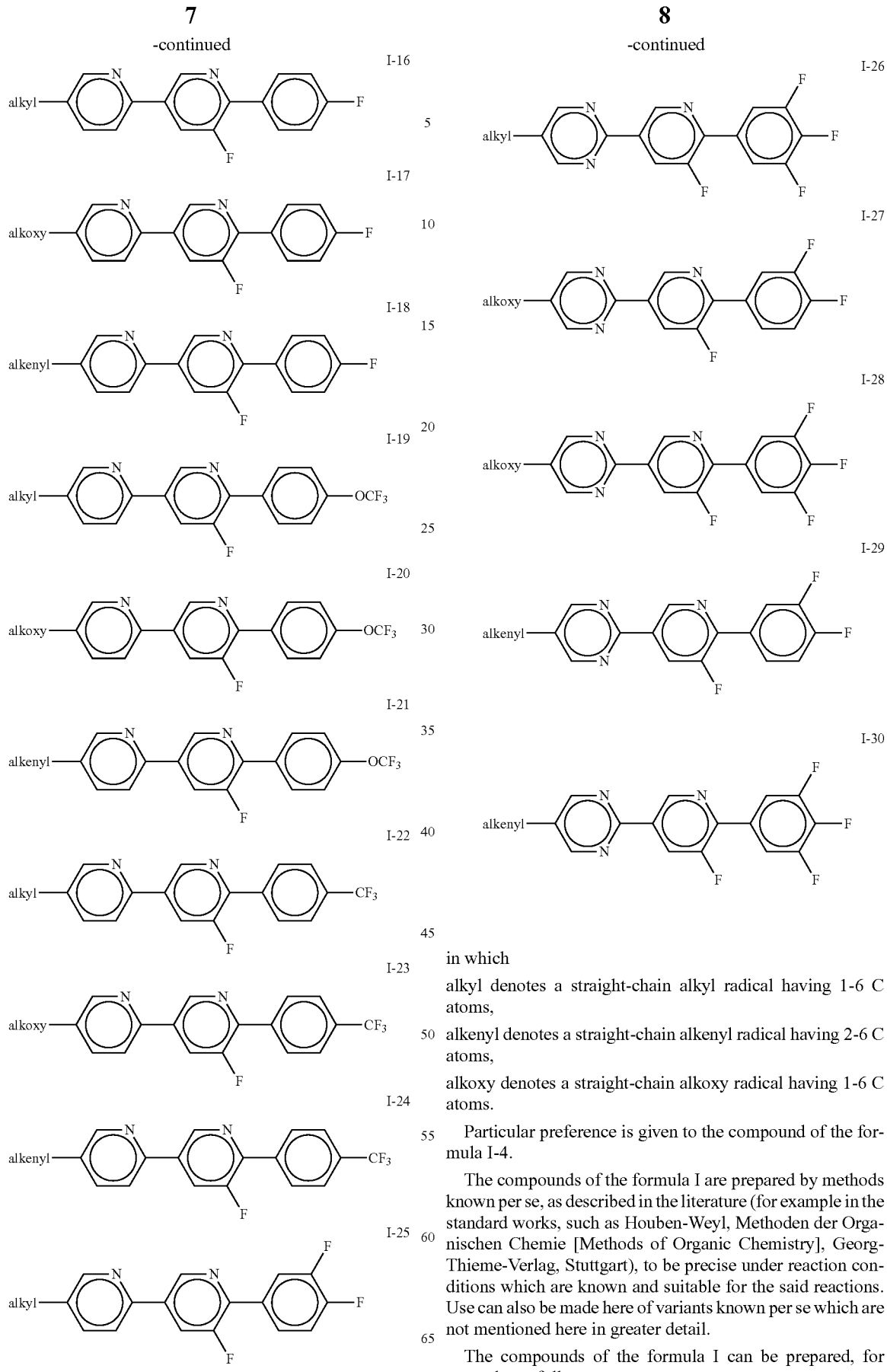

in which alkyl denotes a straight-chain alkyl radical having 1-6 C atoms, alkenyl denotes a straight-chain alkenyl radical having 2-6 C atoms, alkoxy denotes a straight-chain alkoxy radical having 1-6 C atoms.

Particular preference is given to the compound of the formula I-4.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The compounds of the formula I can be prepared, for example, as follows:

Scheme 1
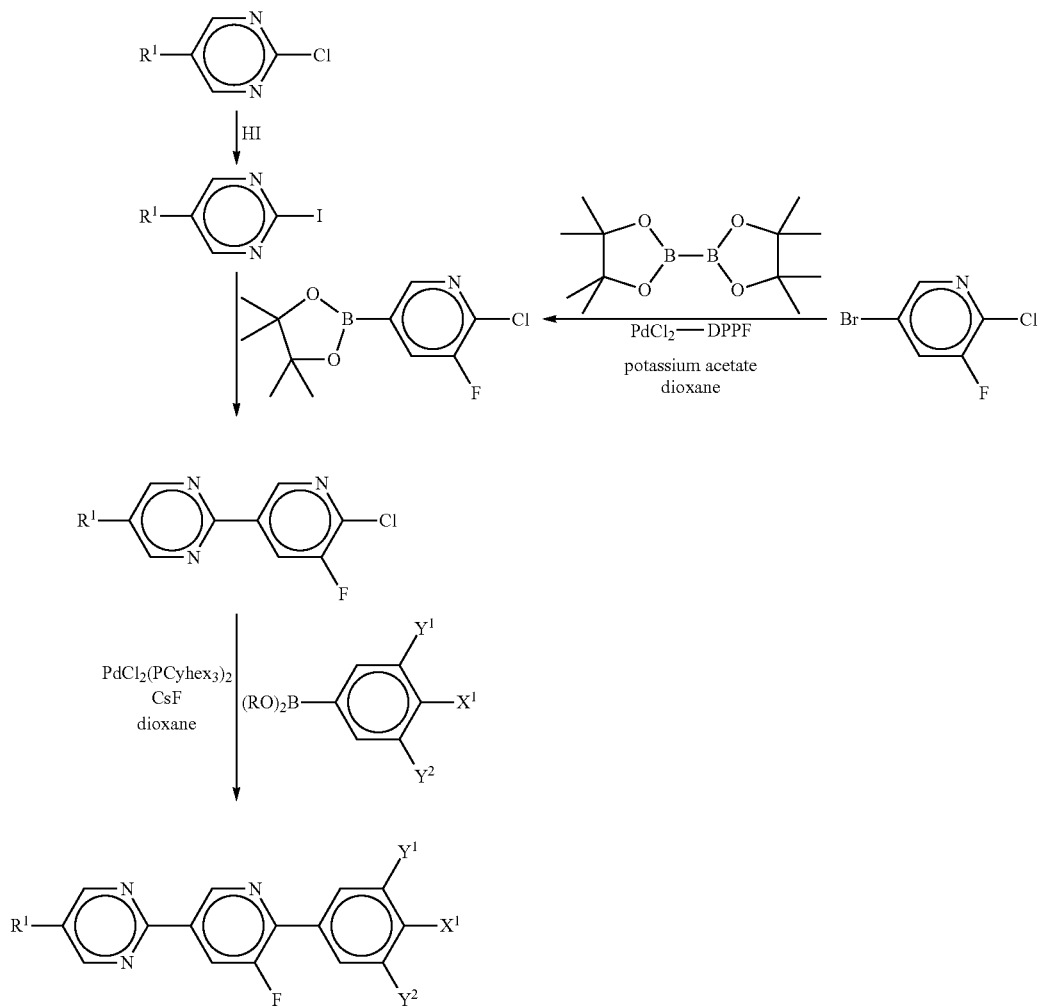
Particularly preferred compounds of the formula I are prepared as follows:
Scheme 2
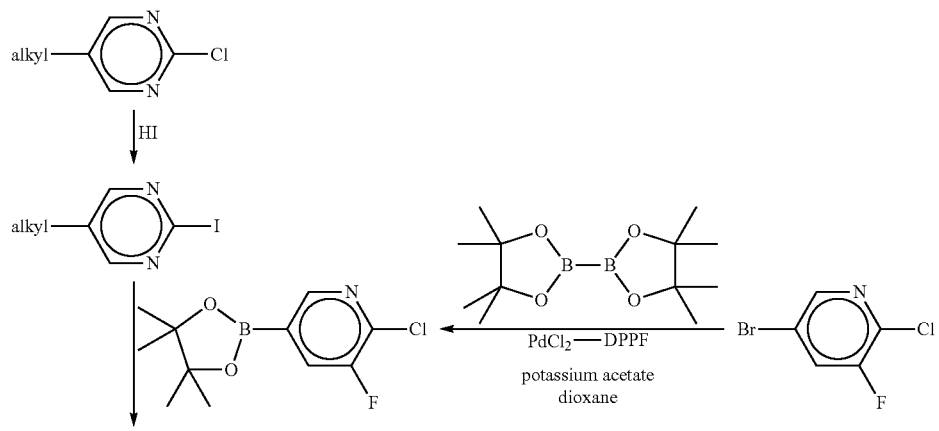

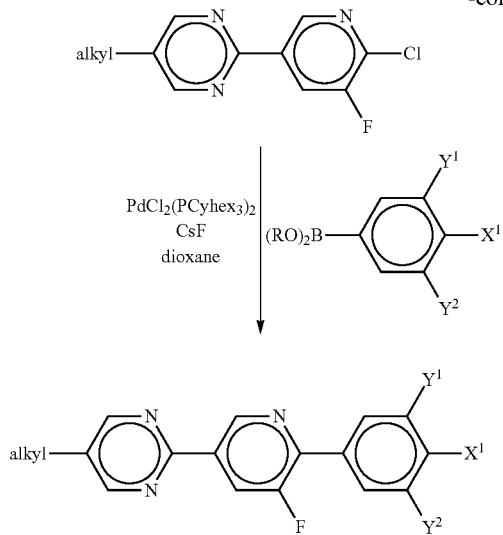
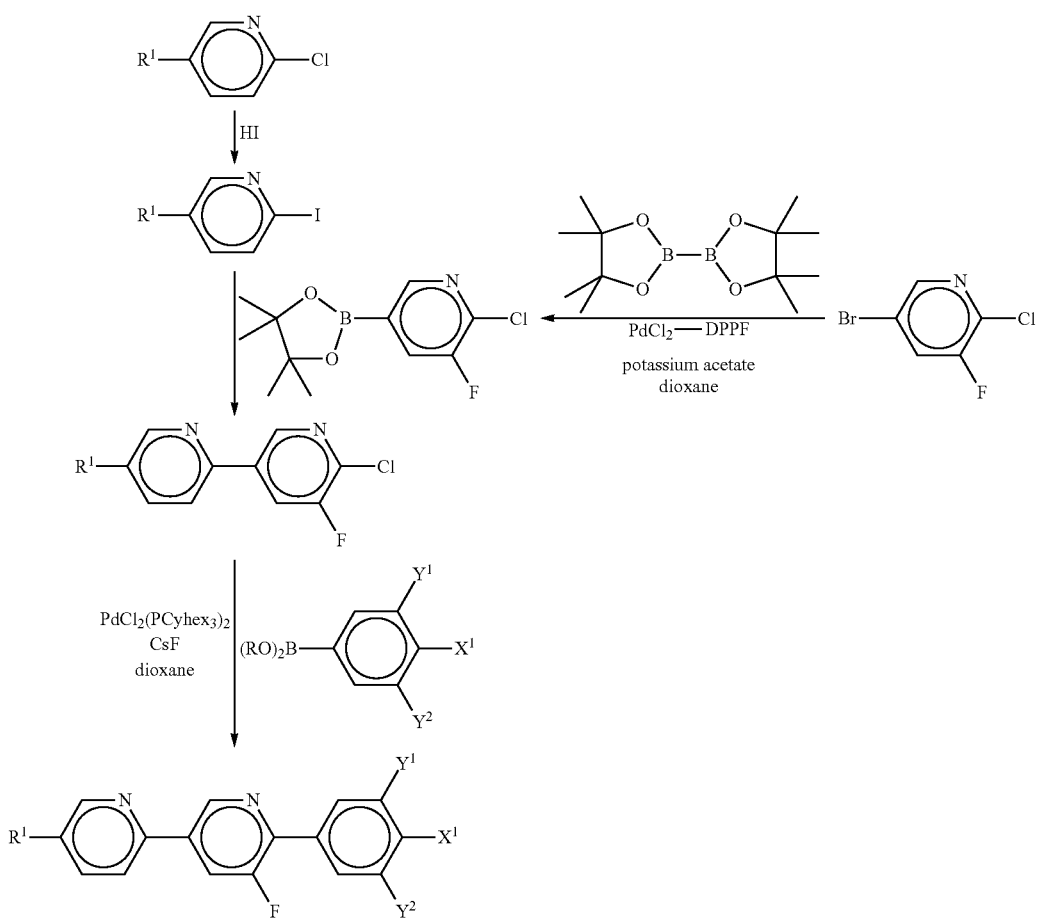
Further preferred embodiments are indicated below:
The medium additionally comprises one or more compounds of the formulae II and/or III

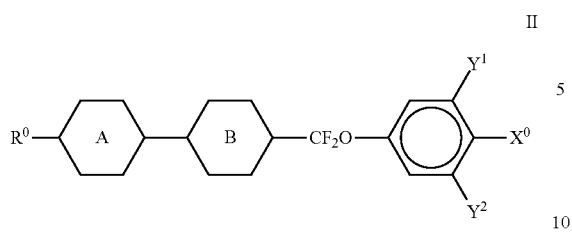

II

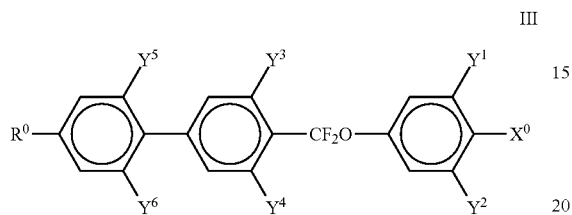

III in which

R⁰ denotes a halogenated or unsubstituted alkyl or alkoxy radical having 1 to 15 C atoms, where, in addition, one or more CH$_2$ groups in these radicals may each be replaced, independently of one another, by —C≡C—, —CF$_2$O—, —CH=CH—,

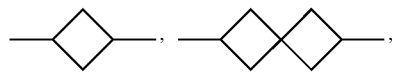

—O—, —CO—O— or —O—CO— in such a way that O atoms are not linked directly to one another, X⁰ denotes F, Cl, CN, SF$_5$, SCN, NCS, a halogenated alkyl radical, a halogenated alkenyl radical, a halogenated alkoxy radical or a halogenated alkenyloxy radical having up to 6 C atoms, and Y$^{1-6}$ each, independently of one another, denote H or F,

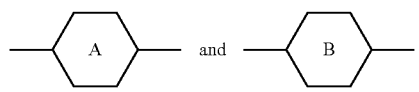

each, independently of one another, denote

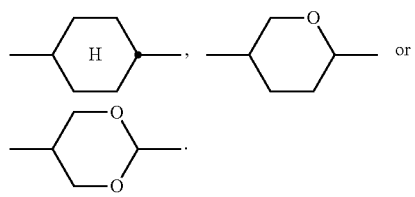

The compounds of the formula II are preferably selected from the following formulae:

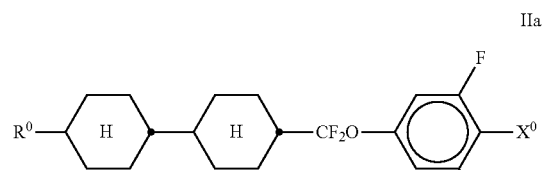

IIa

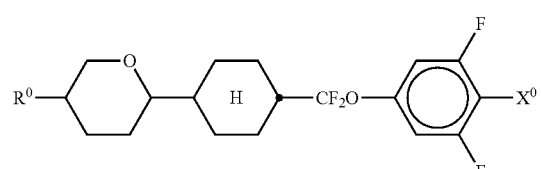

IIb

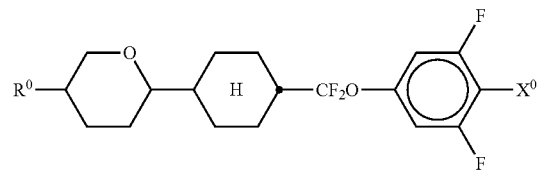

IIc

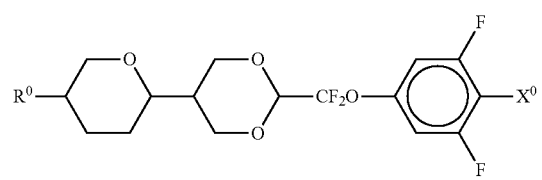

IId

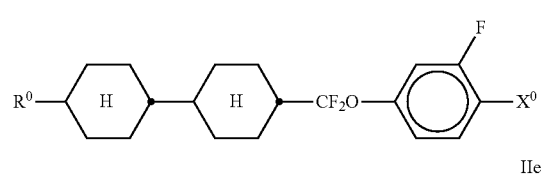

IIe

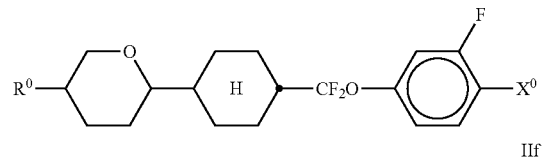

IIf

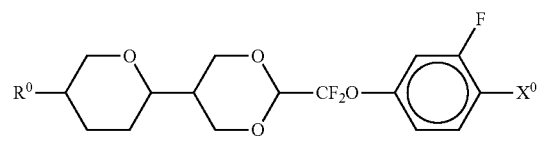

in which R⁰ and X⁰ have the meanings indicated above.

R⁰ preferably denotes alkyl having 1 to 6 C atoms. X⁰ preferably denotes F, furthermore OCF$_3$ and CF$_3$. Particular preference is given to compounds of the formulae IIa and IIb, in particular compounds of the formulae IIa and IIb in which X⁰ denotes F.

The compounds of the formula III are preferably selected from the following formulae:

IIIa

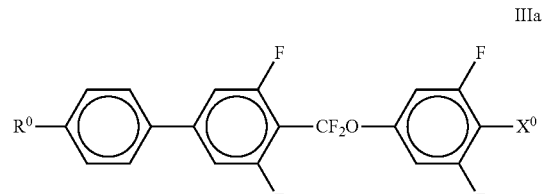

-continued

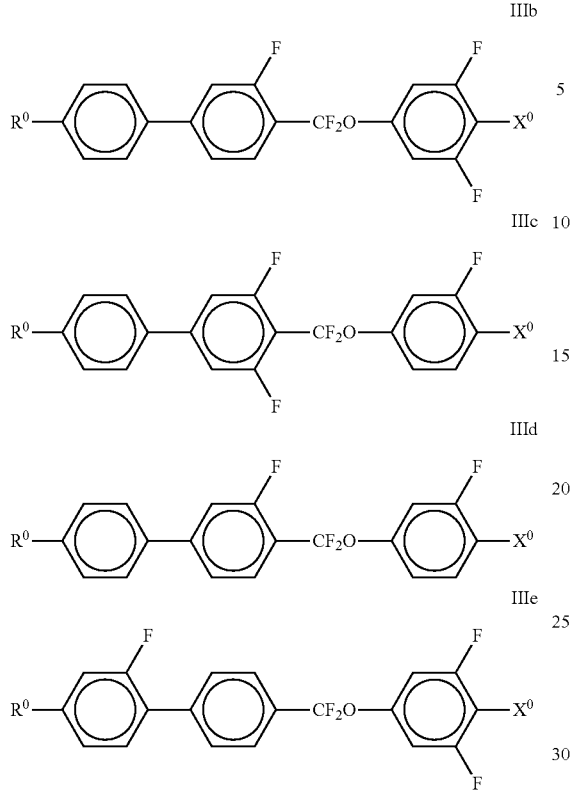

in which R⁰ and X⁰ have the meanings indicated above.

R⁰ preferably denotes alkyl having 1 to 6 C atoms. X⁰ preferably denotes F, furthermore OCF$_3$ and CF$_3$. Particular preference is given to compounds of the formulae IIIa and IIIe, in particular compounds of the formula IIIa;

The medium additionally comprises one or more compounds selected from the following formulae:

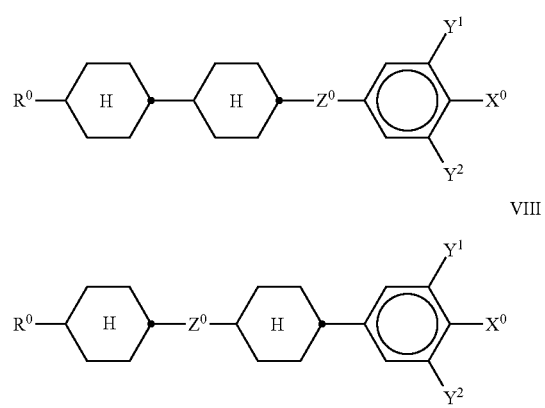

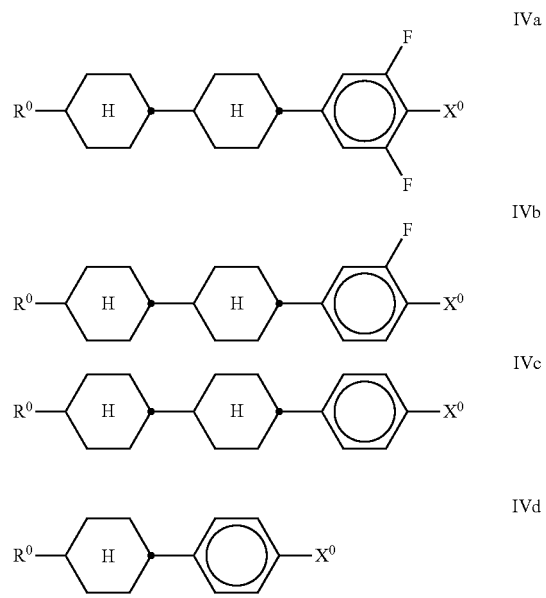

in which

R⁰, X⁰ and Y$^{1-4}$ have the meanings indicated above, and

Z⁰ denotes —C$_2$H$_4$—, —(CH$_2$)$_4$—, —CH=CH—, —CF=CF—, —C$_2$F$_4$—, —CH$_2$CF$_2$—, —CF$_2$CH$_2$—, —CH$_2$O—, —OCH$_2$—, —COO—, —CF$_2$O— or —OCF$_2$—, in formulae V and VI also a single bond, r denotes 0 or 1, and s denotes 0 or 1;

The compounds of the formula IV are preferably selected from the following formulae:

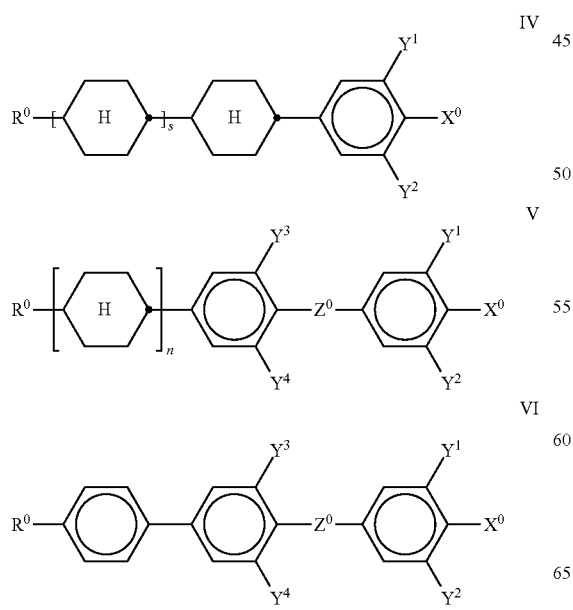

in which R⁰ and X⁰ have the meanings indicated above.

R⁰ preferably denotes alkyl having 1 to 6 C atoms. X⁰ preferably denotes F or OCF$_3$, furthermore CF$_3$, OCF=CF$_2$ or Cl;

The compounds of the formula V are preferably selected from the following formulae:

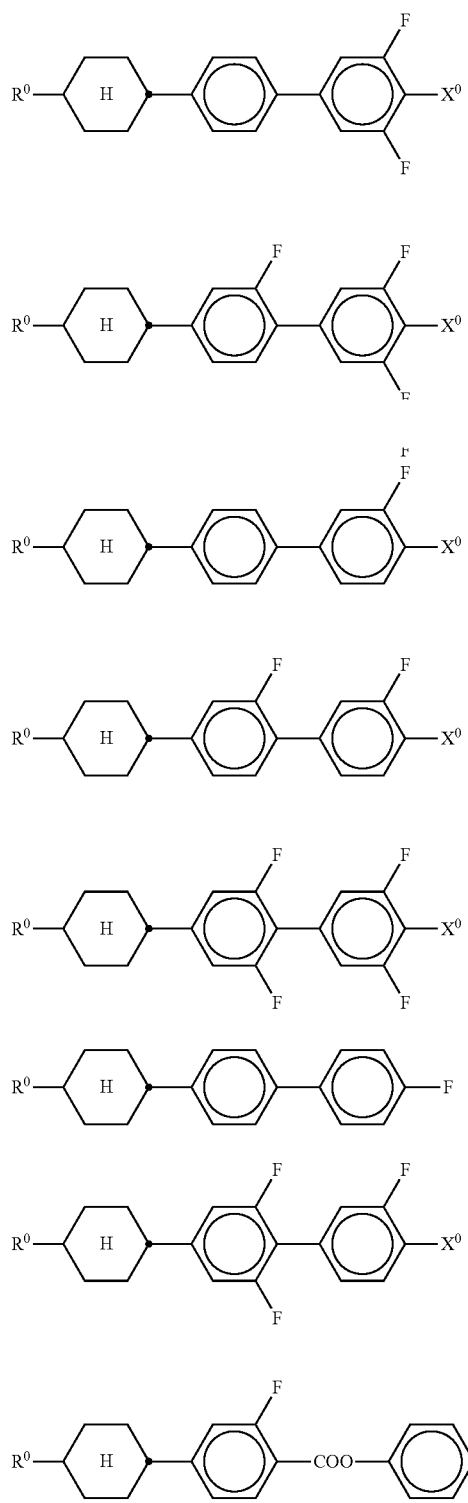

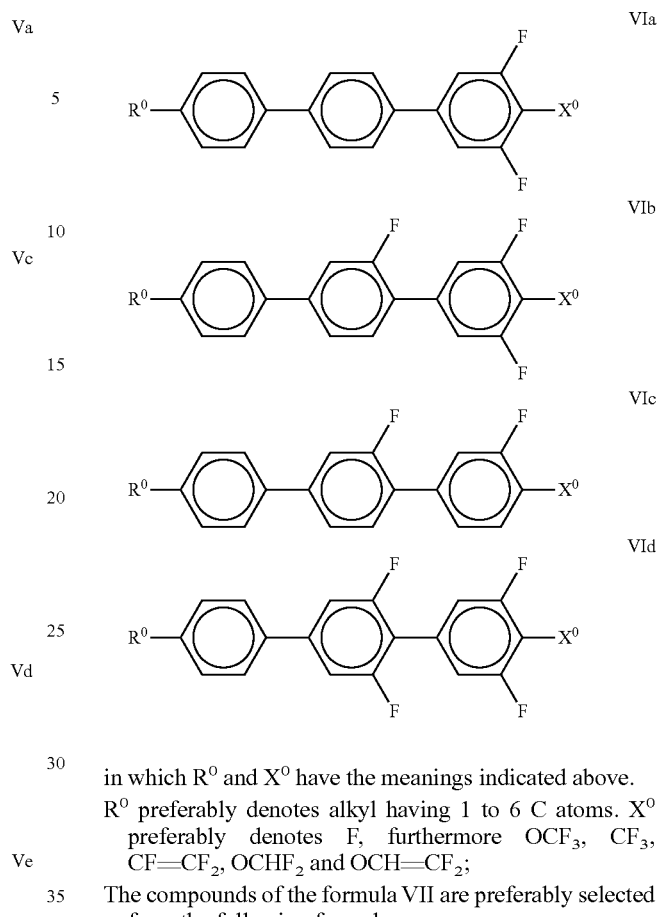

in which R⁰ and X⁰ have the meanings indicated above.

R⁰ preferably denotes alkyl having 1 to 6 C atoms. X⁰ preferably denotes F, furthermore OCF$_3$, CF$_3$, CF=CF$_2$, OCHF$_2$ and OCH=CF$_2$;

The compounds of the formula VII are preferably selected from the following formulae:

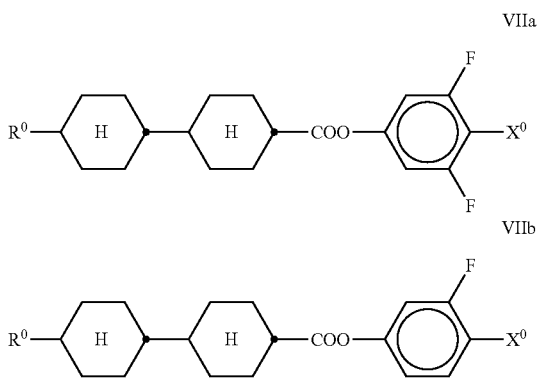

in which R⁰ and X⁰ have the meanings indicated above.

R⁰ preferably denotes alkyl having 1 to 6 C atoms. X⁰ preferably denotes F, furthermore OCF$_3$, OCHF$_2$ and OCH=CF$_2$.

The medium additionally comprises one or more compounds selected from the following formulae:

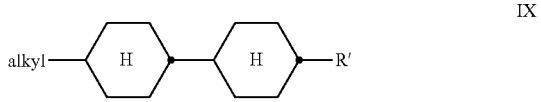

in which R⁰ and X⁰ have the meanings indicated above.

R⁰ preferably denotes alkyl having 1 to 6 C atoms. X⁰ preferably denotes F and OCF$_3$, furthermore OCHF$_2$, CF$_3$, OCF=CF$_2$ and OCH=CF$_2$;

The compounds of the formula VI are preferably selected from the following formulae:

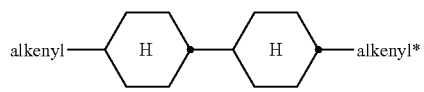
X

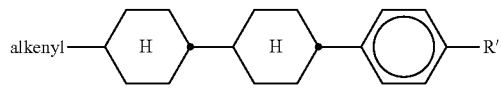
XI

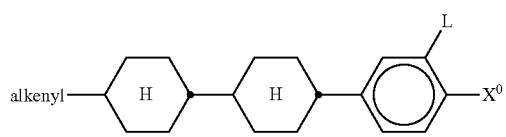
XII in which X⁰ has the meanings indicated above, and
L denotes H or F,
"alkyl" denotes $C_{1-6}$-alkyl,
R' denotes $C_{1-6}$-alkyl, $C_{1-6}$-alkoxy or $C_{2-6}$-alkenyl, and
"alkenyl" and "alkenyl*" each, independently of one another, denote $C_{2-6}$-alkenyl.

The compounds of the formulae IX-XII are preferably selected from the following formulae:

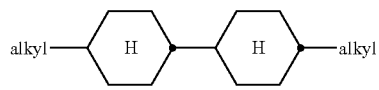
IXa

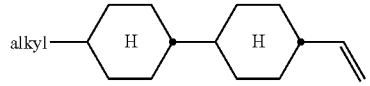
IXb

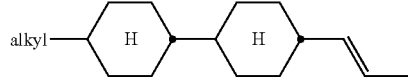
IXc

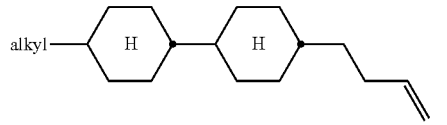
IXd

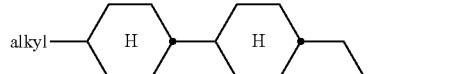
IXe

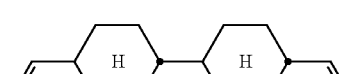
Xa

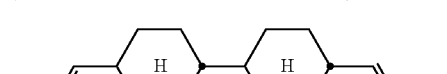
Xb

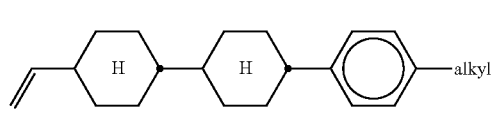
XIa

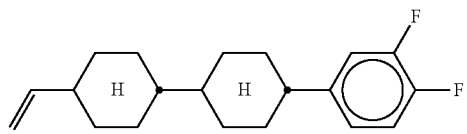
XIIa in which "alkyl" has the meaning indicated above.

Particular preference is given to the compounds of the formulae IXa, IXb, IXc, Xa, Xb, XIa and XIIa. In the formulae IXb and IX, "alkyl" preferably, independently of one another, denotes n-$C_3H_7$, n-$C_4H_9$ or n-$C_5H_{11}$, in particular n-$C_3H_7$.

The medium additionally comprises one or more compounds selected from the following formulae:

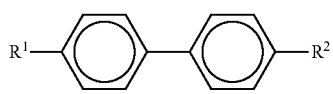
XIII

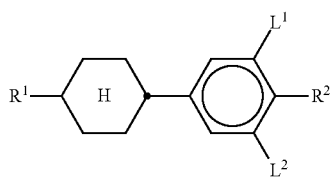
XIV in which $L^1$ and $L^2$ have the meanings indicated above, and $R^1$ and $R^2$ each, independently of one another, denote n-alkyl, alkoxy, oxaalkyl, fluoroalkyl or alkenyl, each having up to 6 C atoms, and preferably each, independently of one another, denote alkyl having 1 to 6 C atoms; in the compound of the formula XIII, at least one of the radicals $R^1$ and $R^2$ preferably denotes alkenyl having 2 to 6 C atoms.

The medium comprises one or more compounds of the formula XIII in which at least one of the radicals $R^1$ and $R^2$ denotes alkenyl having 2 to 6 C atoms, preferably those selected from the following formulae:

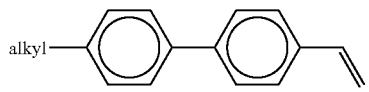
XIIIa

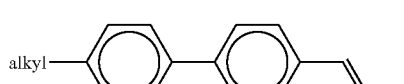
XIIIb

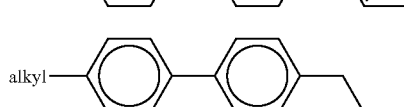
XIIIc

XIIId in which "alkyl" has the meaning indicated above;
The medium comprises one or more compounds of the formula XIIIe,

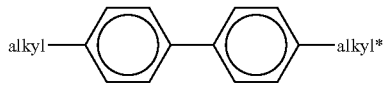 XIIIe in which "alkyl" and "alkyl*" have the meanings indicated above;

The medium comprises one or more compounds of the following formulae:

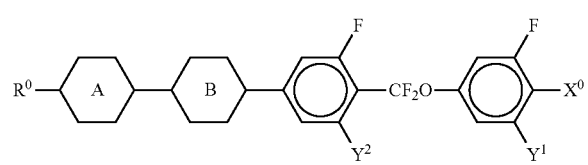 XV

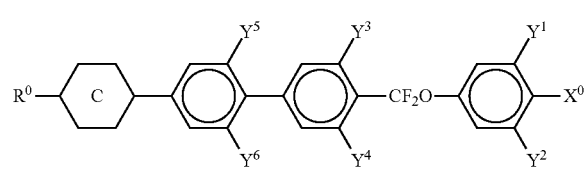 XVI in which $R^0$, $X^0$ and $Y^{1-4}$ have the meanings indicated in formula I, and

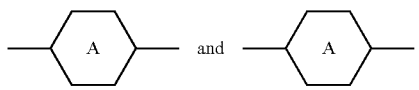

each, independently of one another, denote

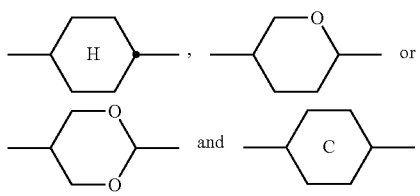

denotes

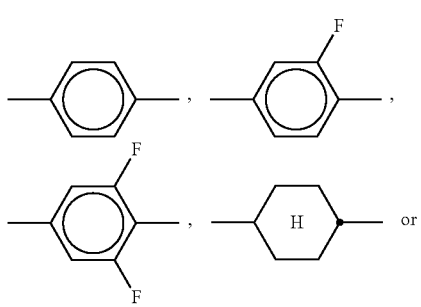

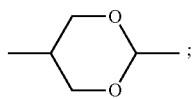

The compounds of the formulae XV and XVI are preferably selected from the following formulae:

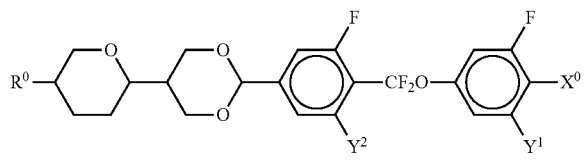 XVa

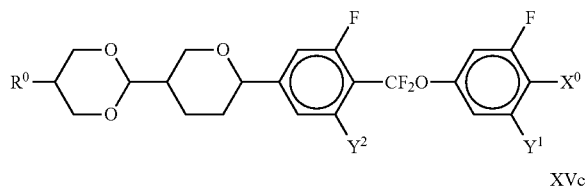 XVb

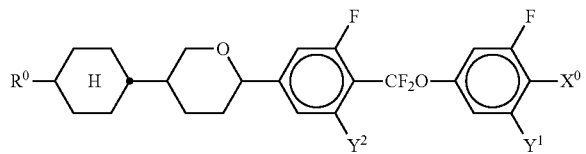 XVc

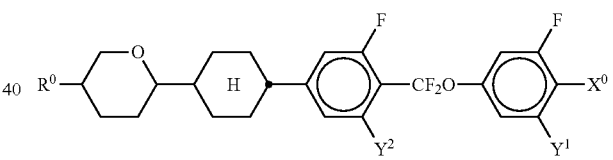 XVd

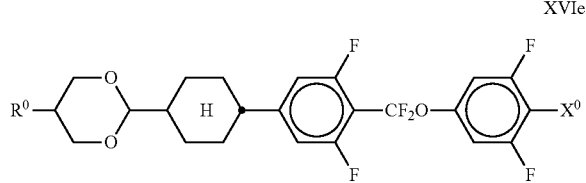 XVIe

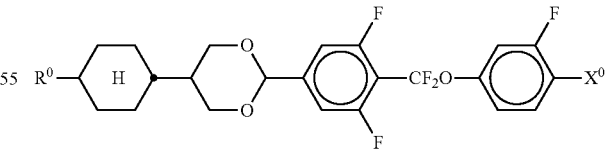 XVIf

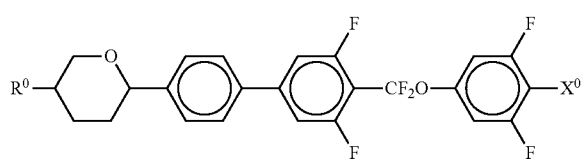 XVIa

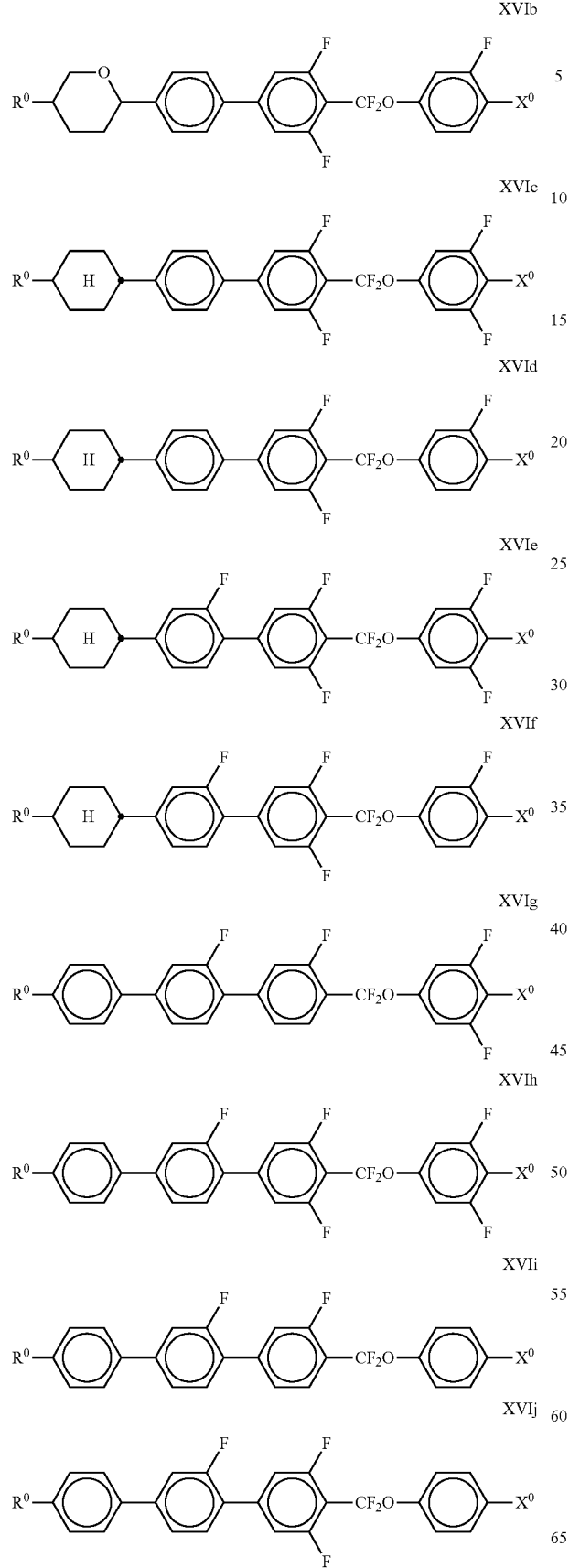

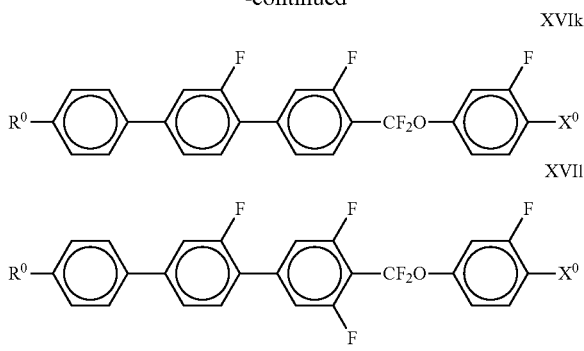

in which $R^0$ and $X^0$ have the meanings indicated above.

$R^0$ preferably denotes alkyl having 1 to 6 C atoms. $X^0$ preferably denotes F, furthermore $OCF_3$. Particularly preferred compounds of the formulae XV and XVa-XVf are those in which $Y^1$ denotes F and $Y^2$ denotes H or F, preferably F. The mixture according to the invention particularly preferably comprises at least one compound of the formula XVf.

The medium comprises one or more compounds of the formula XVII,

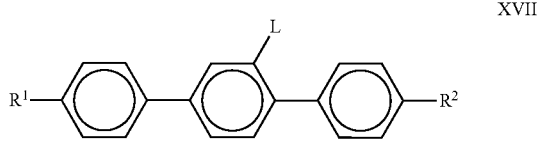

in which $R^1$ and $R^2$ have the meanings indicated above and preferably each, independently of one another, denote alkyl having 1 to 6 C atoms. L denotes H or F.

Particularly preferred compounds of the formula XVII are those of the sub-formulae

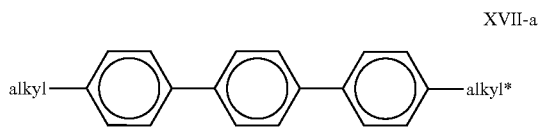

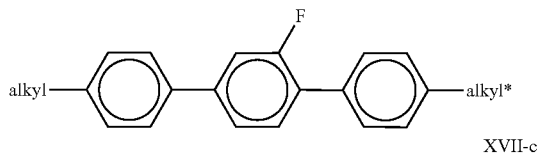

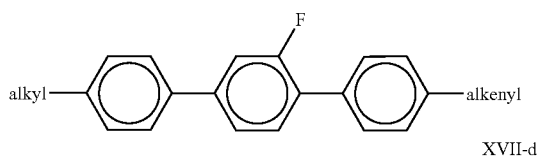

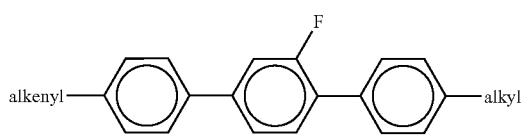

XVII-e

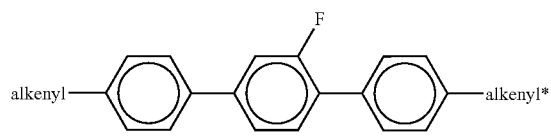

XVII-f

in which
- alkyl and alkyl* each, independently of one another, denote a straight-chain alkyl radical having 1-6 C atoms, in particular ethyl, propyl and pentyl,
- alkenyl and alkenyl* each, independently of one another, denote a straight-chain alkenyl radical having 2-6 C atoms, in particular $CH_2=CHC_2H_4$, $CH_3CH=CHC_2H_4$, $CH_2=CH$ and $CH_3CH=CH$.

Particular preference is given to the compounds of the formulae XVII-b and XVII-c. Very particular preference is given to the compounds of the formulae

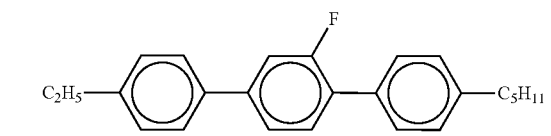

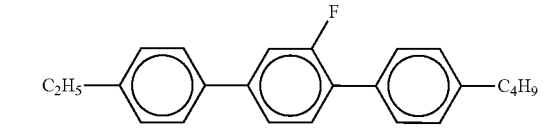

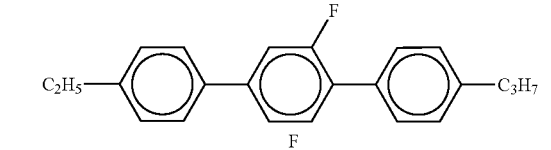

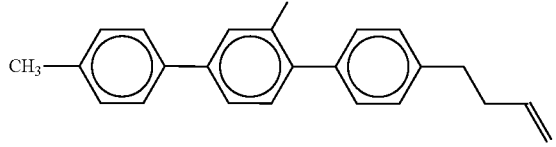

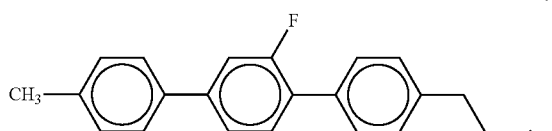

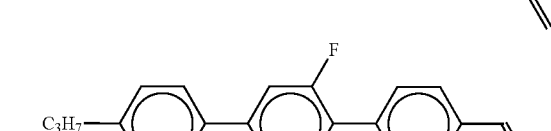

The medium additionally comprises one or more compounds of the following formulae:

XVIIIa

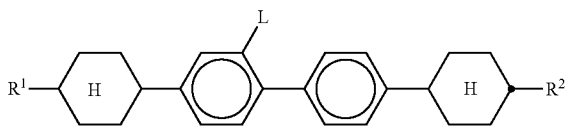

xviiib

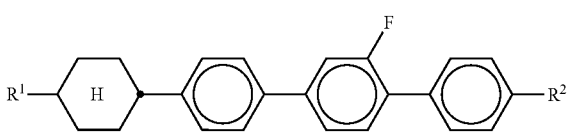

in which $R^1$ and $R^2$ have the meanings indicated above and preferably each, independently of one another, denote alkyl having 1 to 6 C atoms. L denotes H or F;

The medium additionally comprises one or more compounds selected from the following formulae:

XIX

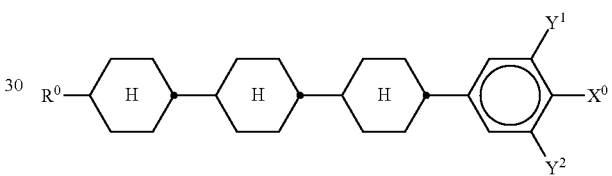

XX

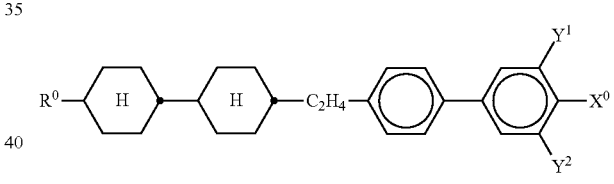

XXI

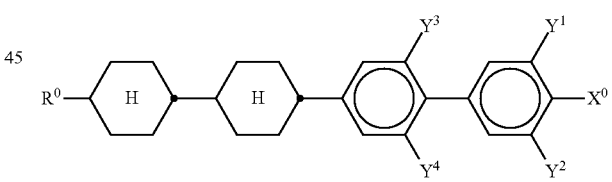

XXII

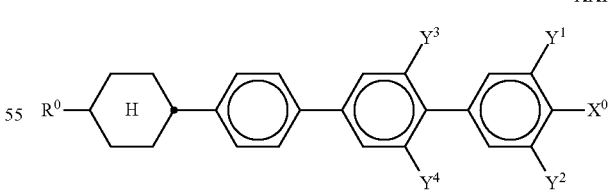

XXIII

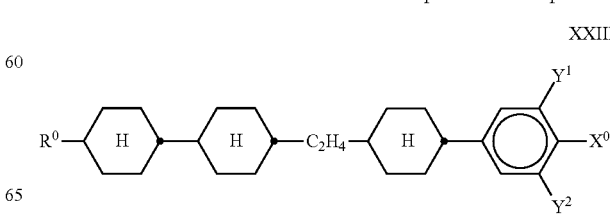

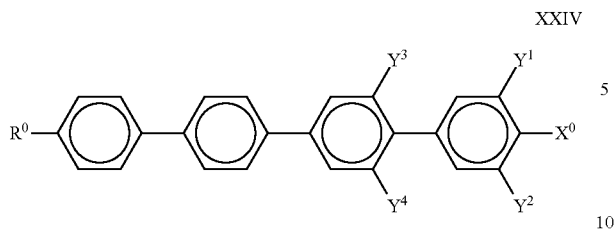
XXIV in which $R^0$ and $X^0$ each, independently of one another, have one of the meanings indicated above, and $Y^{1-4}$ each, independently of one another, denote H or F. $X^0$ is preferably F, Cl, $CF_3$, $OCF_3$ or $OCHF_2$. $R^0$ preferably denotes alkyl, alkoxy, oxaalkyl, fluoroalkyl or alkenyl, each having up to 6 C atoms.

The mixture according to the invention particularly preferably comprises one or more compounds of the formula XXIV-a,

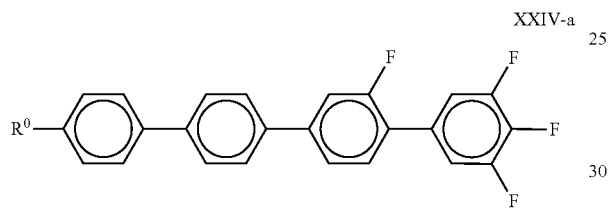
XXIV-a in which $R^0$ has the meanings indicated above. $R^0$ preferably denotes straight-chain alkyl, in particular ethyl, n-propyl, n-butyl and n-pentyl and very particularly preferably n-propyl. The compound(s) of the formula XXIV, in particular of the formula XXIV-a, is (are) preferably employed in the mixtures according to the invention in amounts of 0.5-20% by weight, particularly preferably 1-15% by weight.

The medium additionally comprises one or more compounds of the formula XXIV,

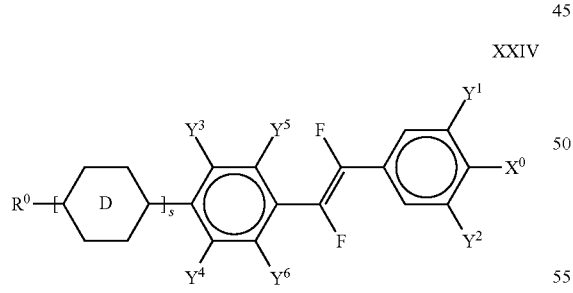
XXIV in which $R^0$, $X^0$ and $Y^{1-6}$ have the meanings indicated in formula I, s denotes 0 or 1, and

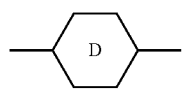

denotes

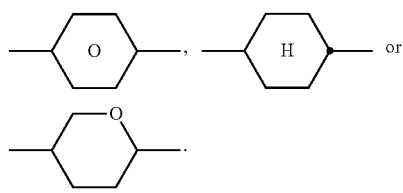

In the formula XXIV, $X^0$ may also denote an alkyl radical having 1-6 C atoms or an alkoxy radical having 1-6 C atoms. The alkyl or alkoxy radical is preferably straight-chain.

$R^0$ preferably denotes alkyl having 1 to 6 C atoms. $X^0$ preferably denotes F;

The compounds of the formula XXIV are preferably selected from the following formulae:

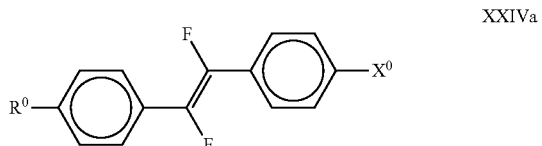
XXIVa

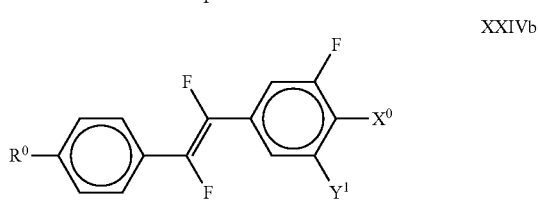
XXIVb

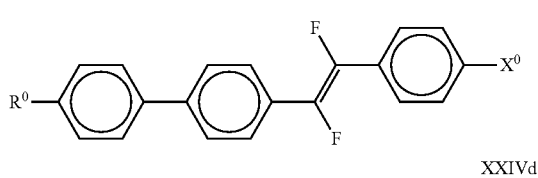
XXIVc

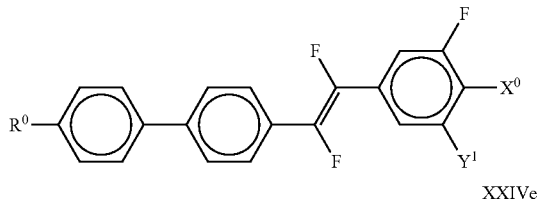
XXIVd

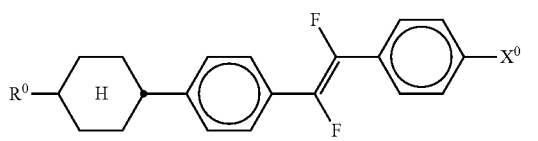
XXIVe

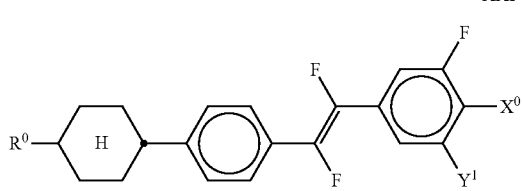
XXIVf

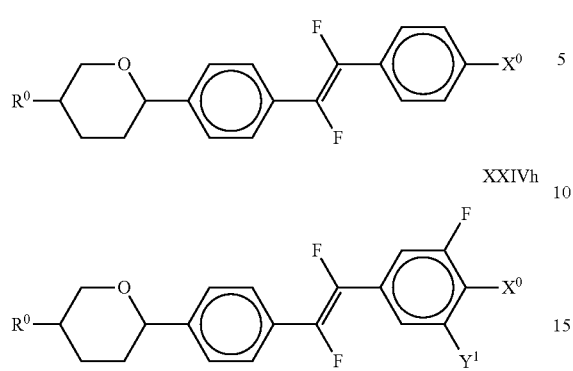

in which R⁰, X⁰ and Y¹ have the meanings indicated above. R⁰ preferably denotes alkyl having 1 to 6 C atoms. X⁰ preferably denotes F, and Y¹ is preferably F;

is preferably

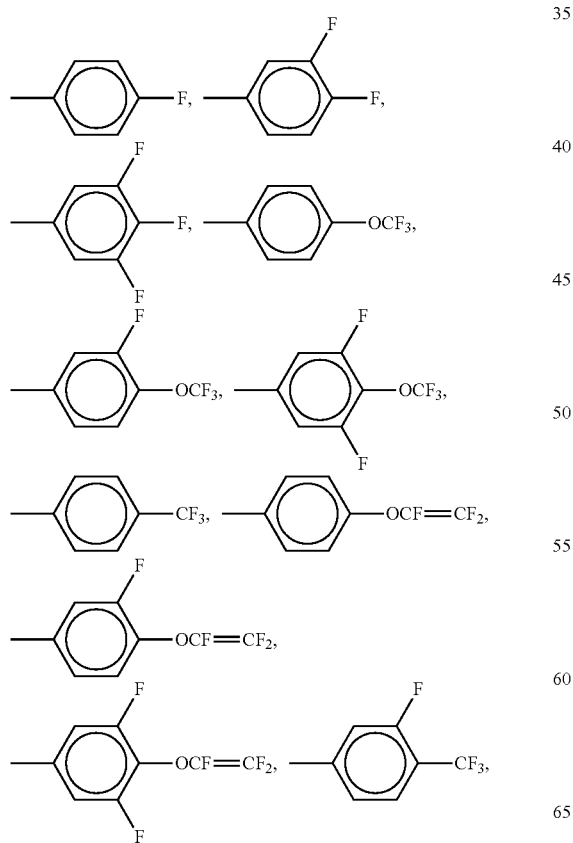

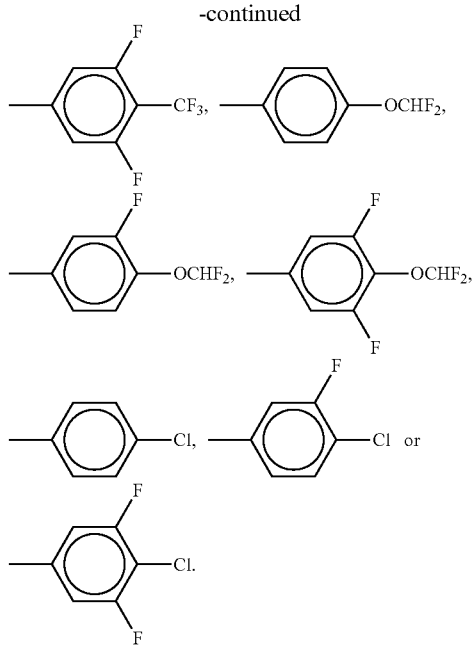

$R^0$ is straight-chain alkyl or alkenyl having 2 to 6 C atoms;

The medium comprises one or more compounds of the following formulae:

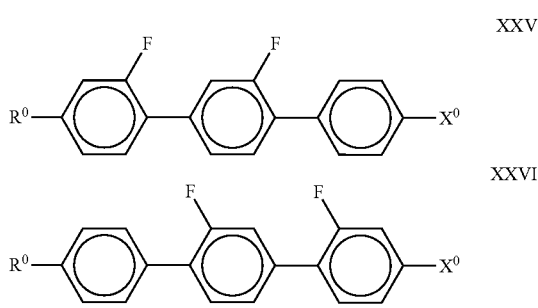

in which $R^0$ and $X^0$ have the meanings indicated above. $R^0$ preferably denotes alkyl having 1 to 6 C atoms. $X^0$ preferably denotes F or Cl. In the formula XXV, $X^0$ very particularly preferably denotes Cl.

The medium comprises one or more compounds of the following formulae:

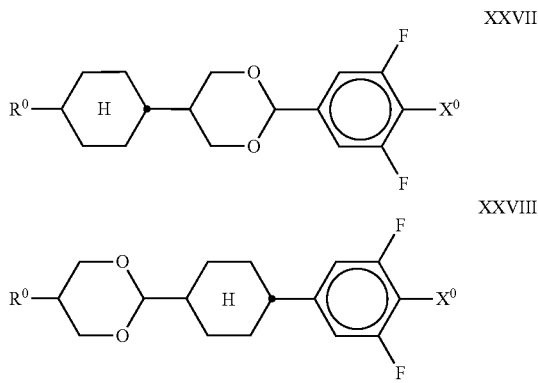

-continued

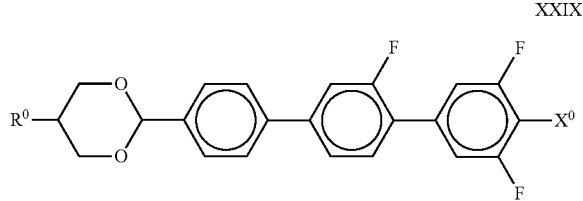

XXIX in which R⁰ and X⁰ have the meanings indicated above. R⁰ preferably denotes alkyl having 1 to 6 C atoms. X⁰ preferably denotes F. The medium according to the invention particularly preferably comprises one or more compounds of the formula XXIX in which X⁰ preferably denotes F. The compound(s) of the formulae XXVII-XXIX is (are) preferably employed in the mixtures according to the invention in amounts of 1-20% by weight, particularly preferably 1-15% by weight. Particularly preferred mixtures comprise at least one compound of the formula XXIX.

The medium comprises one or more compounds of the following pyrimidine or pyridine compounds of the formulae

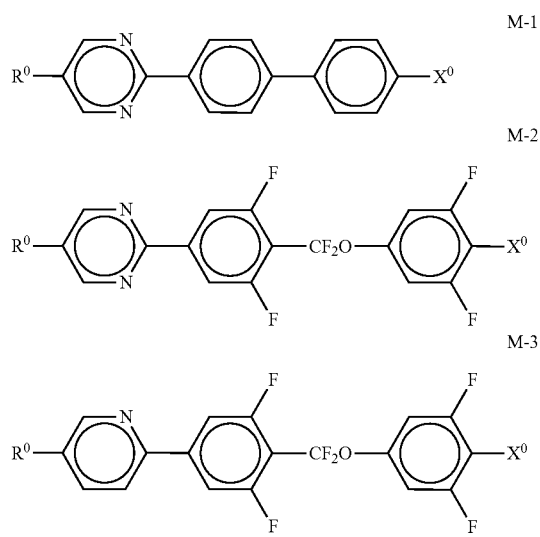

in which R⁰ and X⁰ have the meanings indicated above. R⁰ preferably denotes alkyl having 1 to 6 C atoms. X⁰ preferably denotes F. The medium according to the invention particularly preferably comprises one or more compounds of the formula M-1, in which X⁰ preferably denotes F. The compound(s) of the formulae M-1 to M-3 is (are) preferably employed in the mixtures according to the invention in amounts of 1-20% by weight, particularly preferably 1-15% by weight.

Further preferred embodiments are indicated below:

The medium comprises two or more compounds of the formula IA, in particular of the formula I-4;

The medium comprises 2-40% by weight, preferably 4-30% by weight, particularly preferably 3-15% by weight, of compounds of the formula I, in particular one or more compounds of the formula I-4;

Besides one or more compounds of the formula I, the medium comprises further compounds selected from the group of the compounds of the formulae II, III, IX-XIII, XVII and XVIII;

The proportion of compounds of the formulae II, III, IX-XIII, XVII and XVIII in the mixture as a whole is 40 to 95% by weight;

The medium comprises 10-50% by weight, particularly preferably 12-40% by weight, of compounds of the formulae II and/or III;

The medium comprises 20-70% by weight, particularly preferably 25-65% by weight, of compounds of the formulae IX-XIII;

The medium comprises 4-30% by weight, particularly preferably 5-20% by weight, of compounds of the formula XVII;

The medium comprises 1-20% by weight, particularly preferably 2-15% by weight, of compounds of the formula XVIII;

The medium comprises at least two compounds of the formulae

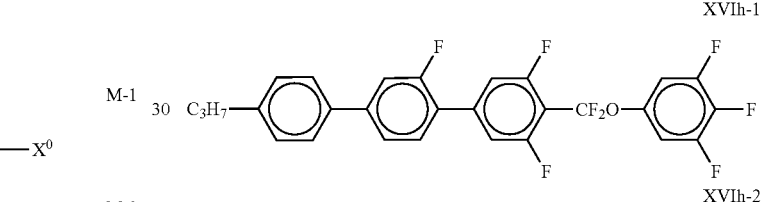

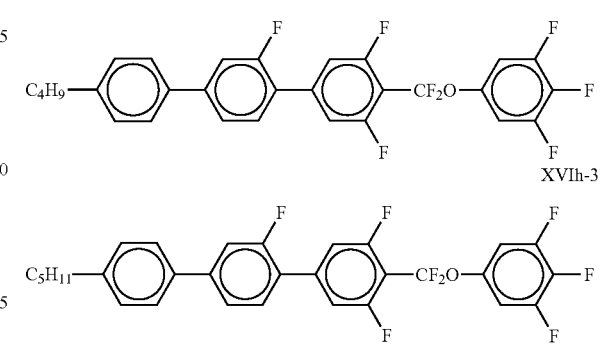

The medium comprises at least two compounds of the formulae

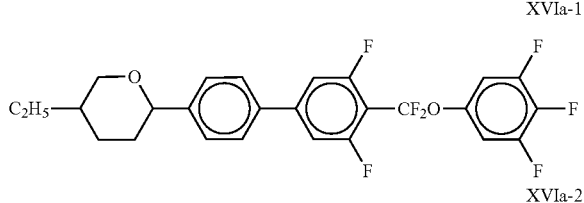

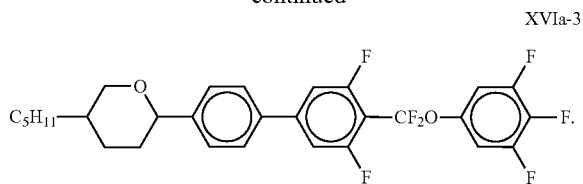

The medium comprises at least one compound of the formula I and at least one compound of the formula IIIa;

The medium comprises ≥20% by weight, preferably ≥24% by weight, preferably 25-60% by weight, of compounds of the formula IXb, in particular the compound of the formula IXb-1,

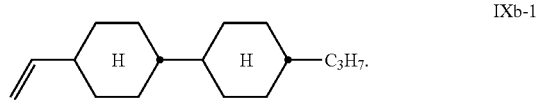

The medium comprises at least one compound of the formula IXb-1 and at least one compound of the formula IXc-1,

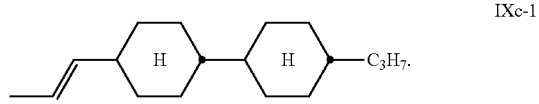

The medium comprises at least one compound of the formula DPGU-n-F.

The medium comprises at least one compound of the formula CDUQU-n-F.

The medium comprises at least one compound of the formula CPU-n-OXF.

The medium comprises at least one compound of the formula PPGU-n-F.

The medium comprises at least one compound of the formula PGP-n-m, preferably two or three compounds.

The medium comprises at least one compound of the formula PGP-2-2V having the structure

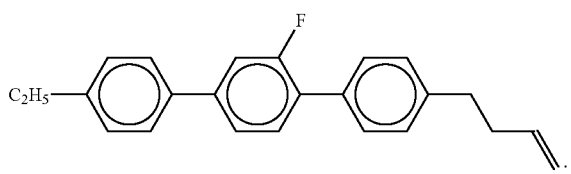

It has been found that ≥2% by weight of one or more compounds of the formula I mixed with conventional liquid-crystal materials, but in particular with one or more compounds of the formulae II to XXVIII, results in a significant increase in the light stability and in high birefringence values, with broad nematic phases with low smectic-nematic transition temperatures being observed at the same time, improving the shelf life. At the same time, the mixtures exhibit very low threshold voltages, very good values for the VHR on exposure to UV, and very high clearing points.

The term "alkyl" or "alkyl*" in this application encompasses straight-chain and branched alkyl groups having 1-6 carbon atoms, in particular the straight-chain groups methyl, ethyl, propyl, butyl, pentyl and hexyl. Groups having 2-5 carbon atoms are generally preferred.

The term "alkenyl" or "alkenyl*" encompasses straight-chain and branched alkenyl groups having 2-6 carbon atoms, in particular the straight-chain groups. Preferred alkenyl groups are $C_2$-$C_7$-1E-alkenyl, $C_4$-$C_6$-3E-alkenyl, in particular $C_2$-$C_6$-1E-alkenyl. Examples of particularly preferred alkenyl groups are vinyl, 1E-propenyl, 1E-butenyl, 1E-pentenyl, 1E-hexenyl, 3-butenyl, 3E-pentenyl, 3E-hexenyl, 4-pentenyl, 4Z-hexenyl, 4E-hexenyl and 5-hexenyl. Groups having up to 5 carbon atoms are generally preferred, in particular $CH_2$=CH, $CH_3CH$=CH, $CH_3CH_2CH_2CH_2$=CH or $CH_3CH_2CH_2$=CH.

The term "fluoroalkyl" preferably encompasses straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxy" preferably encompasses straight-chain radicals of the formula $C_nH_{2n+1}$—O—$(CH_2)_m$, in which n and m each, independently of one another, denote 1 to 6. m may also denote 0. Preferably, n=1 and m=1-6 or m=0 and n=1-3.

Through a suitable choice of the meanings of $R^0$ and $X^0$, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals. The mixtures according to the invention are distinguished, in particular, by high Δn values and thus have significantly faster response times than the mixtures from the prior art.

The optimum mixing ratio of the compounds of the above-mentioned formulae depends substantially on the desired properties, on the choice of the components of the above-mentioned formulae and on the choice of any further components that may be present.

Suitable mixing ratios within the range indicated above can easily be determined from case to case.

The total amount of compounds of the above-mentioned formulae in the mixtures according to the invention is not crucial. The mixtures can therefore comprise one or more further components for the purposes of optimisation of various properties. However, the observed effect on the desired improvement in the properties of the mixture is generally greater, the higher the total concentration of compounds of the above-mentioned formulae.

In a particularly preferred embodiment, the media according to the invention comprise compounds of the formulae II to VIII (preferably II, III, IV and V, in particular IIa and IIIa) in which $X^0$ denotes F, $OCF_3$, $OCHF_2$, OCH=$CF_2$, OCF=$CF_2$ or $OCF_2$—$CF_2H$. A favourable synergistic action with one or more compounds of the formula I results in particularly advantageous properties. In particular, mixtures comprising one or more compounds of the formulae I, IIa and IIIa are distinguished by their low threshold voltage.

The individual compounds of the above-mentioned formulae and the sub-formulae thereof which can be used in the media according to the invention are either known or can be prepared analogously to the known compounds.

The invention also relates to electro-optical displays, such as, for example, STN or MLC displays, having two plane-parallel outer plates, which, together with a frame, form a cell, integrated non-linear elements for switching individual pixels on the outer plates, and a nematic liquid-crystal mixture having positive dielectric anisotropy and high specific resistance located in the cell, which contain media of this type, and to the use of these media for electro-optical purposes.

The liquid-crystal mixtures according to the invention enable a significant broadening of the available parameter latitude. The achievable combinations of clearing point, viscosity at low temperature, thermal and UV stability and high optical anisotropy are far superior to previous materials from the prior art.

The mixtures according to the invention are particularly suitable for mobile applications and TFT applications, such as, for example, mobile telephones and PDAs. Furthermore, the mixtures according to the invention can be used in FFS, VA-IPS, OCB and IPS displays.

The liquid-crystal mixtures according to the invention, while retaining the nematic phase down to −20° C. and preferably down to −30° C., particularly preferably down to −40° C., and the clearing point ≥75° C., preferably ≥80° C., at the same time allow rotational viscosities $\gamma_1$ of ≤110 mPa·s, particularly preferably ≤100 mPa·s, to be achieved, enabling excellent MLC displays having fast response times to be achieved. The rotational viscosities are determined at 20° C.

The dielectric anisotropy ∆∈ of the liquid-crystal mixtures according to the invention at 20° C. is preferably ≥+8, particularly preferably ≥+10, especially preferably ≥12. In addition, the mixtures are characterised by low operating voltages. The threshold voltage of the liquid-crystal mixtures according to the invention is preferably ≤2.0 V. The birefringence ∆n of the liquid-crystal mixtures according to the invention at 20° C. is preferably ≥0.09, particularly preferably ≥0.10.

The nematic phase range of the liquid-crystal mixtures according to the invention preferably has a width of at least 90°, in particular at least 100°. This range preferably extends at least from −25° to +70° C.

It goes without saying that, through a suitable choice of the components of the mixtures according to the invention, it is also possible for higher clearing points (for example above 100° C.) to be achieved at higher threshold voltages or lower clearing points to be achieved at lower threshold voltages with retention of the other advantageous properties. At viscosities correspondingly increased only slightly, it is likewise possible to obtain mixtures having a higher ∆∈ and thus low thresholds. The MLC displays according to the invention preferably operate at the first Gooch and Tarry transmission minimum [C. H. Gooch and H. A. Tarry, Electron. Lett. 10, 2-4, 1974; C. H. Gooch and H. A. Tarry, Appl. Phys., Vol. 8, 1575-1584, 1975], where, besides particularly favourable electro-optical properties, such as, for example, high steepness of the characteristic line and low angle dependence of the contrast (German patent 30 22 818), lower dielectric anisotropy is sufficient at the same threshold voltage as in an analogous display at the second minimum. This enables significantly higher specific resistance values to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

Measurements of the voltage holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formulae IA and IB exhibit a significantly smaller decrease in the HR on UV exposure than analogous mixtures comprising cyanophenylcyclohexanes of the formula

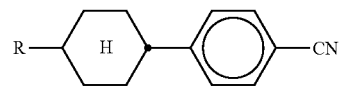

or esters of the formula

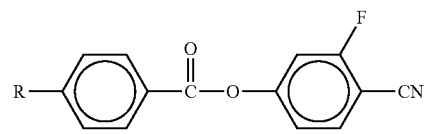

instead of the compounds of the formulae IA and IB.

The light stability and UV stability of the mixtures according to the invention are considerably better, i.e. they exhibit a significantly smaller decrease in the HR on exposure to light or UV.

The construction of the MLC display according to the invention from polarisers, electrode base plates and surface-treated electrodes corresponds to the usual design for displays of this type. The term usual design is broadly drawn here and also encompasses all derivatives and modifications of the MLC display, in particular including matrix display elements based on poly-Si TFTs or MIM.

A essential difference between the displays according to the invention and the hitherto conventional displays based on the twisted nematic cell consists, however, in the choice of the liquid-crystal parameters of the liquid-crystal layer.

The liquid-crystal mixtures which can be used in accordance with the invention are prepared in a manner conventional per se, for example by mixing one or more compounds of the formula I with one or more compounds of the formulae II-XXVIII or with further liquid-crystalline compounds and optionally with additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature, such as, for example, UV stabilisers, such as Tinuvin®, e.g. Tinuvin® 770, from Ciba Chemicals, antioxidants, e.g. TEMPOL, microparticles, free-radical scavengers, nanoparticles, etc. For example, 0-15% of pleochroic dyes or chiral dopants can be added. Suitable stabilisers and dopants are mentioned below in Tables C and D.

Polymerisable compounds, so-called reactive mesogens (RMs), for example as disclosed in U.S. Pat. No. 6,861,107, may furthermore be added to the mixtures according to the invention in concentrations of preferably 0.12-5% by weight, particularly preferably 0.2-2% by weight, based on the mixture. These mixtures may optionally also comprise an initiator, as described, for example, in U.S. Pat. No. 6,781,665. The initiator, for example Irganox-1076 from Ciba, is preferably added to the mixture comprising polymerisable compounds in amounts of 0-1%. Mixtures of this type can be used for so-called polymer-stabilised VA modes (PS-VA) or PSA (polymer sustained VA), in which polymerisation of the reactive mesogens is intended to take place in the liquid-crystalline mixture. The prerequisite for this is that the liquid-crystal mixture does not itself comprise any polymerisable components.

In a preferred embodiment of the invention, the polymerisable compounds are selected from the compounds of the formula M

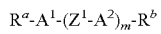     M in which the individual radicals have the following meanings:

$R^a$ and $R^b$ each, independently of one another, denote P, P-Sp-, H, halogen, $SF_5$, $NO_2$, a carbon group or hydrocarbon group, where at least one of the radicals $R^a$ and $R^b$ preferably denotes or contains a group P or P-Sp-, P on each occurrence, identically or differently, denotes a polymerisable group, Sp on each occurrence, identically or differently, denotes a spacer group or a single bond, $A^1$ and $A^2$ each, independently of one another, denote an aromatic, heteroaromatic, alicyclic or heterocyclic group, preferably having 4 to 25 ring atoms, which may also contain fused rings, and which may also be mono- or polysubstituted by L, L denotes P-Sp-, H, OH, $CH_2OH$, halogen, $SF_5$, $NO_2$, a carbon group or hydrocarbon group, $Z^1$ on each occurrence, identically or differently, denotes —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —C≡C—, —CH=CH—, —COO—, —OCO—CH=CH—, $CR^0R^{00}$ or a single bond, $R^0$ and $R^{00}$ each, independently of one another, denote H or alkyl having 1 to 12 C atoms, m denotes 0, 1, 2, 3 or 4, and n1 denotes 1, 2, 3 or 4.

Particularly preferred compounds of the formula M are those in which $R^a$ and $R^b$ each, independently of one another, denote P, P-Sp-, H, F, Cl, Br, I, —CN, —NO$_2$, —NCO, —NCS, —OCN, —SCN, $SF_5$ or straight-chain or branched alkyl having 1 to 25 C atoms, in which, in addition, one or more non-adjacent CH$_2$ groups may each be replaced, independently of one another, by —C(R$^0$)=C(R$^{00}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN, P or P-Sp-, where at least one of the radicals $R^a$ and $R^b$ denotes or contains a group P or P-Sp-, $A^1$ and $A^2$ each, independently of one another, denote 1,4-phenylene, naphthalene-1,4-diyl, naphthalene-2,6-diyl, phenanthrene-2,7-diyl, anthracene-2,7-diyl, fluorene-2,7-diyl, 2-oxo-2H-chromene-3,6-diyl, 2-oxo-2H-chromene-3,7-diyl, 4-oxo-4H-chromene-2,6-diyl, 4-oxo-4H-chromene-3,6-diyl, 4-oxo-4H-chromene-3,7-diyl (trivial name coumarine or flavone), where, in addition, one or more CH groups in these groups may be replaced by N, cyclohexane-1,4-diyl, in which, in addition, one or more non-adjacent CH$_2$ groups may be replaced by O and/or S, 1,4-cyclohexenylene, bicyclo[1.1.1]pentane-1,3-diyl, bicyclo[2.2.2]octane-1,4-diyl, spiro[3.3]heptane-2,6-diyl, piperidine-1,4-diyl, decahydronaphthalene-2,6-diyl, 1,2,3,4-tetrahydronaphthalene-2,6-diyl, indane-2,5-diyl or octahydro-4,7-methanoindane-2,5-diyl, where all these groups may be unsubstituted or mono- or polysubstituted by L, L denotes P, P-Sp-, OH, $CH_2OH$, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F, Cl, P or P-Sp-, P denotes a polymerisable group, $Y^1$ denotes halogen, $R^x$ denotes P, P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl, P or P-Sp-, an optionally substituted aryl or aryloxy group having 6 to 40 C atoms, or an optionally substituted heteroaryl or heteroaryloxy group having 2 to 40 C atoms.

Further preferred compounds of the formula M are those selected from one or more of the following sub-groups:

m is 2 or 3, m is 2, $R^a$ and $R^b$ denote identical or different groups P-Sp-, $R^a$ and $R^b$ denote identical or different groups P-Sp-, in which one or more groups Sp denote a single bond, m is 2 or 3 and $R^a$ and $R^b$ denote identical groups P-Sp-, one of the radicals $R^a$ and $R^b$ denotes P-Sp- and the other denotes an unpolymerisable group, preferably straight-chain or branched alkyl having 1 to 25 C atoms, in which, in addition, one or more non-adjacent CH$_2$ groups may each be replaced, independently of one another, by —C(R$^{00}$)=C(R$^{000}$)—, —C≡C—, —N(R$^{00}$)—, —O—, —S—, —CO—, —CO—O—, —O—CO— or —O—CO—O— in such a way that O and/or S atoms are not linked directly to one another, and in which, in addition, one or more H atoms may be replaced by F, Cl, Br, I or CN, one or more groups Sp denote a single bond, one or more groups Sp denote —(CH$_2$)$_{p1}$—, —(CH$_2$)$_{p1}$—O—, —(CH$_2$)$_{p1}$—OCO— or —(CH$_2$)$_{p1}$—OCOO—, in which p1 denotes an integer from 1 to 12 and r1 denotes an integer from 1 to 8, L does not denote and/or contain a polymerisable group, $A^1$ and $A^2$ denote, independently of one another, 1,4-phenylene or naphthalene-2,6-diyl, where, in addition, one or more CH groups in these groups may be replaced by N, and which may also be mono- or polyfluorinated, $Z^1$ is selected from the group consisting of —O—, —CO—O—, —OCO—, —OCH$_2$—, —CH$_2$O—, —CF$_2$O—, —OCF$_2$—, —CH$_2$CH$_2$—, —CH=CH—, —CF=CF—, —CH=CF—, —CF=CH—, —C≡C— and a single bond, L is an unpolymerisable group, preferably selected from the group consisting of F, Cl, —CN, straight-chain and branched alkyl having 1 to 25 C atoms, in which, in addition, one or more non-adjacent CH$_2$ groups may each be replaced, independently of one another, by —C(R$^{00}$)=C(R$^{000}$)—, —C≡C—, —N(R$^{00}$)—, —O—, —S—, —CO—, —CO—O—, —O—CO— or —O—CO—O— in such a way that O and/or S atoms are not linked directly to one another, and in which, in addition, one or more H atoms may be replaced by F, Cl, Br, I or CN.

Suitable and preferred comonomers for the preparation of mixtures according to the invention for PS-VA, PS-IPS and PS-FFS applications are selected, for example, from the following formulae:

M1
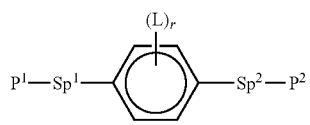

M2
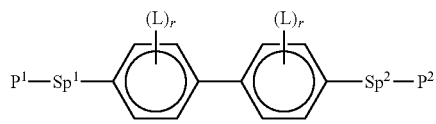

M3
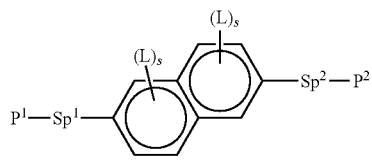

M4
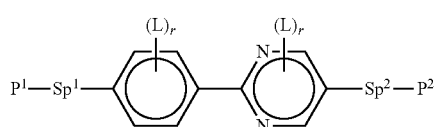

M5
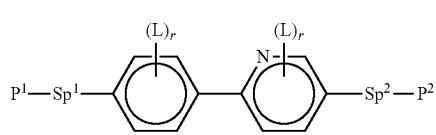

M6
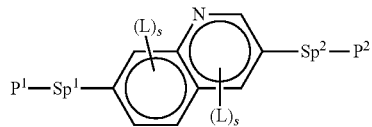

M7
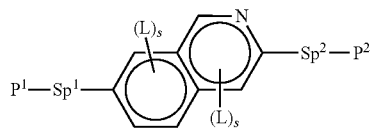

M8
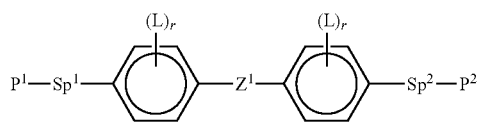

M9
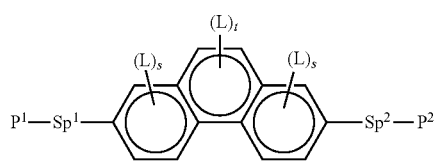

M10
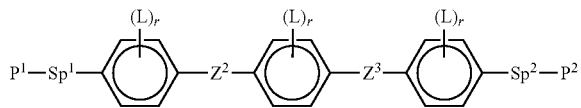

M11
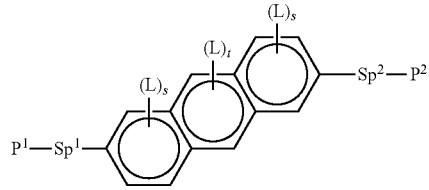

M12
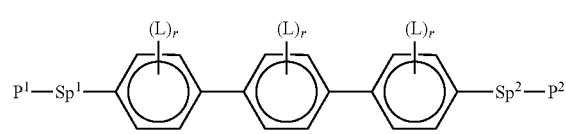

M13
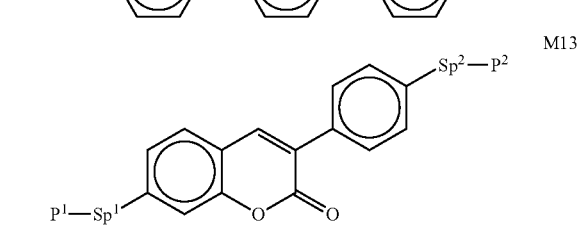

M14
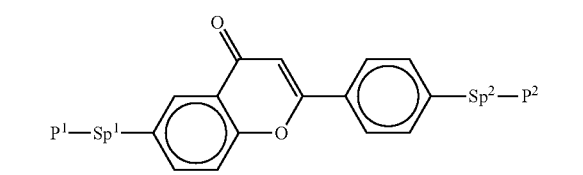

M15
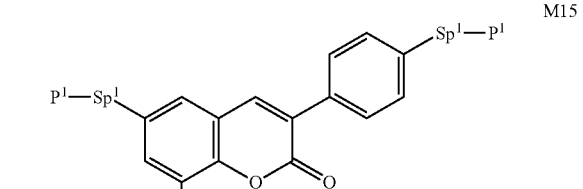

M16
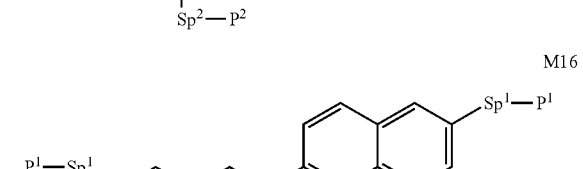

M17
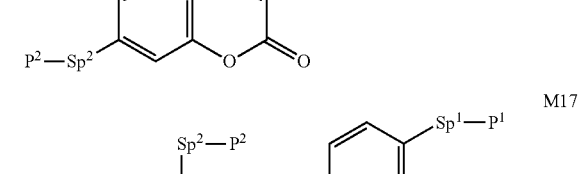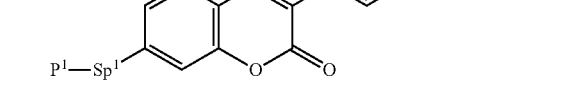

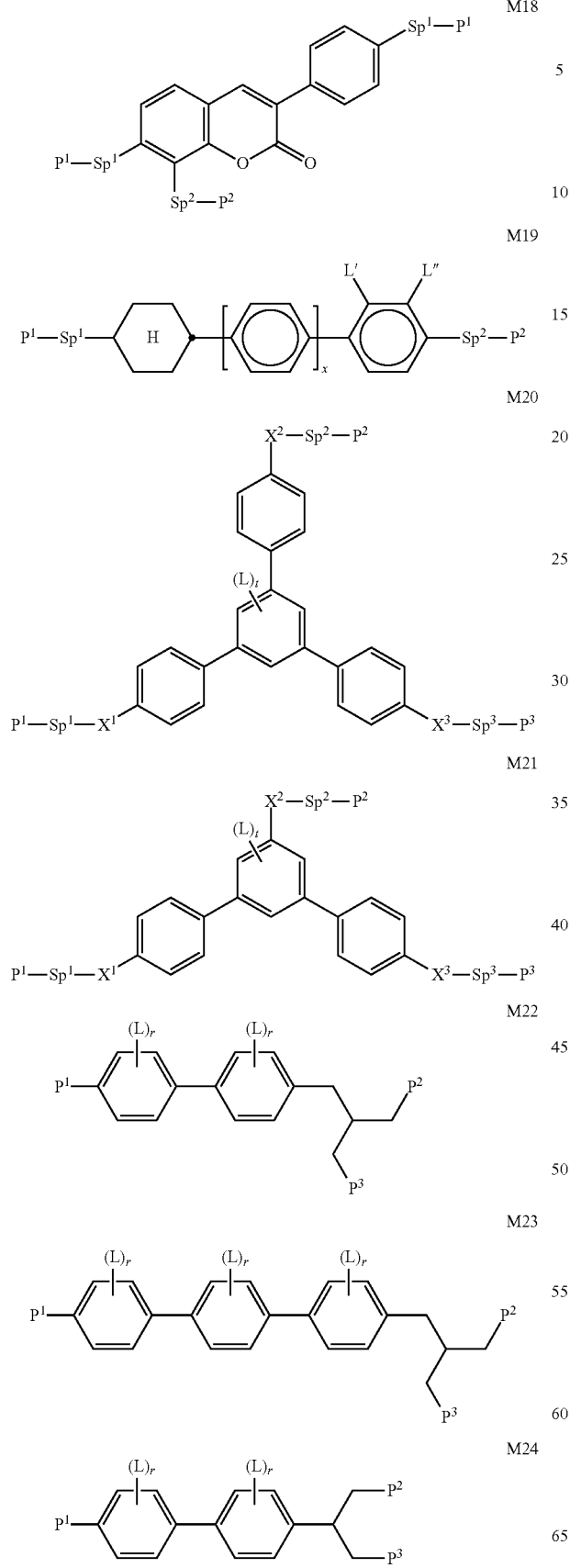
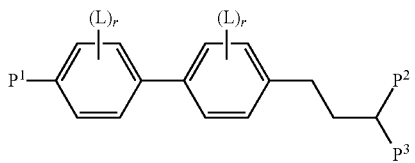
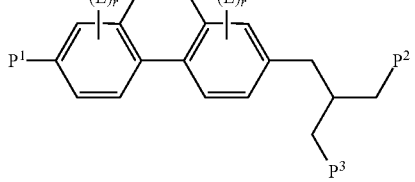
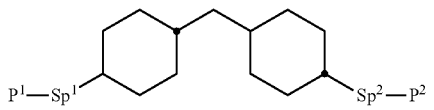
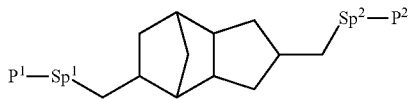
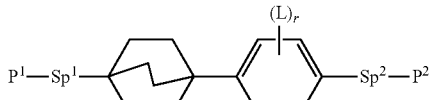
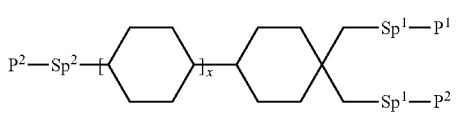
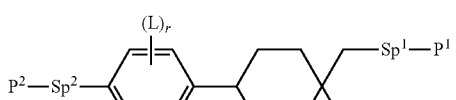
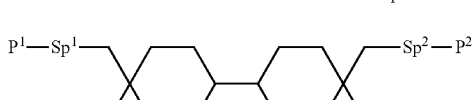
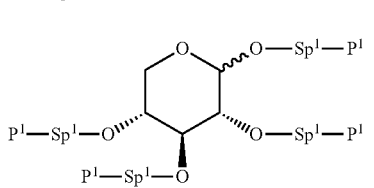

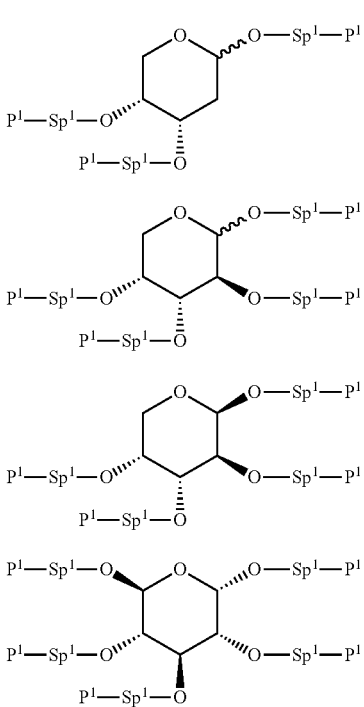

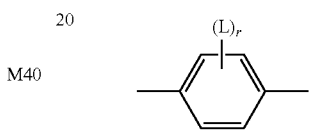

in which the individual radicals have the following meanings:

$P^1$, $P^2$ and $P^3$ each, independently of one another, denote a polymerisable group, preferably having one of the meanings indicated above and below for P, particularly preferably an acrylate, methacrylate, fluoroacrylate, oxetane, vinyloxy or epoxy group, $Sp^1$, $Sp^2$ and $Sp^2$ each, independently of one another, denote a single bond or a spacer group, preferably having one of the meanings indicated above and below for $Sp^a$, and particularly preferably $-(CH_2)_{p1}-$, $-(CH_2)_{p1}-O-$, $-(CH_2)_{p1}-CO-O-$ or $-(CH_2)_{p1}-O-CO-O-$, in which p1 is an integer from 1 to 12, and where the linking of the last-mentioned groups to the adjacent ring takes place via the O atom, where, in addition, one or more of the radicals $P^1$-$Sp^1$-, $P^2$-$Sp^2$- and $P^3$-$Sp^3$- may denote a radical $R^{aa}$, with the proviso that at least one of the radicals $P^1$-$Sp^1$-, $P^2$-$Sp^2$- and $P^3$-$Sp^3$- present does not denote $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $-C(R^0)=C(R^{00})-$, $-C\equiv C-$, $-N(R^0)-$, $-O-$, $-S-$, $-CO-$, $-CO-O-$, $-O-CO-$, $-O-CO-O-$ in such a way that O and/or S atoms are not linked directly to one another, and in which, in addition, one or more H atoms may be replaced by F, Cl, CN or $P^1$-$Sp^1$-, particularly preferably straight-chain or branched, optionally mono- or polyfluorinated alkyl, alkoxy, alkenyl, alkynyl, alkylcarbonyl, alkoxycarbonyl or alkylcarbonyloxy having 1 to 12 C atoms (where the alkenyl and alkynyl radicals have at least two C atoms and the branched radicals have at least three C atoms), $R^0$, $R^{00}$ each, independently of one another and on each occurrence identically or differently, denote H or alkyl having 1 to 12 C atoms, $R^y$ and $R^z$ each, independently of one another, denote H, F, $CH_3$ or $CF_3$, $X^1$, $X^2$ and $X^3$ each, independently of one another, denote $-CO-O-$, $-O-CO-$ or a single bond, $Z^1$ denotes $-O-$, $-CO-$, $-C(R^yR^z)-$ or $-CF_2CF_2-$, $Z^2$ and $Z^3$ each, independently of one another, denote $-CO-O-$, $-O-CO-$, $-CH_2O-$, $-OCH_2-$, $-CF_2O-$, $-OCF_2-$ or $-(CH_2)_n-$, where n is 2, 3 or 4, L on each occurrence, identically or differently, denotes F, Cl, CN, SCN, $SF_5$ or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, and x denotes 0 or 1.

In the compounds of the formulae M1 to M34, preferably denotes

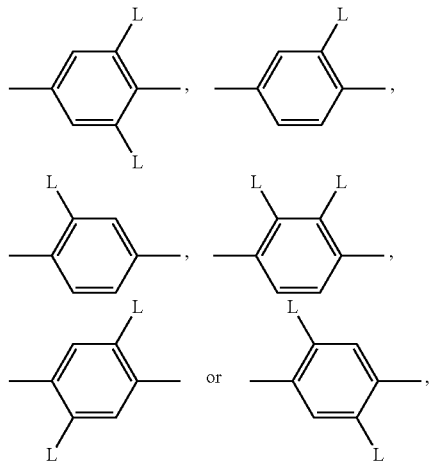

in which L, identically or differently on each occurrence, has one of the above meanings and preferably denotes F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$ or P-Sp-, particularly preferably F, Cl, CN, $CH_3$, $C_2H_5$, $OCH_3$, $COCH_3$, $OCF_3$ or P-Sp-, very particularly preferably F, Cl, $CH_3$, $OCH_3$, $COCH_3$ or $OCF_3$, in particular F or $CH_3$.

The liquid-crystalline media in accordance with the present application preferably comprise in total 0.01 to 10%, preferably 0.2 to 4.0%, particularly preferably 0.2 to 2.0%, of polymerisable compounds.

Particular preference is given to the polymerisable compounds of the formula M.

The present invention thus also relates to the use of the mixtures according to the invention in electro-optical displays and to the use of the mixtures according to the invention in shutter glasses, in particular for 3D applications, and in TN, PS-TN, STN, TN-TFT, OCB, IPS, PS-IPS, FFS, PS-FFS and PS-VA-IPS displays.

In the present application and in the examples below, the structures of the liquid-crystal compounds are indicated by means of acronyms, the transformation into chemical formulae taking place in accordance with Table A. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nN.F.F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF.F | $C_nH_{2n+1}$ | F | F | H |
| nF.F.F | $C_nH_{2n+1}$ | F | F | F |
| nOCF$_3$ | $C_nH_{2n+1}$ | OCF$_3$ | H | H |
| nOCF$_3$.F | $C_nH_{2n+1}$ | OCF$_3$ | F | H |
| n-Vm | $C_nH_{2n+1}$ | —CH=CH—$C_mH_{2m+1}$ | H | H |
| nV-Vm | $C_nH_{2n+1}$—CH=CH— | —CH=CH—$C_mH_{2m+1}$ | H | H |

Preferred mixture components are shown in Tables A and B.

TABLE A

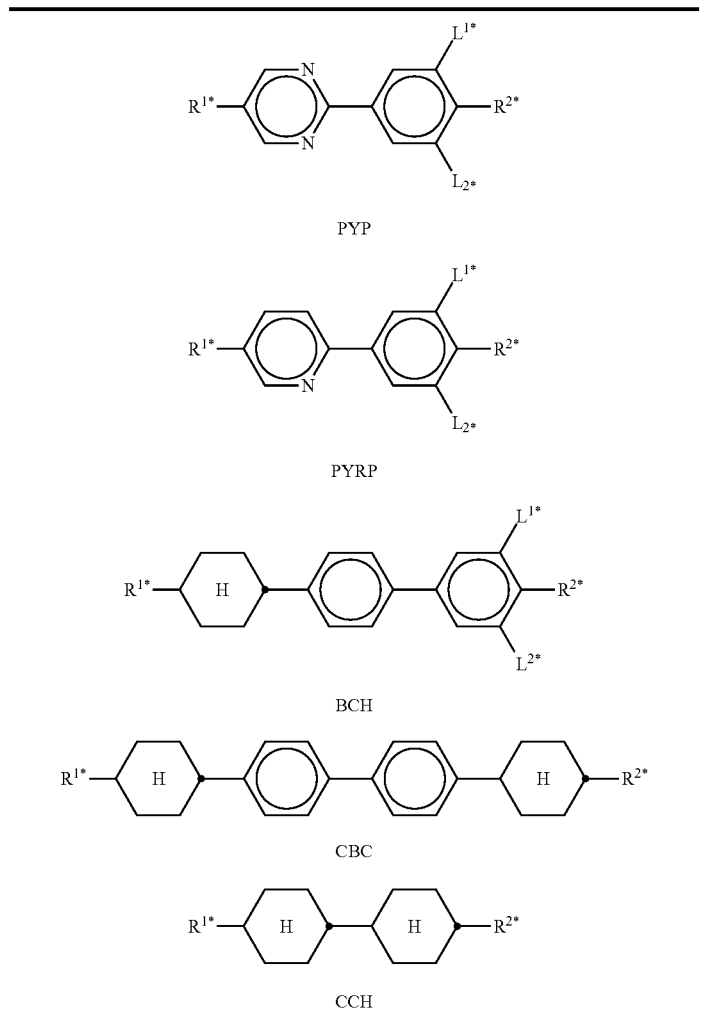

PYP

PYRP

BCH

CBC

CCH

TABLE A-continued
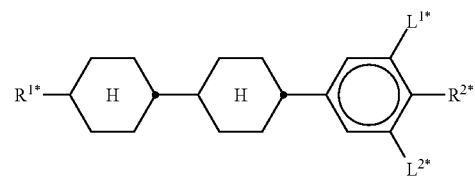
CCP
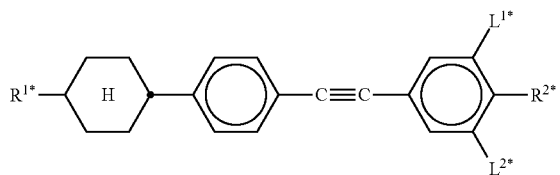
CPTP
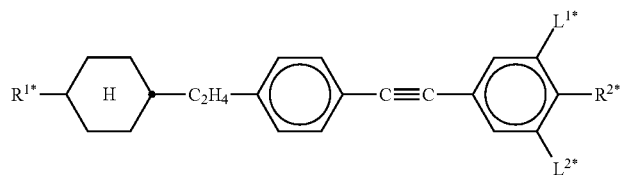
CEPTP
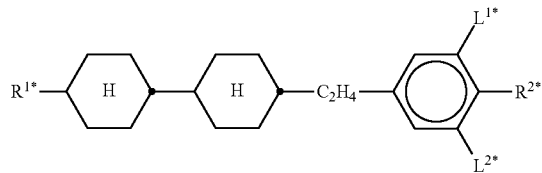
ECCP
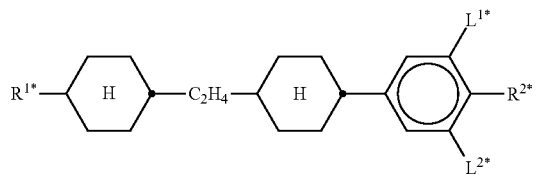
CECP
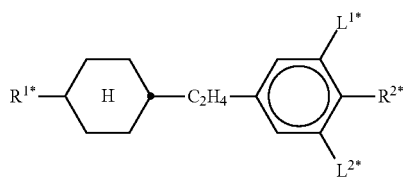
EPCH
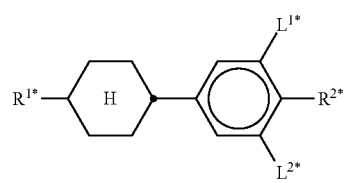
PCH TABLE A-continued
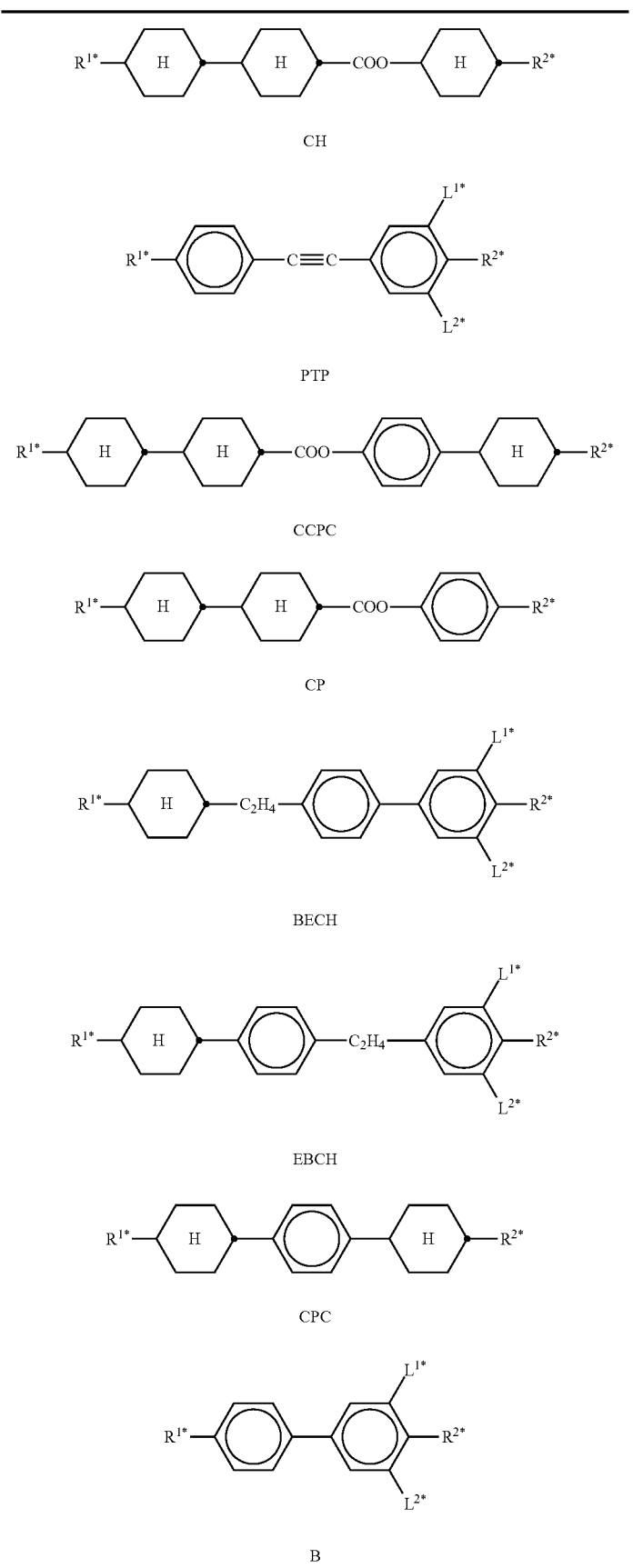

TABLE A-continued
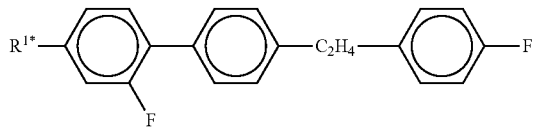
FET-nF
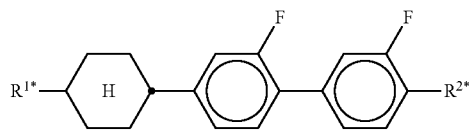
CGG
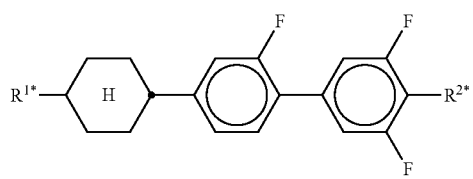
CGU
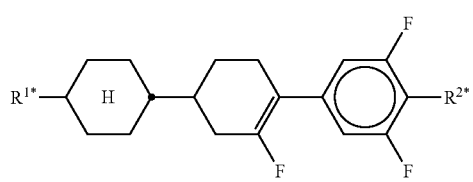
CFU
TABLE B
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
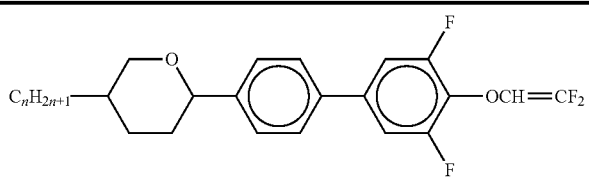
APU-n-OXF
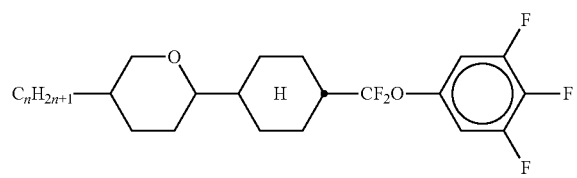
ACQU-n-F
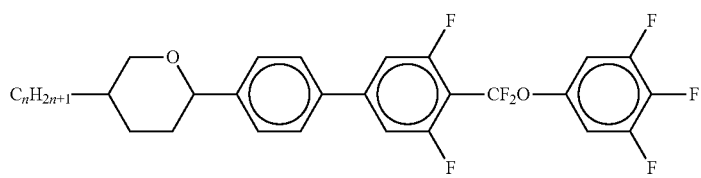
APUQU-n-F TABLE B-continued
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
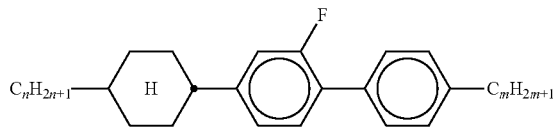
BCH-n•Fm
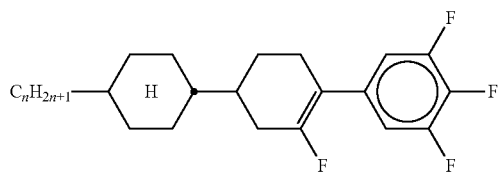
CFU-n-F
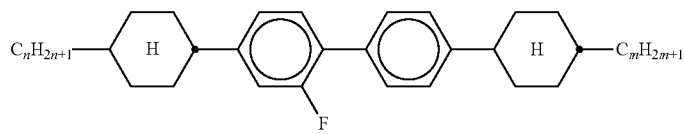
CBC-nmF
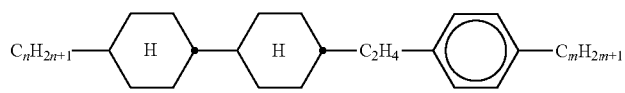
ECCP-nm
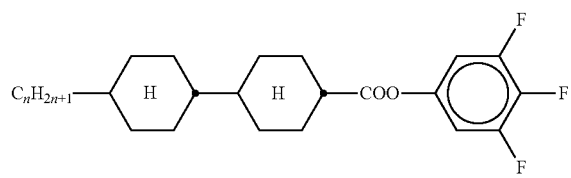
CCZU-n-F
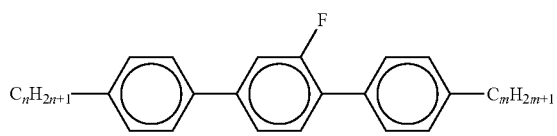
PGP-n-m
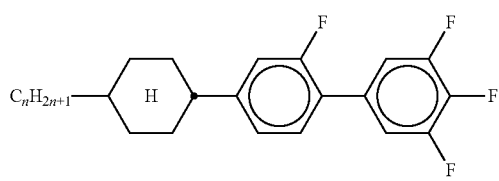
CGU-n-F TABLE B-continued
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
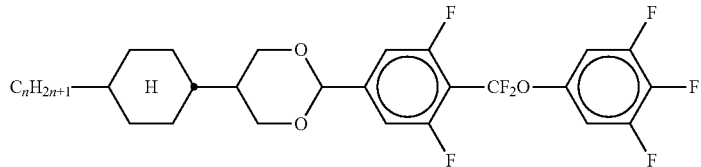
CDUQU-n-F
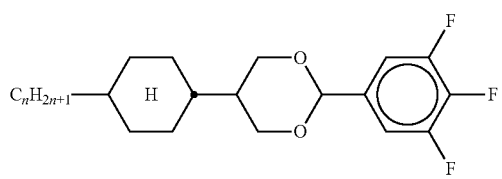
CDU-n-F
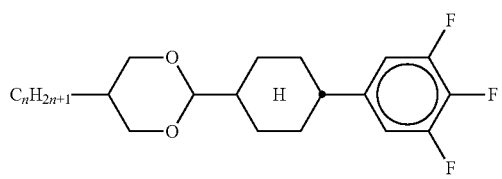
DCU-n-F
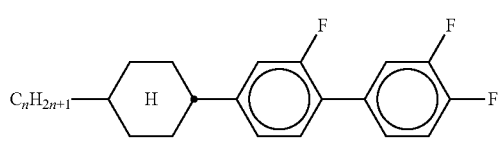
CGG-n-F
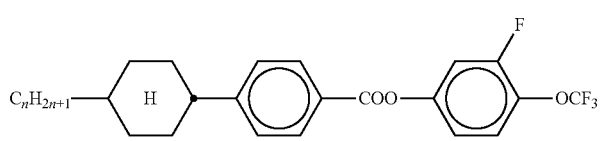
CPZG-n-OT
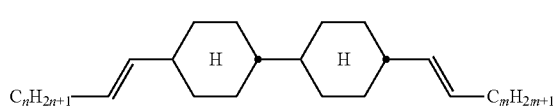
CC-nV-Vm
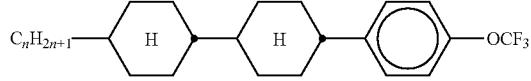
CCP-nOCF$_3$
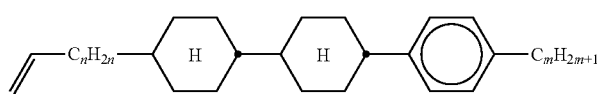
CCP-Vn-m TABLE B-continued
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
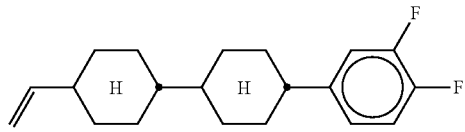
CCG-V-F
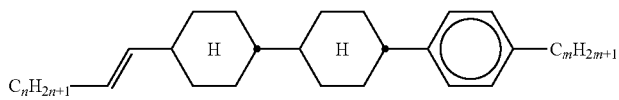
CCP-nV-m
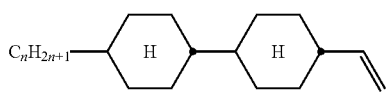
CC-n-V
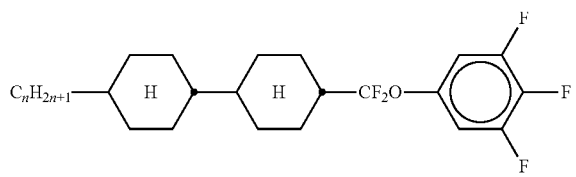
CCQU-n-F
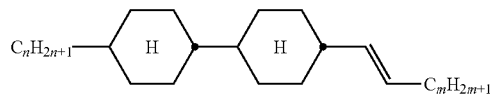
CC-n-Vm
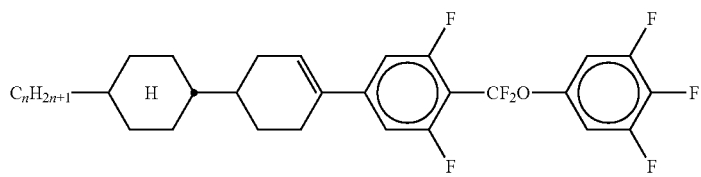
CLUQU-n-F
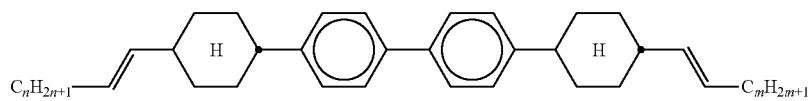
CPPC-nV-Vm
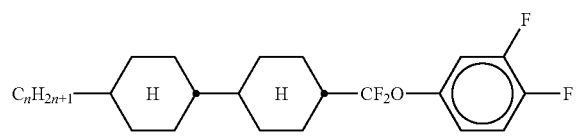
CCQG-n-F TABLE B-continued
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
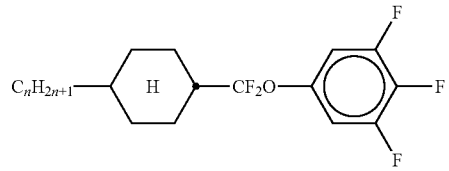
CQU-n-F
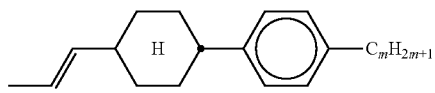
CP-1V-m
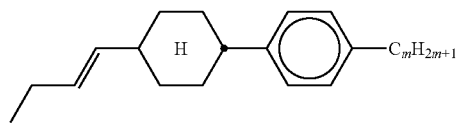
CP-2V-m
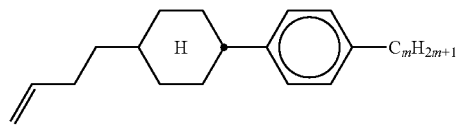
CP-V2-m
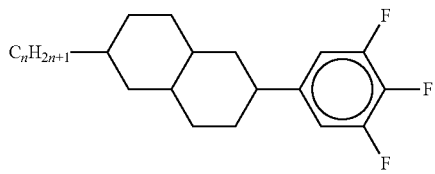
Dec-U-n-F
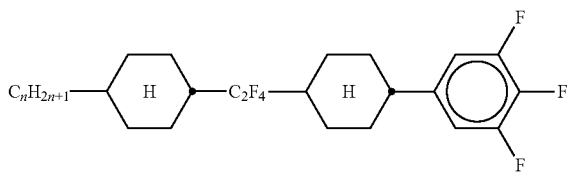
CWCU-n-F
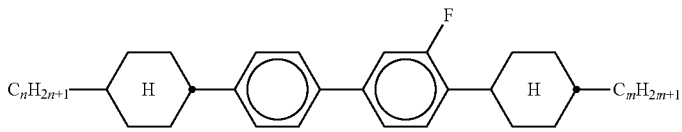
CPGP-n-m
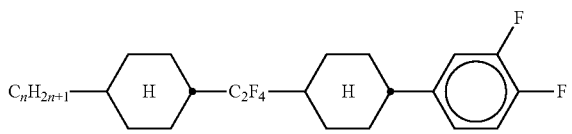
CWCG-n-F TABLE B-continued
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
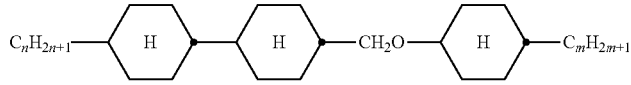
CCOC-n-m
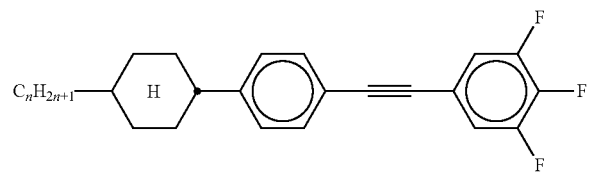
CPTU-n-F
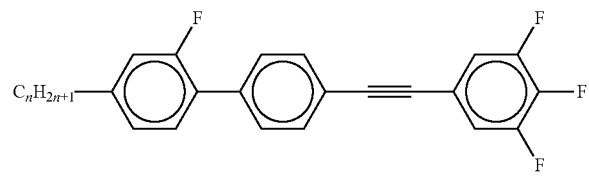
GPTU-n-F
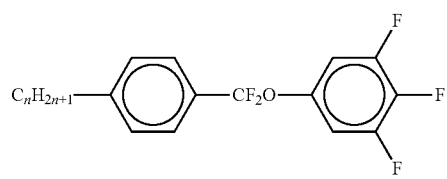
PQU-n-F
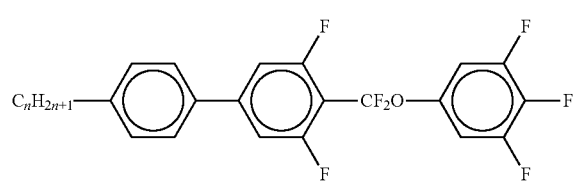
PUQU-n-F
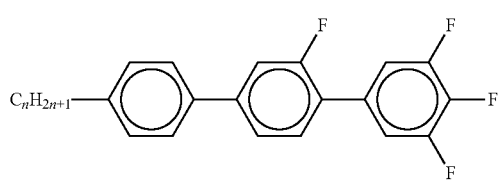
PGU-n-F
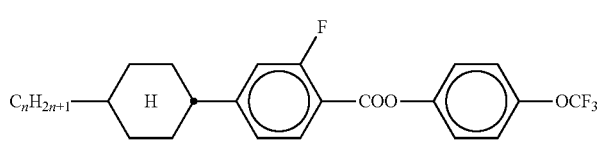
CGZP-n-OT TABLE B-continued
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
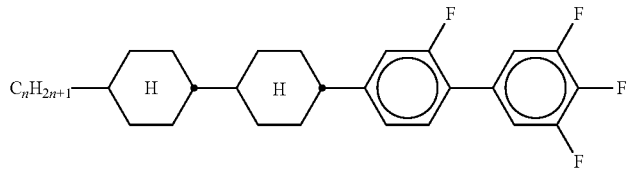
CCGU-n-F
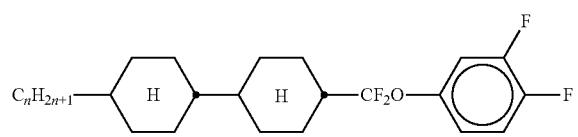
CCQG-n-F
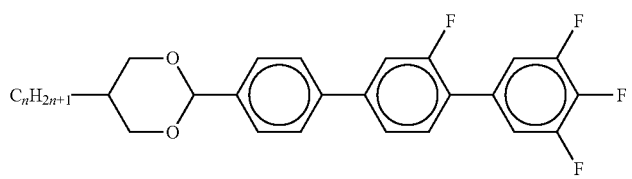
DPGU-n-F
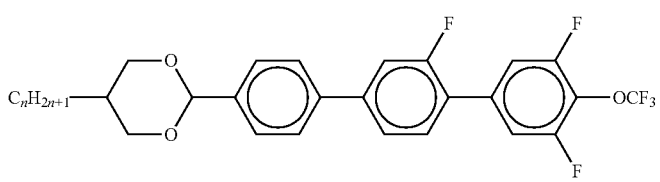
DPGU-n-OT
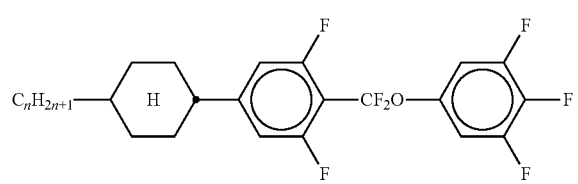
CUQU-n-F
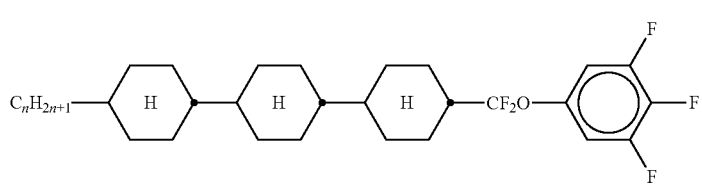
CCCQU-n-F
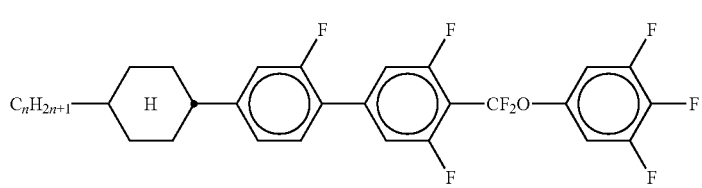
CGUQU-n-F TABLE B-continued
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
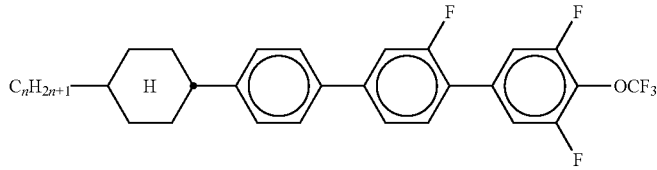
CPGU-n-OT
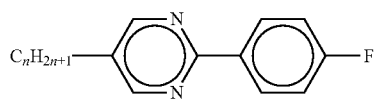
PYP-nF
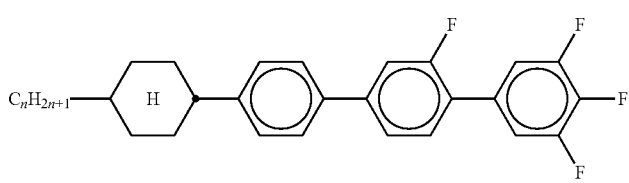
CPGU-n-F
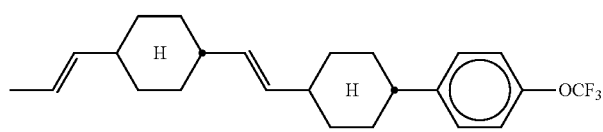
CVCP-1V-OT
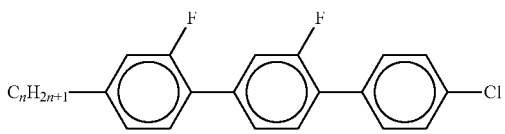
GGP-n-Cl
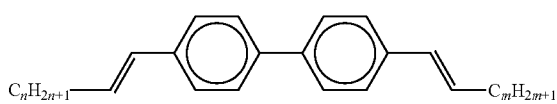
PP-nV-Vm
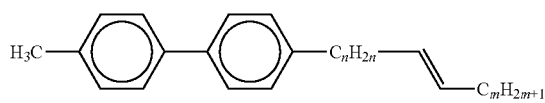
PP-1-nVm
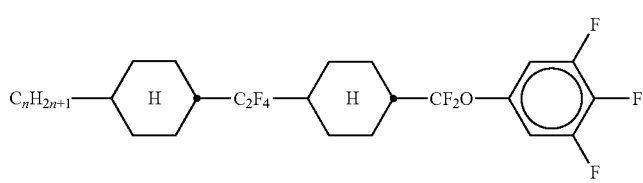
CWCQU-n-F TABLE B-continued
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
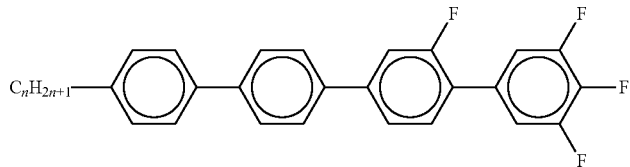
PPGU-n-F
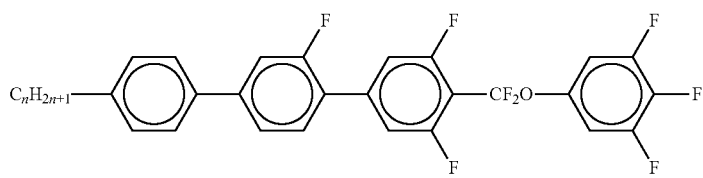
PGUQU-n-F
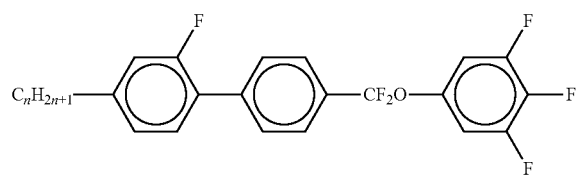
GPQU-n-F
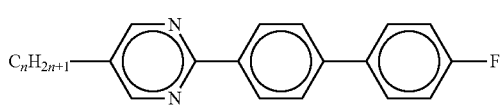
MPP-n-F
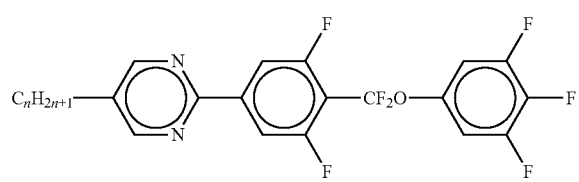
MUQU-n-F
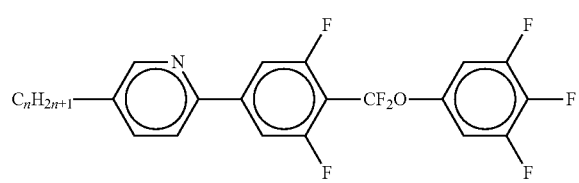
NUQU-n-F
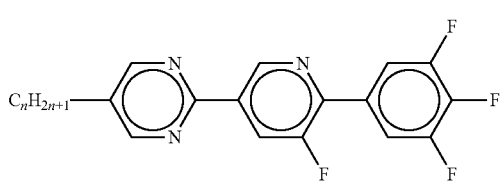
MN(F)U-n-F TABLE B-continued
In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.
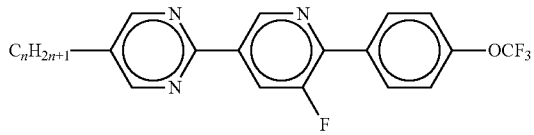
MN(F)P-n-OT
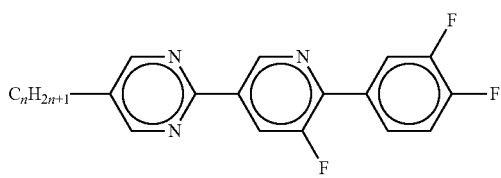
MN(F)G-n-F
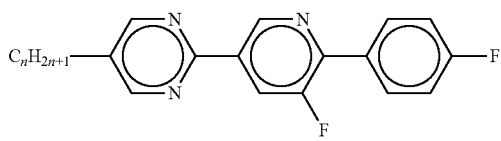
MN(F)P-n-F
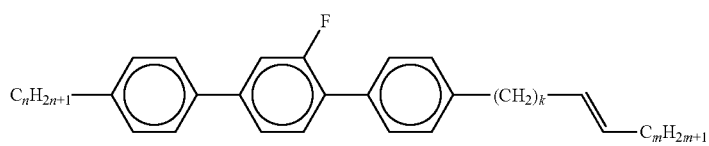
PGP-n-kVm
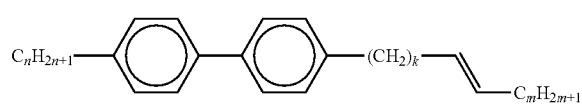
PP-n-kVm
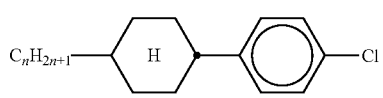
PCH-nCl
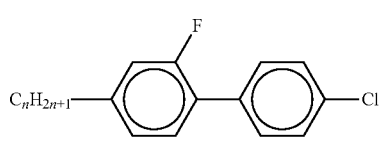
GP-n-Cl
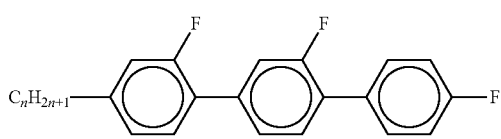
GGP-n-F

TABLE B-continued

In the following formulae, n and m each, independently of one another, denote 0, 1, 2, 3, 4, 5, 6, 7, 8, 9, 10, 11 or 12, in particular 2, 3, 5, furthermore 0, 4, 6. k denotes 0, 1, 2, 3, 4, 5 or 6.

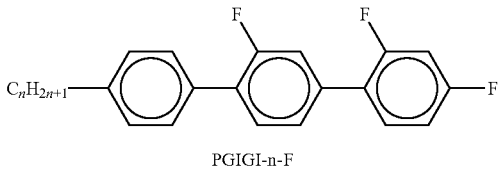

PGIGI-n-F

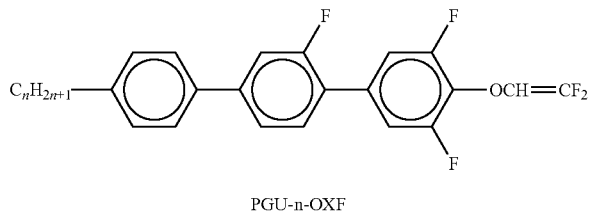

PGU-n-OXF

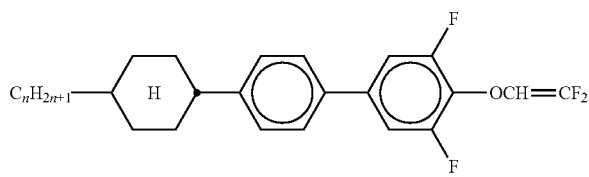

CPU-n-OXF

Particular preference is given to liquid-crystalline mixtures which, besides the compound of the formula I, comprise at least one, two, three, four or more compounds from Table B.

TABLE C

Table C indicates possible dopants which are generally added to the mixtures according to the invention. The mixtures preferably comprise 0-10% by weight, in particular 0.01-5% by weight and particularly preferably 0.01-3% by weight of dopants.

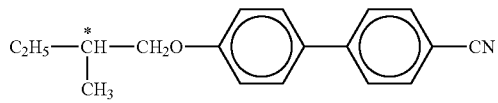

C 15

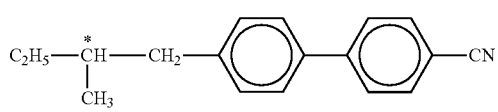

CB 15

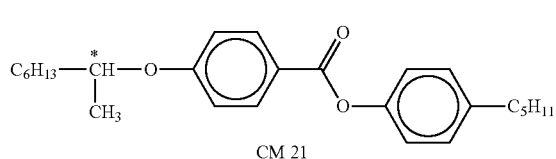

CM 21

TABLE C-continued
Table C indicates possible dopants which are generally added to the mixtures according to the invention. The mixtures preferably comprise 0-10% by weight, in particular 0.01-5% by weight and particularly preferably 0.01-3% by weight of dopants.
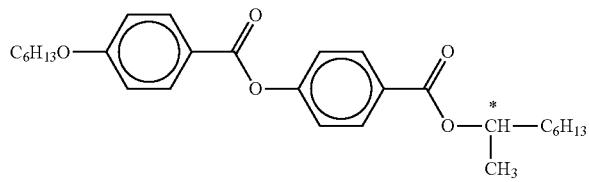
R/S-811
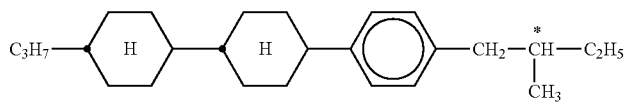
CM 44
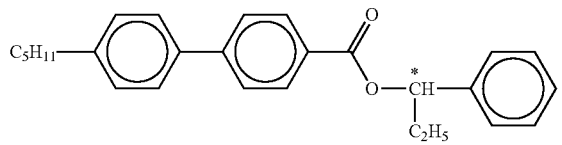
CM 45
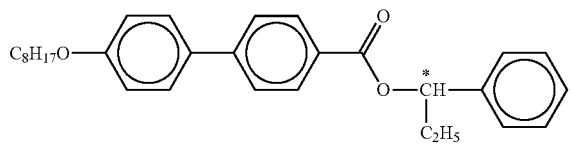
CM 47
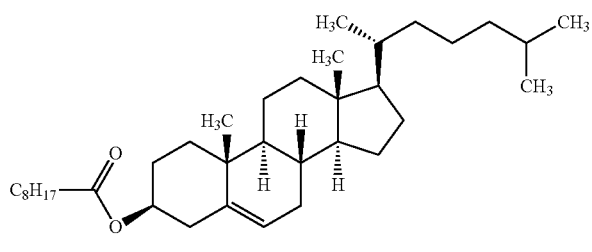
CN
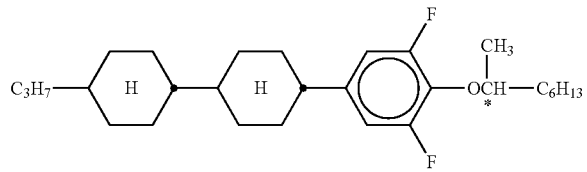
R/S-2011
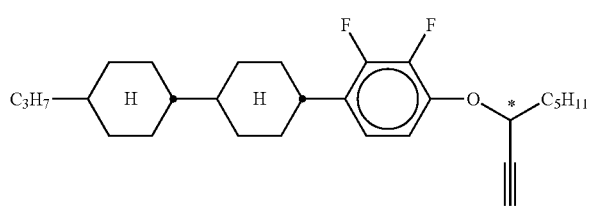
R/S-3011

TABLE C-continued

Table C indicates possible dopants which are generally added to the mixtures according to the invention. The mixtures preferably comprise 0-10% by weight, in particular 0.01-5% by weight and particularly preferably 0.01-3% by weight of dopants.

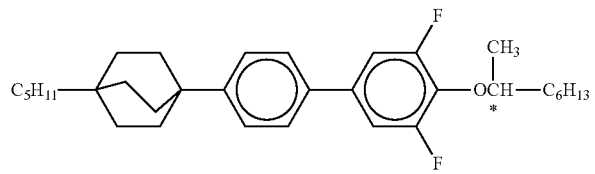

R/S-4011

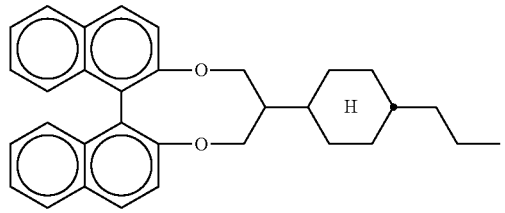

R/S-5011

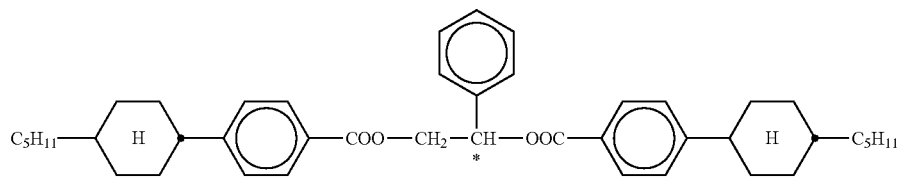

R/S-1011

TABLE D

Stabilisers, which can be added, for example, to the mixtures according to the invention in amounts of 0-10% by weight, are mentioned below.
(n = 1-12)

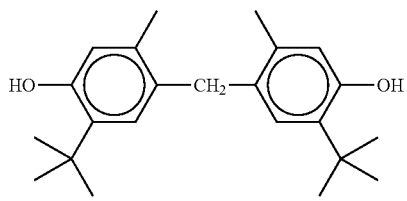

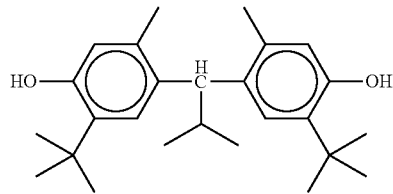

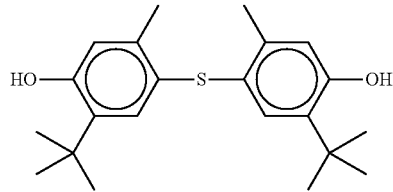

TABLE D-continued
Stabilisers, which can be added, for example, to the mixtures according to the invention in amounts of 0-10% by weight, are mentioned below.
(n = 1-12)
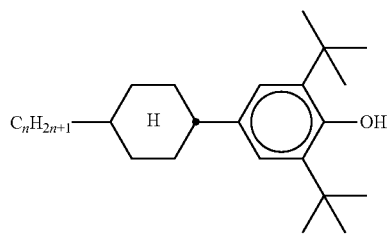
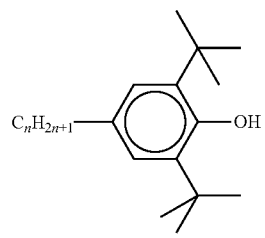
n = 1, 2, 3, 4, 5, 6 or 7
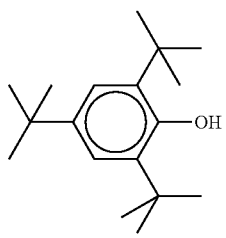
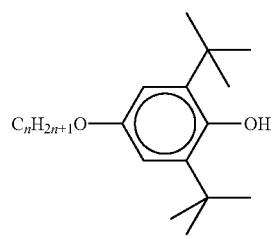
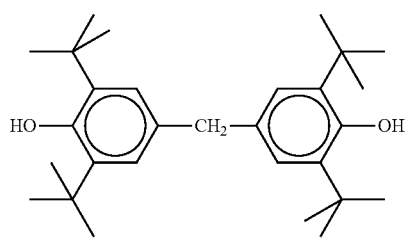
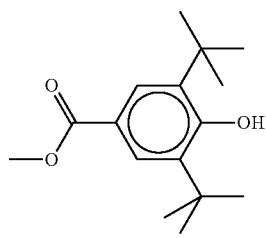

TABLE D-continued
Stabilisers, which can be added, for example, to the mixtures according to the invention in amounts of 0-10% by weight, are mentioned below.
(n = 1-12)
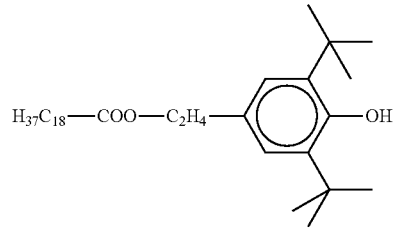
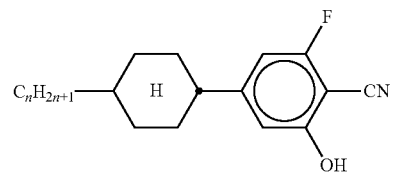
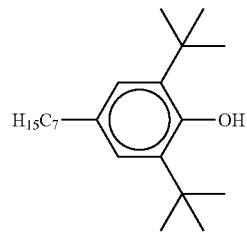
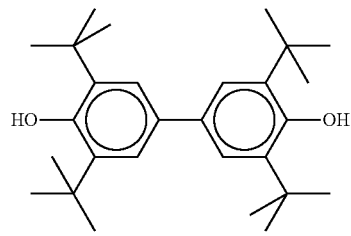
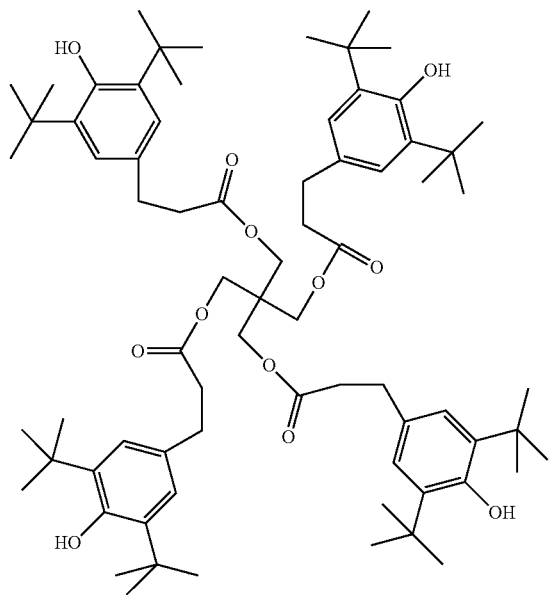 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]

TABLE D-continued
Stabilisers, which can be added, for example, to the mixtures according to the invention in amounts of 0-10% by weight, are mentioned below.
(n = 1-12)
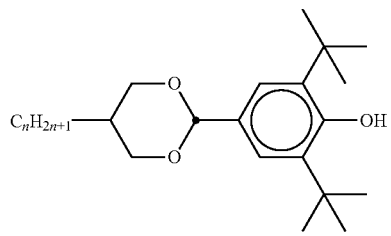
n = 1, 2, 3, 4, 5, 6 or 7
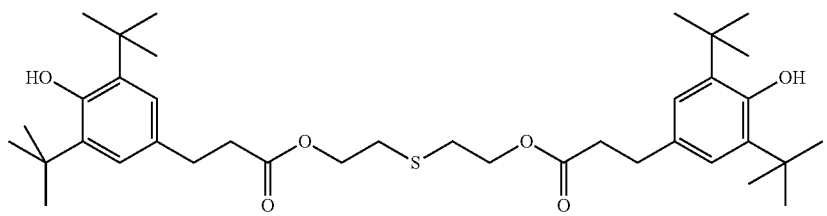 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
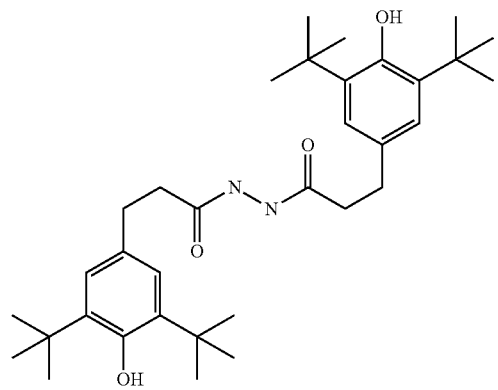 [SMILES: CC(C)(C)c1cc(CCC(=O)NNC(=O)CCc2cc(C(C)(C)C)c(O)c(C(C)(C)C)c2)cc(C(C)(C)C)c1O]
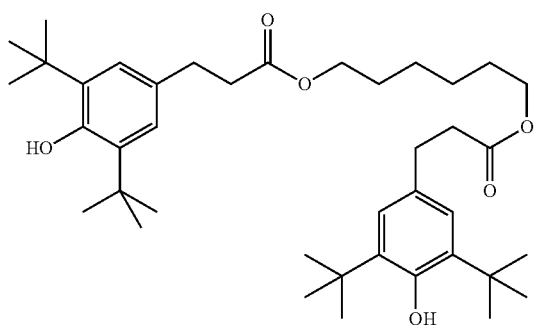 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
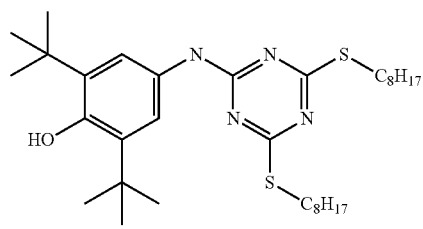

TABLE D-continued
Stabilisers, which can be added, for example, to the mixtures according to the invention in amounts of 0-10% by weight, are mentioned below.
(n = 1-12)
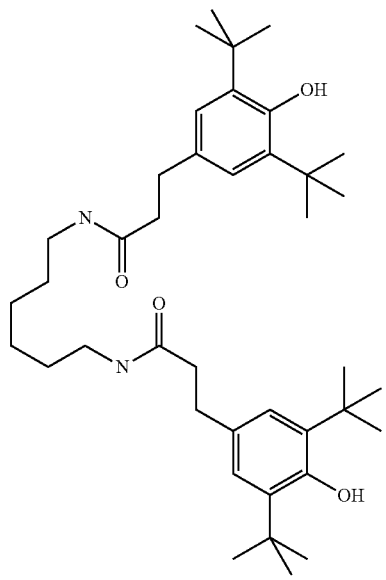 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
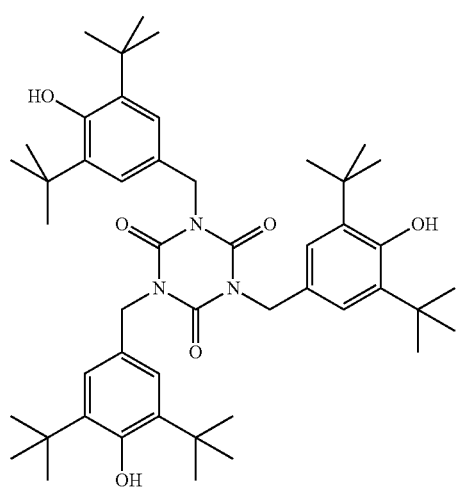 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
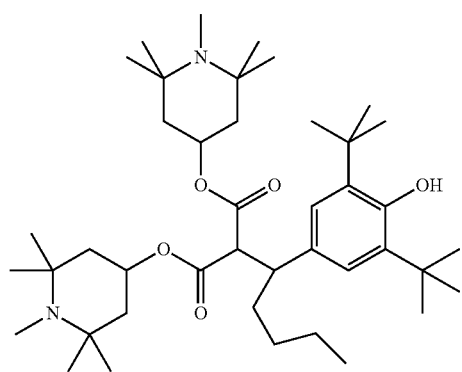 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]

TABLE D-continued
Stabilisers, which can be added, for example, to the mixtures according to the invention in amounts of 0-10% by weight, are mentioned below.
(n = 1-12)
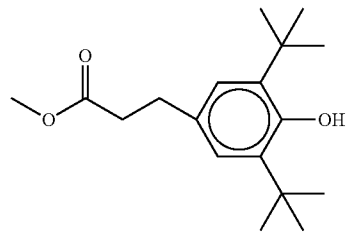
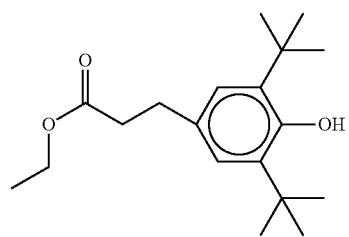
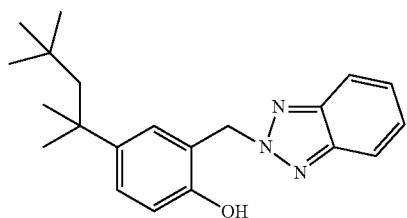 [SMILES: CC(C)(C)CC(C)(C)c1ccc(O)c(Cn2nc3ccccc3n2)c1]
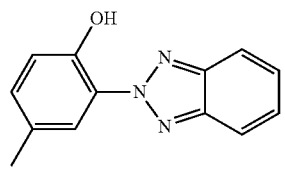 [SMILES: Cc1ccc(O)c(-n2nc3ccccc3n2)c1]
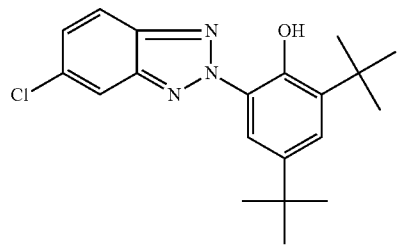 [SMILES: CC(C)(C)c1cc(-n2nc3ccc(Cl)cc3n2)c(O)c(C(C)(C)C)c1]
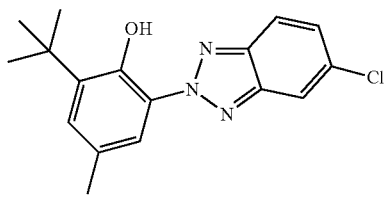 [SMILES: Cc1cc(-n2nc3ccc(Cl)cc3n2)c(O)c(C(C)(C)C)c1]

TABLE D-continued
Stabilisers, which can be added, for example, to the mixtures according to the invention in amounts of 0-10% by weight, are mentioned below.
(n = 1-12)
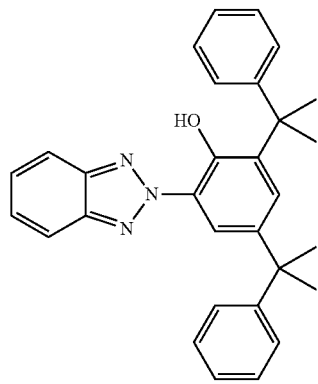 [SMILES: CC(C)(c1ccccc1)c1cc(-n2nc3ccccc3n2)c(O)c(C(C)(C)c2ccccc2)c1]
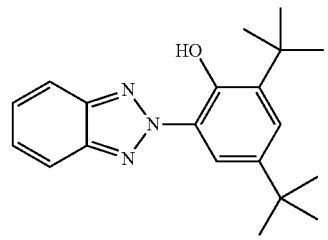 [SMILES: CC(C)(C)c1cc(-n2nc3ccccc3n2)c(O)c(C(C)(C)C)c1]
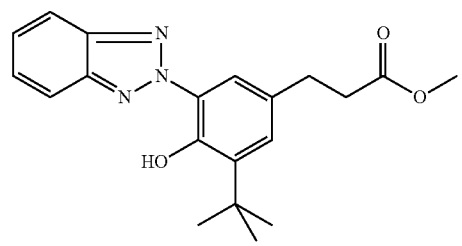 [SMILES: COC(=O)CCc1cc(-n2nc3ccccc3n2)c(O)c(C(C)(C)C)c1]
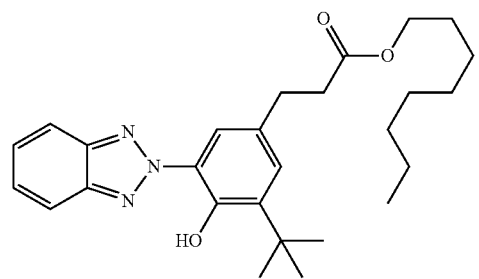 [SMILES: CCCCCCCCOC(=O)CCc1cc(-n2nc3ccccc3n2)c(O)c(C(C)(C)C)c1]

TABLE D-continued
Stabilisers, which can be added, for example, to the mixtures according to the invention in amounts of 0-10% by weight, are mentioned below.
(n = 1-12)
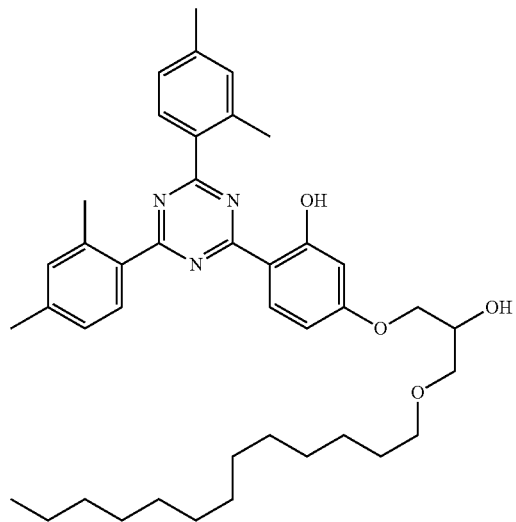 [SMILES: CCCCCCCCCCCCCOCC(O)COc1ccc(-c2nc(-c3ccc(C)cc3C)nc(-c3ccc(C)cc3C)n2)c(O)c1]
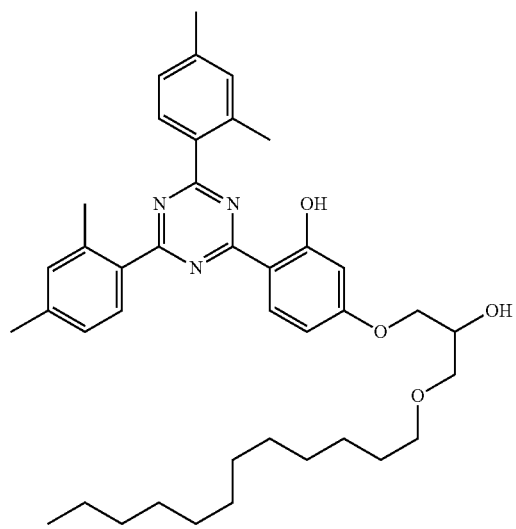 [SMILES: CCCCCCCCCCCCOCC(O)COc1ccc(-c2nc(-c3ccc(C)cc3C)nc(-c3ccc(C)cc3C)n2)c(O)c1]
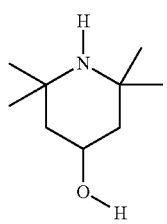
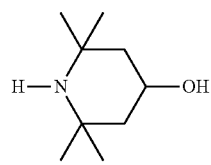

TABLE D-continued
Stabilisers, which can be added, for example, to the mixtures according to the invention in amounts of 0-10% by weight, are mentioned below.
(n = 1-12)
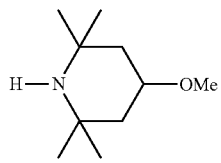
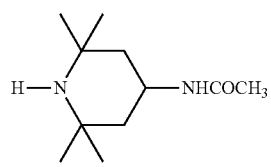
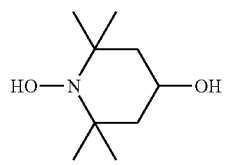
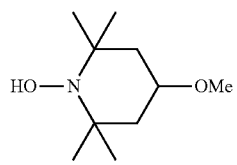
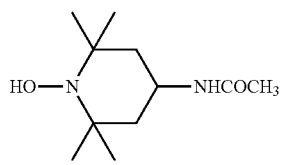
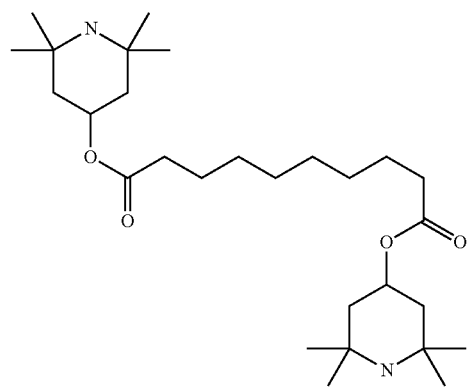

TABLE D-continued
Stabilisers, which can be added, for example, to the mixtures according to the invention in amounts of 0-10% by weight, are mentioned below.
(n = 1-12)
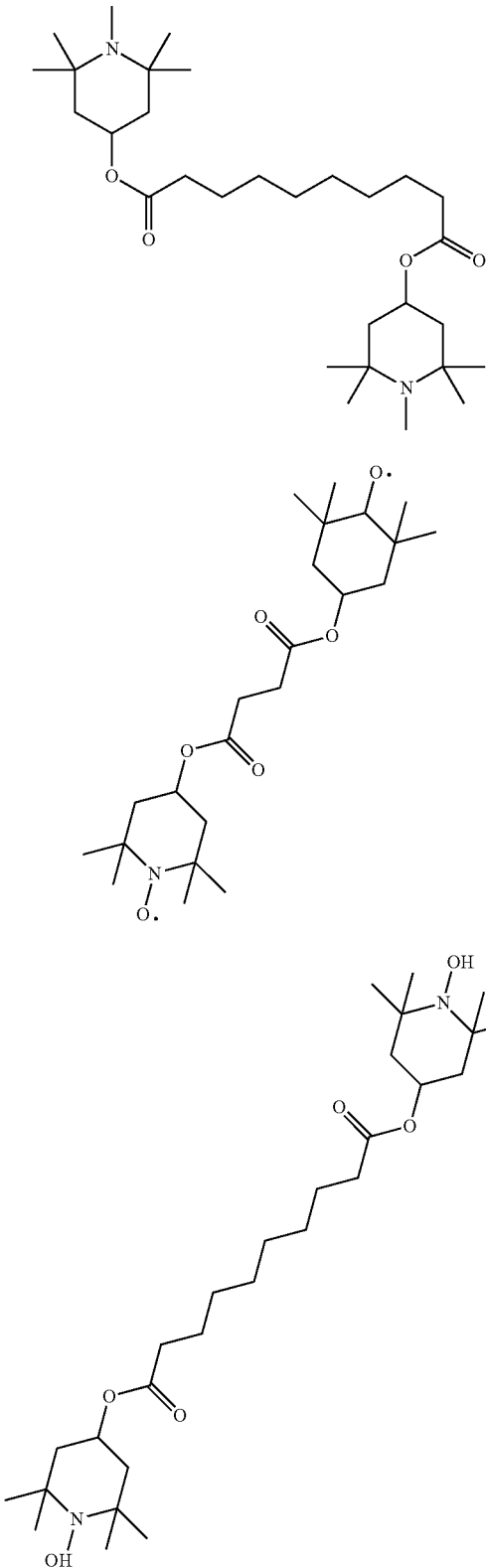

Suitable polymerisable compounds (reactive mesogens) for use in the mixtures according to the invention, preferably in PSA and PS-VA applications or PS-IPS/FFS applications, are mentioned below in Table E:
TABLE E
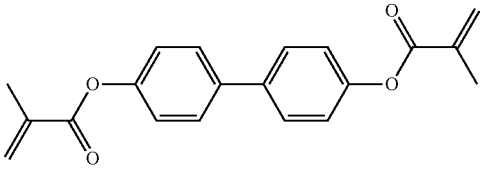 [SMILES: C=C(C)C(=O)Oc1ccc(-c2ccc(OC(=O)C(=C)C)cc2)cc1]
RM-1
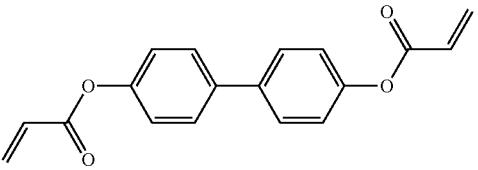 [SMILES: C=CC(=O)Oc1ccc(-c2ccc(OC(=O)C=C)cc2)cc1]
RM-2
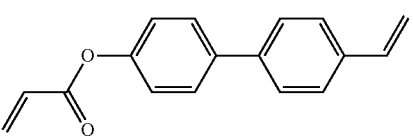 [SMILES: C=CC(=O)Oc1ccc(-c2ccc(C=C)cc2)cc1]
RM-3
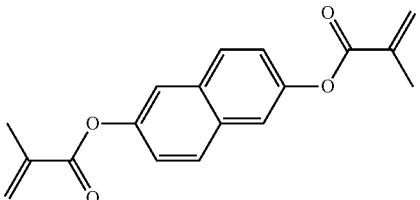
RM-4
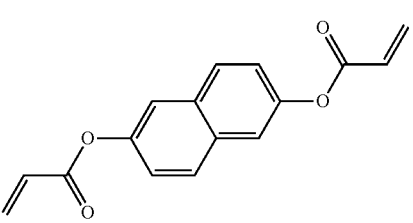 [SMILES: C=CC(=O)Oc1ccc2cc(OC(=O)C=C)ccc2c1]
RM-5
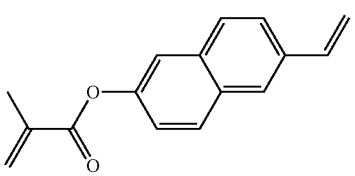 [SMILES: C=Cc1ccc2cc(OC(=O)C(=C)C)ccc2c1]
RM-6
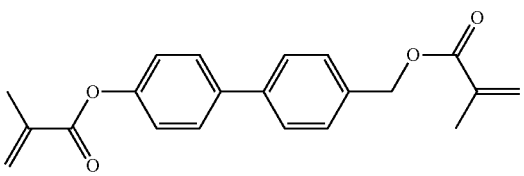 [SMILES: C=C(C)C(=O)OCc1ccc(-c2ccc(OC(=O)C(=C)C)cc2)cc1]
RM-7
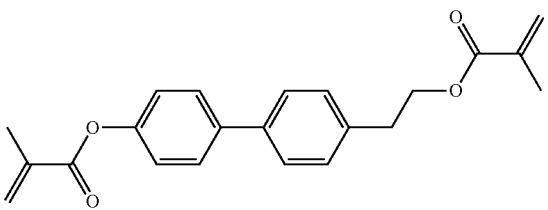
RM-8

TABLE E-continued
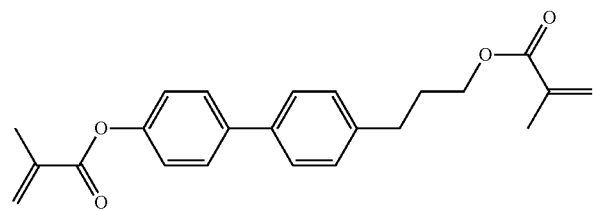 [SMILES: C=C(C)C(=O)OCCCc1ccc(-c2ccc(OC(=O)C(=C)C)cc2)cc1] RM-9
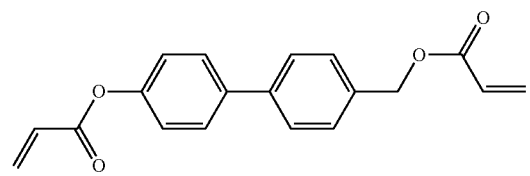 [SMILES: C=CC(=O)OCc1ccc(-c2ccc(OC(=O)C=C)cc2)cc1] RM-10
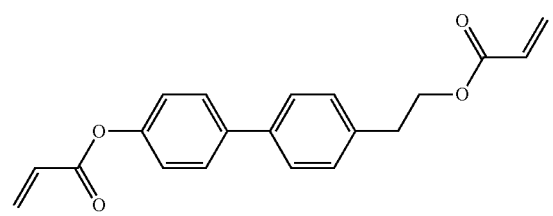 [SMILES: C=CC(=O)OCCc1ccc(-c2ccc(OC(=O)C=C)cc2)cc1] RM-11
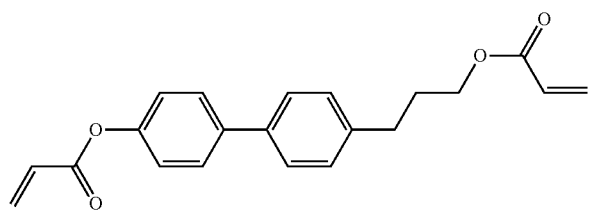 [SMILES: C=CC(=O)OCCCc1ccc(-c2ccc(OC(=O)C=C)cc2)cc1] RM-12
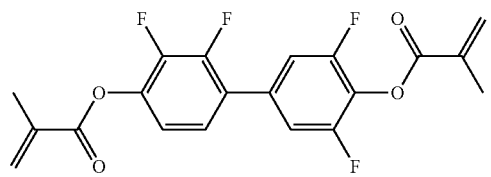 [SMILES: C=C(C)C(=O)Oc1ccc(-c2cc(F)c(OC(=O)C(=C)C)c(F)c2)c(F)c1F] RM-13
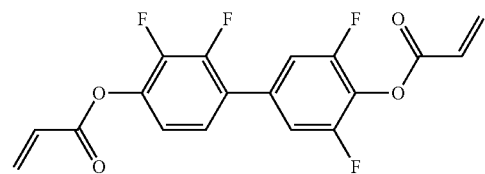 [SMILES: C=CC(=O)Oc1ccc(-c2cc(F)c(OC(=O)C=C)c(F)c2)c(F)c1F] RM-14
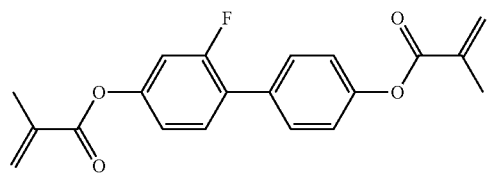 [SMILES: C=C(C)C(=O)Oc1ccc(-c2ccc(OC(=O)C(=C)C)cc2F)cc1] RM-15
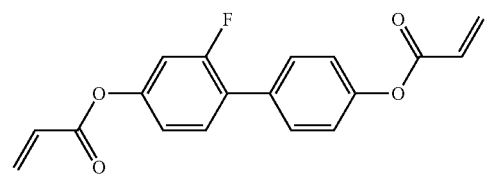 RM-16

TABLE E-continued
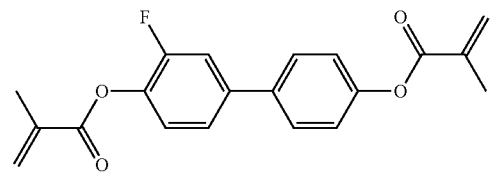 [SMILES: C=C(C)C(=O)Oc1ccc(-c2ccc(OC(=O)C(=C)C)c(F)c2)cc1] RM-17
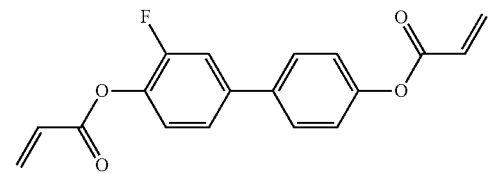 [SMILES: C=CC(=O)Oc1ccc(-c2ccc(OC(=O)C=C)c(F)c2)cc1] RM-18
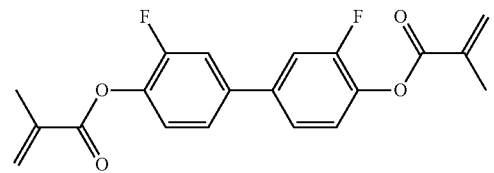 [SMILES: C=C(C)C(=O)Oc1ccc(-c2ccc(OC(=O)C(=C)C)c(F)c2)cc1F] RM-19
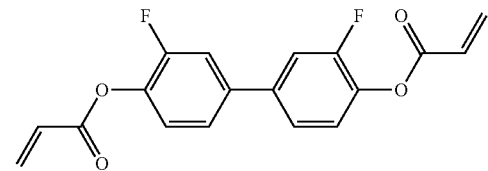 [SMILES: C=CC(=O)Oc1ccc(-c2ccc(OC(=O)C=C)c(F)c2)cc1F] RM-20
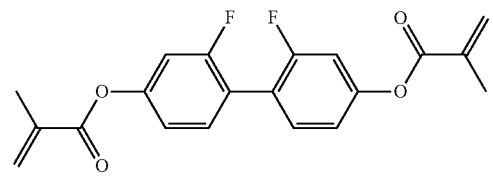 [SMILES: C=C(C)C(=O)Oc1ccc(-c2ccc(OC(=O)C(=C)C)cc2F)c(F)c1] RM-21
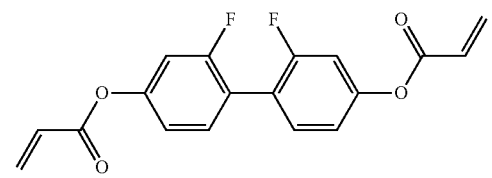 [SMILES: C=CC(=O)Oc1ccc(-c2ccc(OC(=O)C=C)cc2F)c(F)c1] RM-22
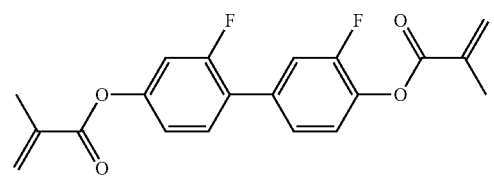 [SMILES: C=C(C)C(=O)Oc1ccc(-c2ccc(OC(=O)C(=C)C)c(F)c2)c(F)c1] RM-23
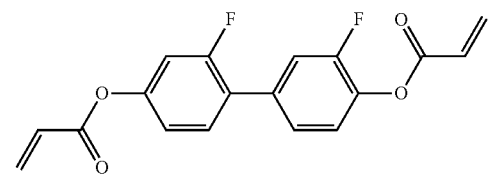 [SMILES: C=CC(=O)Oc1ccc(-c2ccc(OC(=O)C=C)c(F)c2)c(F)c1] RM-24
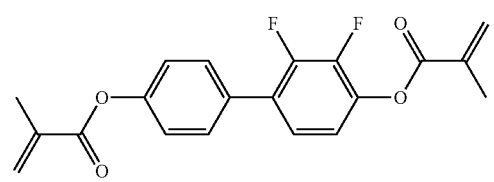 [SMILES: C=C(C)C(=O)Oc1ccc(-c2ccc(OC(=O)C(=C)C)c(F)c2F)cc1] RM-25

TABLE E-continued
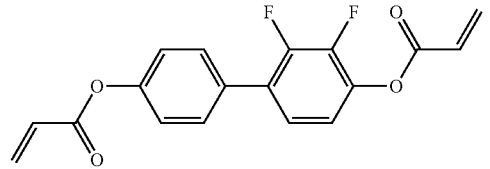 [SMILES: C=CC(=O)Oc1ccc(-c2ccc(OC(=O)C=C)c(F)c2F)cc1] RM-26
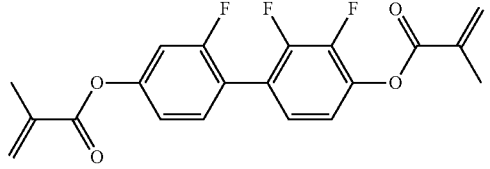 [SMILES: C=C(C)C(=O)Oc1ccc(-c2ccc(OC(=O)C(=C)C)c(F)c2F)c(F)c1] RM-27
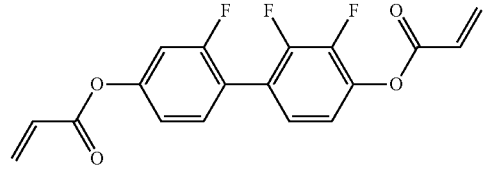 [SMILES: C=CC(=O)Oc1ccc(-c2ccc(OC(=O)C=C)c(F)c2F)c(F)c1] RM-28
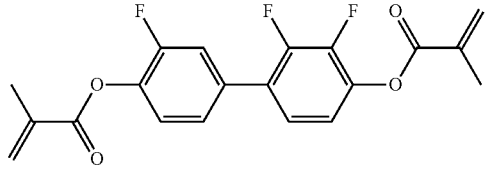 [SMILES: C=C(C)C(=O)Oc1ccc(-c2ccc(OC(=O)C(=C)C)c(F)c2F)cc1F] RM-29
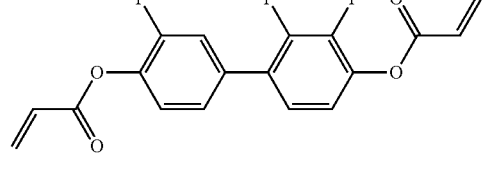 RM-30
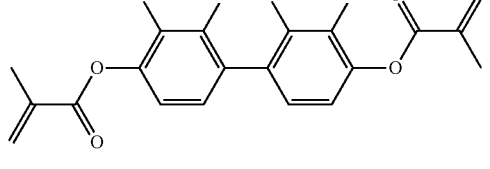 RM-31
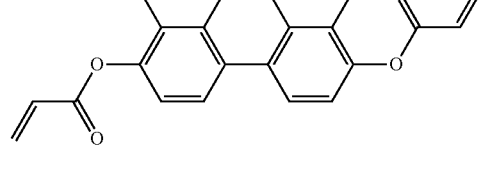 RM-32
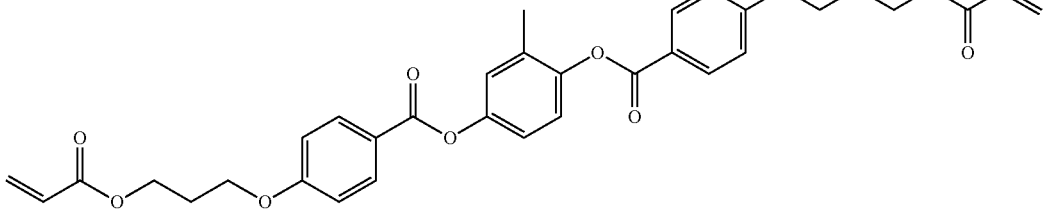 RM-33

TABLE E-continued
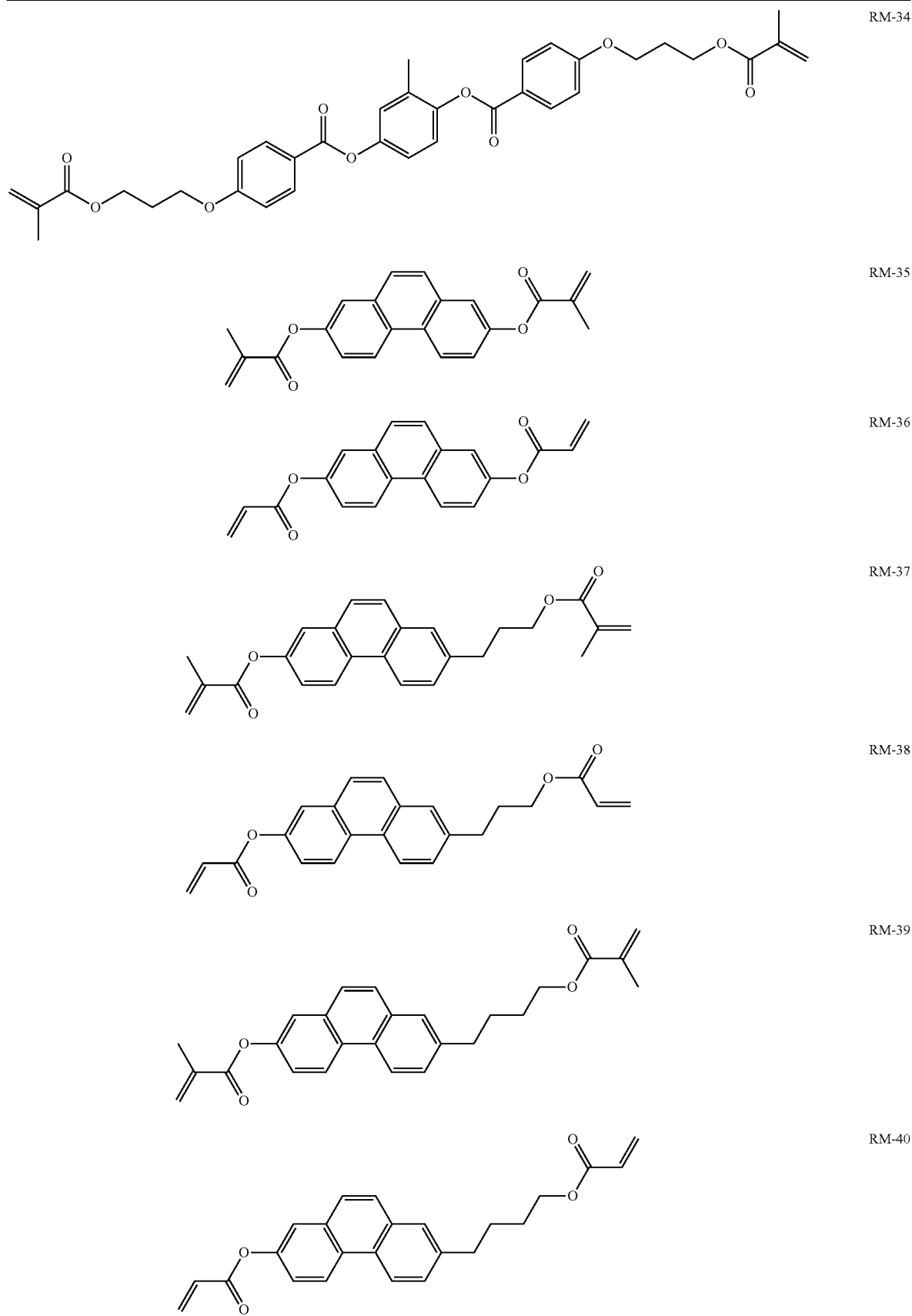
RM-34
RM-35
RM-36
RM-37
RM-38
RM-39
RM-40

TABLE E-continued
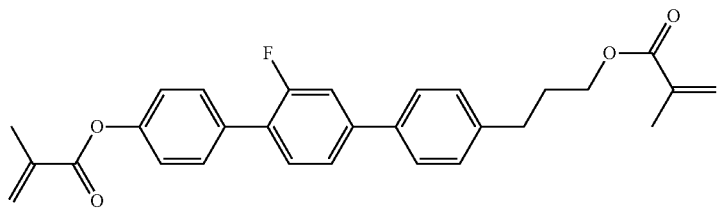 [SMILES: C=C(C)C(=O)OCCCc1ccc(-c2ccc(-c3ccc(OC(=O)C(=C)C)cc3)c(F)c2)cc1]
RM-41
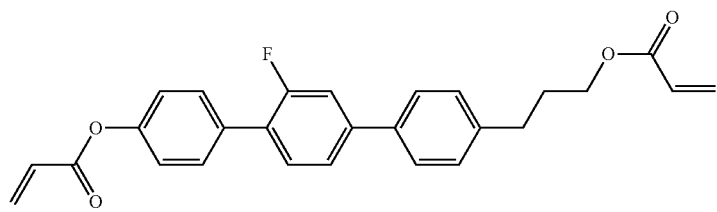 [SMILES: C=CC(=O)OCCCc1ccc(-c2ccc(-c3ccc(OC(=O)C=C)cc3)c(F)c2)cc1]
RM-42
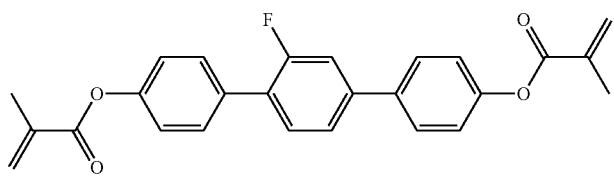 [SMILES: C=C(C)C(=O)Oc1ccc(-c2ccc(-c3ccc(OC(=O)C(=C)C)cc3)c(F)c2)cc1]
RM-43
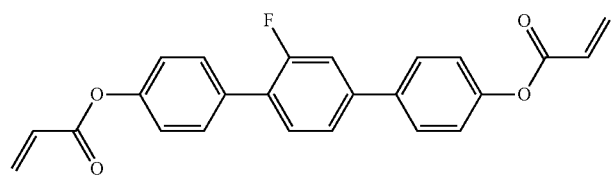 [SMILES: C=CC(=O)Oc1ccc(-c2ccc(-c3ccc(OC(=O)C=C)cc3)c(F)c2)cc1]
RM-44
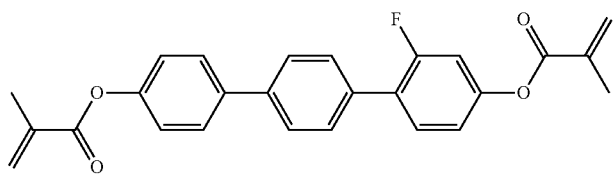 [SMILES: C=C(C)C(=O)Oc1ccc(-c2ccc(-c3ccc(OC(=O)C(=C)C)cc3F)cc2)cc1]
RM-45
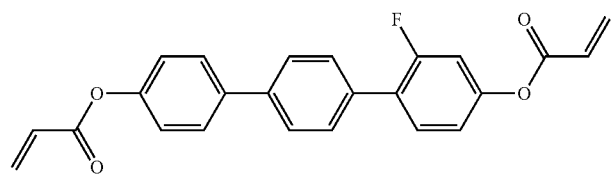 [SMILES: C=CC(=O)Oc1ccc(-c2ccc(-c3ccc(OC(=O)C=C)cc3F)cc2)cc1]
RM-46
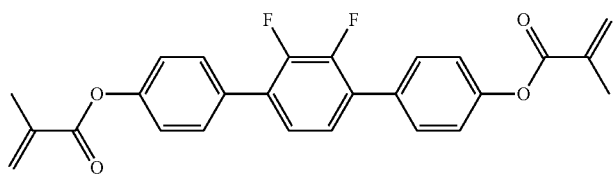 [SMILES: C=C(C)C(=O)Oc1ccc(-c2ccc(-c3ccc(OC(=O)C(=C)C)cc3)c(F)c2F)cc1]
RM-47
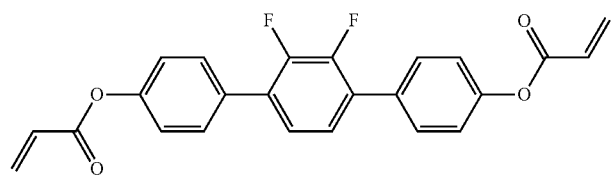 [SMILES: C=CC(=O)Oc1ccc(-c2ccc(-c3ccc(OC(=O)C=C)cc3)c(F)c2F)cc1]
RM-48

TABLE E-continued
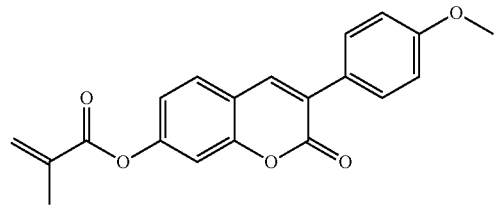 [SMILES: C=C(C)C(=O)Oc1ccc2cc(-c3ccc(OC)cc3)c(=O)oc2c1] RM-49
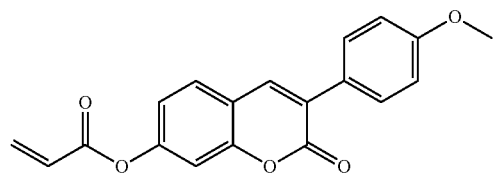 [SMILES: C=CC(=O)Oc1ccc2cc(-c3ccc(OC)cc3)c(=O)oc2c1] RM-50
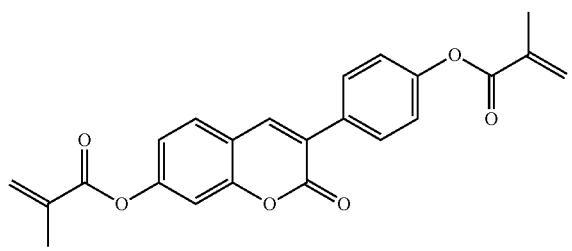 [SMILES: C=C(C)C(=O)Oc1ccc(-c2cc3ccc(OC(=O)C(=C)C)cc3oc2=O)cc1] RM-51
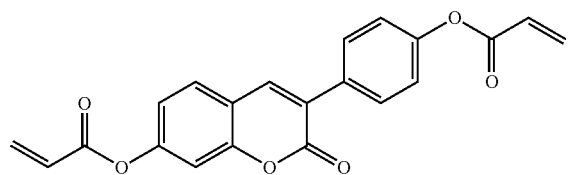 [SMILES: C=CC(=O)Oc1ccc(-c2cc3ccc(OC(=O)C=C)cc3oc2=O)cc1] RM-52
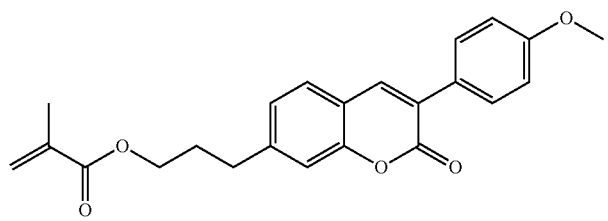 [SMILES: C=C(C)C(=O)OCCCc1ccc2cc(-c3ccc(OC)cc3)c(=O)oc2c1] RM-53
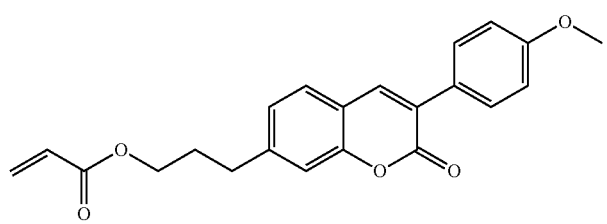 [SMILES: C=CC(=O)OCCCc1ccc2cc(-c3ccc(OC)cc3)c(=O)oc2c1] RM-54
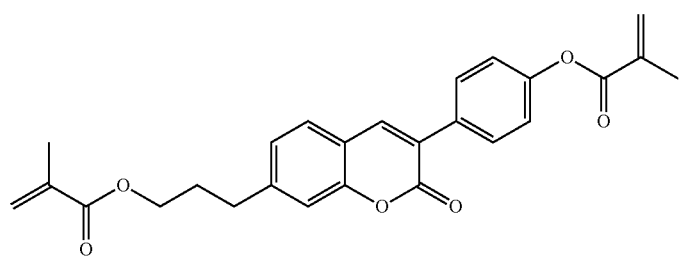 [SMILES: C=C(C)C(=O)OCCCc1ccc2cc(-c3ccc(OC(=O)C(=C)C)cc3)c(=O)oc2c1] RM-55

TABLE E-continued
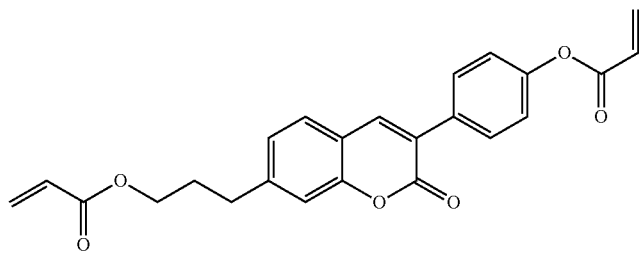 [SMILES: C=CC(=O)OCCCc1ccc2cc(-c3ccc(OC(=O)C=C)cc3)c(=O)oc2c1]
RM-56
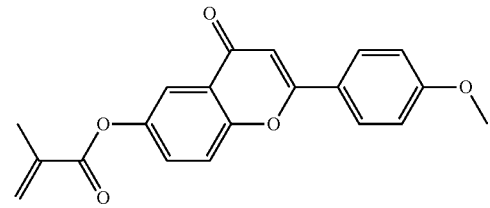 [SMILES: C=C(C)C(=O)Oc1ccc2oc(-c3ccc(OC)cc3)cc(=O)c2c1]
RM-57
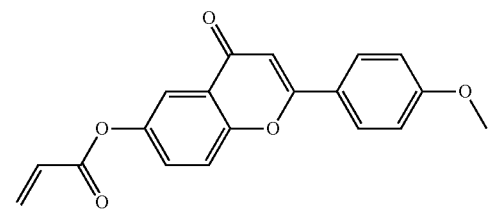 [SMILES: C=CC(=O)Oc1ccc2oc(-c3ccc(OC)cc3)cc(=O)c2c1]
RM-58
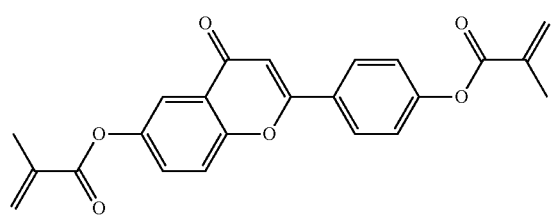 [SMILES: C=C(C)C(=O)Oc1ccc(-c2cc(=O)c3cc(OC(=O)C(=C)C)ccc3o2)cc1]
RM-59
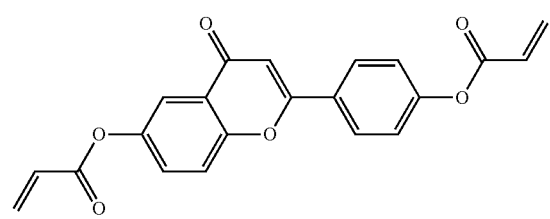 [SMILES: C=CC(=O)Oc1ccc(-c2cc(=O)c3cc(OC(=O)C=C)ccc3o2)cc1]
RM-60
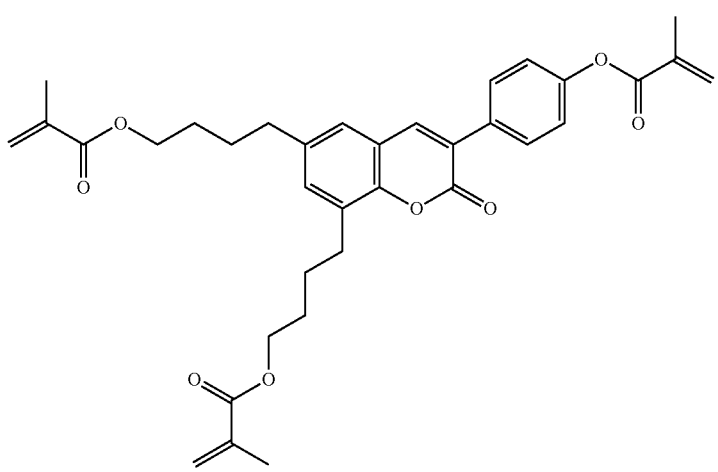 [SMILES: C=C(C)C(=O)OCCCCc1cc(CCCCOC(=O)C(=C)C)c2oc(=O)c(-c3ccc(OC(=O)C(=C)C)cc3)cc2c1]
RM-61

TABLE E-continued
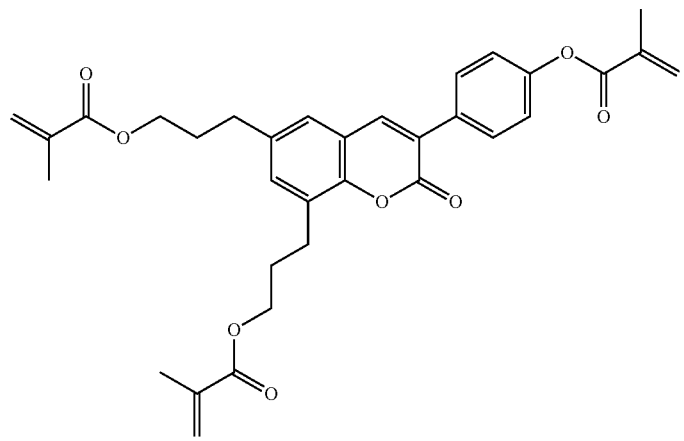 [SMILES: C=C(C)C(=O)OCCCc1cc(CCCOC(=O)C(=C)C)c2oc(=O)c(-c3ccc(OC(=O)C(=C)C)cc3)cc2c1]
RM-62
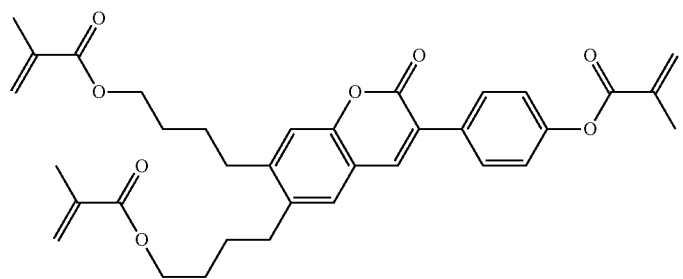 [SMILES: C=C(C)C(=O)OCCCCc1cc2cc(-c3ccc(OC(=O)C(=C)C)cc3)c(=O)oc2cc1CCCCOC(=O)C(=C)C]
RM-63
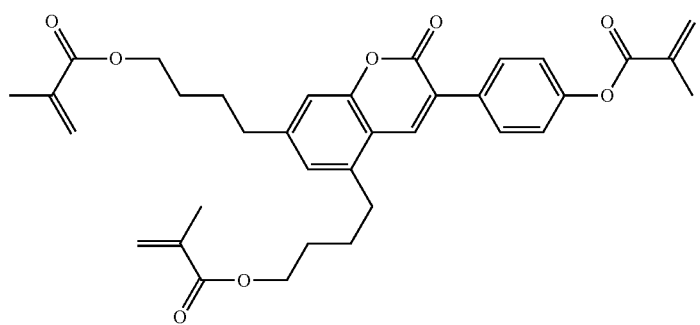 [SMILES: C=C(C)C(=O)OCCCCc1cc(CCCCOC(=O)C(=C)C)c2cc(-c3ccc(OC(=O)C(=C)C)cc3)c(=O)oc2c1]
RM-64
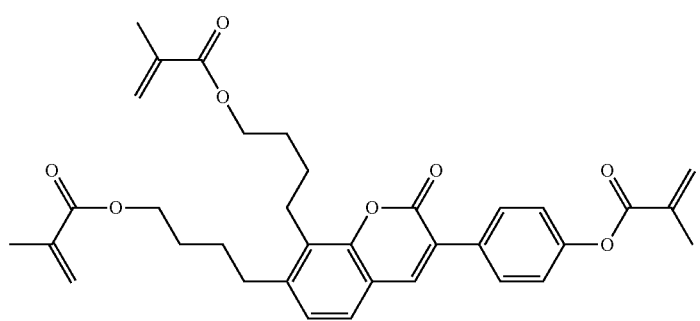 [SMILES: C=C(C)C(=O)OCCCCc1ccc2cc(-c3ccc(OC(=O)C(=C)C)cc3)c(=O)oc2c1CCCCOC(=O)C(=C)C]
RM-65

TABLE E-continued
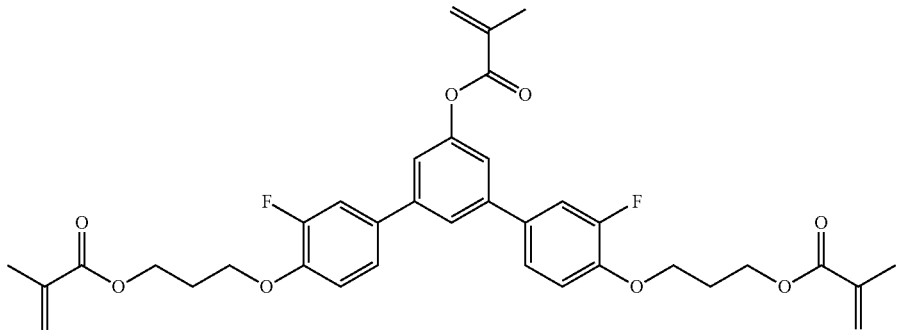 [SMILES: C=C(C)C(=O)OCCCOc1ccc(-c2cc(OC(=O)C(=C)C)cc(-c3ccc(OCCCOC(=O)C(=C)C)c(F)c3)c2)cc1F]
RM-66
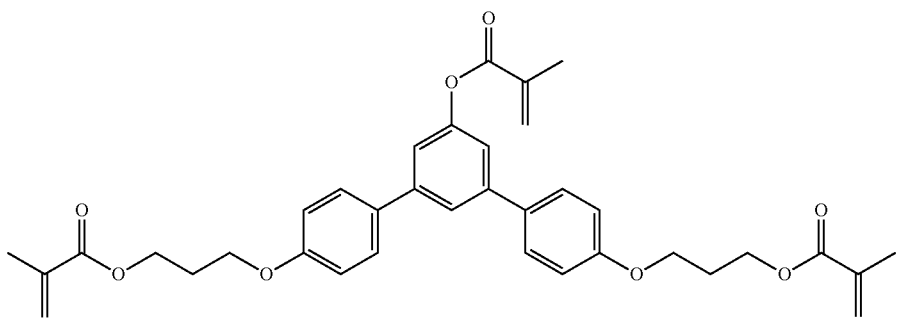 [SMILES: C=C(C)C(=O)OCCCOc1ccc(-c2cc(OC(=O)C(=C)C)cc(-c3ccc(OCCCOC(=O)C(=C)C)cc3)c2)cc1]
RM-67
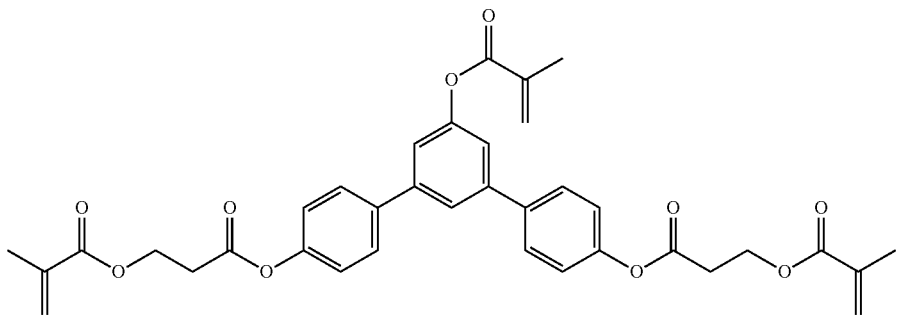 [SMILES: C=C(C)C(=O)OCCC(=O)Oc1ccc(-c2cc(OC(=O)C(=C)C)cc(-c3ccc(OC(=O)CCOC(=O)C(=C)C)cc3)c2)cc1]
RM-68
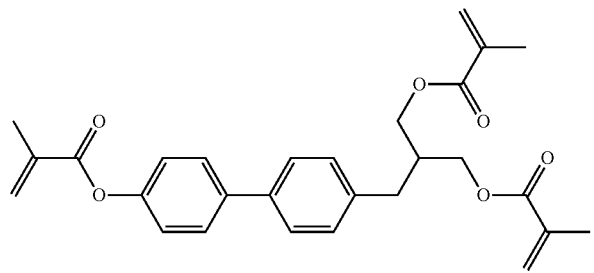 [SMILES: C=C(C)C(=O)OCC(COC(=O)C(=C)C)Cc1ccc(-c2ccc(OC(=O)C(=C)C)cc2)cc1]
RM-69
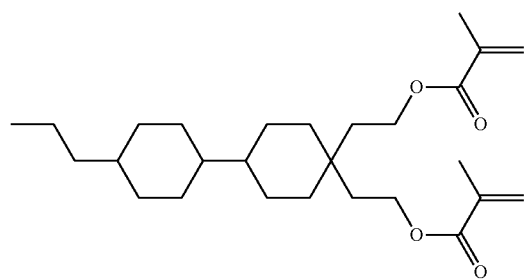 [SMILES: C=C(C)C(=O)OCCC1(CCOC(=O)C(=C)C)CCC(C2CCC(CCC)CC2)CC1]
RM-70

TABLE E-continued
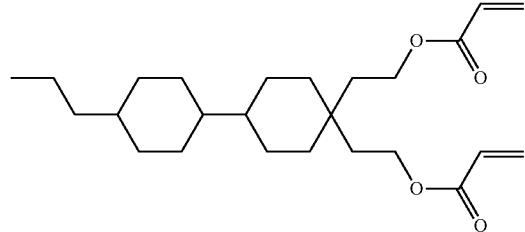 [SMILES: C=CC(=O)OCCC1(CCOC(=O)C=C)CCC(C2CCC(CCC)CC2)CC1]
RM-71
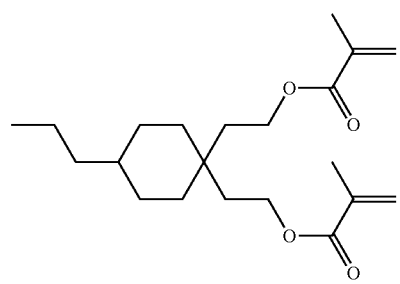 [SMILES: C=C(C)C(=O)OCCC1(CCOC(=O)C(=C)C)CCC(CCC)CC1]
RM-72
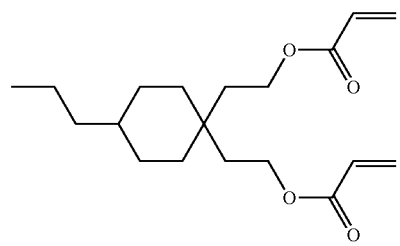 [SMILES: C=CC(=O)OCCC1(CCOC(=O)C=C)CCC(CCC)CC1]
RM-73
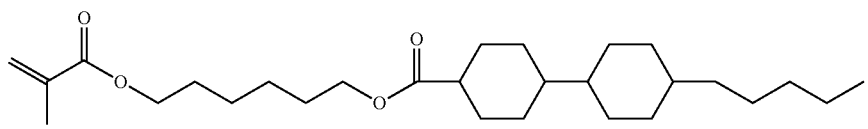 [SMILES: C=C(C)C(=O)OCCCCCCOC(=O)C1CCC(C2CCC(CCCCC)CC2)CC1]
RM-74
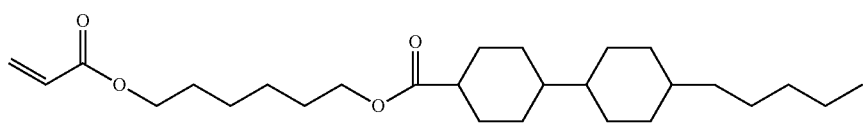
RM-75
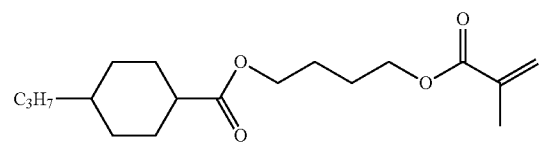
RM-76
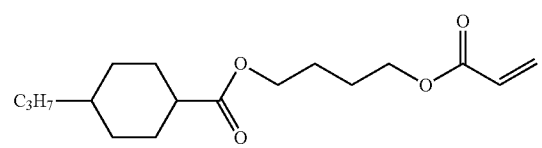
RM-77

TABLE E-continued
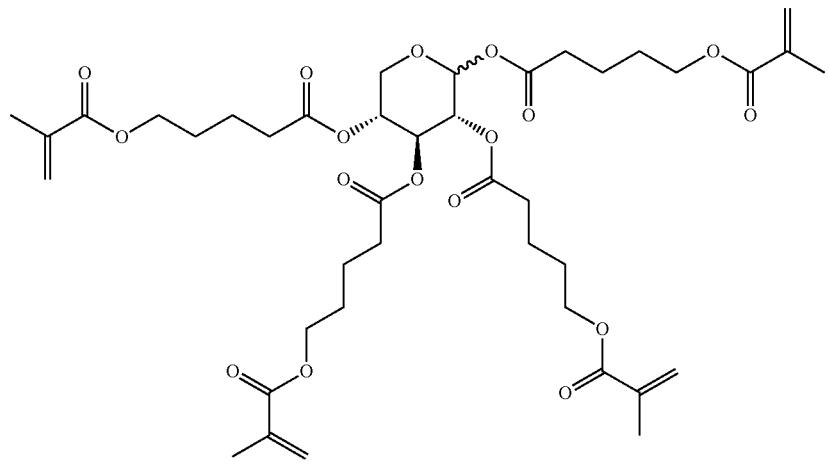 [SMILES: C=C(C)C(=O)OCCCCC(=O)OC1OC[C@@H](OC(=O)CCCCOC(=O)C(=C)C)[C@H](OC(=O)CCCCOC(=O)C(=C)C)[C@H]1OC(=O)CCCCOC(=O)C(=C)C]
RM-78
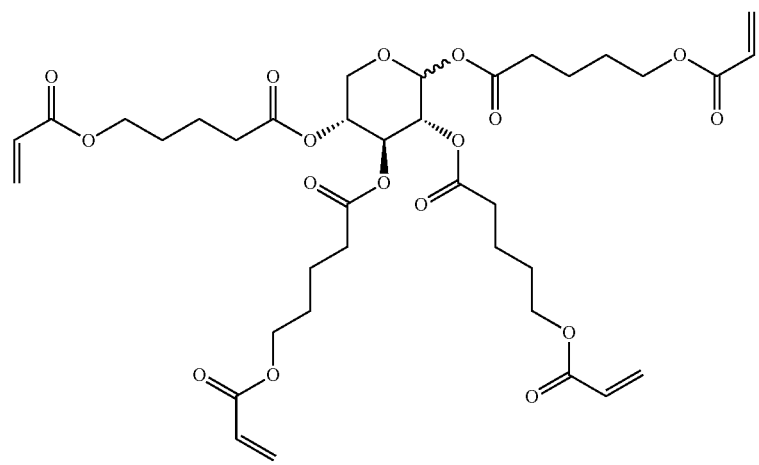 [SMILES: C=CC(=O)OCCCCC(=O)OC1OC[C@@H](OC(=O)CCCCOC(=O)C=C)[C@H](OC(=O)CCCCOC(=O)C=C)[C@H]1OC(=O)CCCCOC(=O)C=C]
RM-79
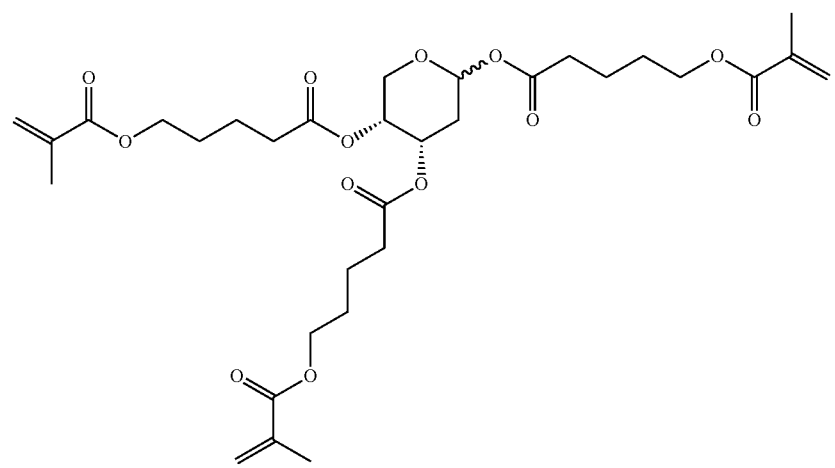 [SMILES: C=C(C)C(=O)OCCCCC(=O)OC1C[C@H](OC(=O)CCCCOC(=O)C(=C)C)[C@H](OC(=O)CCCCOC(=O)C(=C)C)CO1]
RM-80

TABLE E-continued

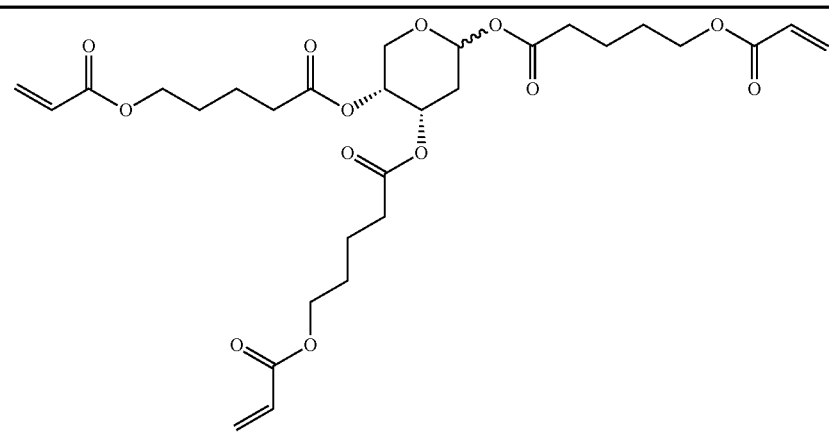
RM-81

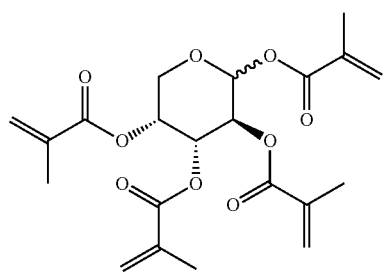 [SMILES: C=C(C)C(=O)OC1OC[C@@H](OC(=O)C(=C)C)[C@@H](OC(=O)C(=C)C)[C@@H]1OC(=O)C(=C)C]
RM-82

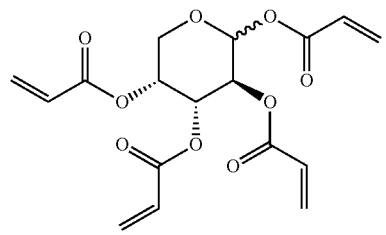 [SMILES: C=CC(=O)OC1OC[C@@H](OC(=O)C=C)[C@@H](OC(=O)C=C)[C@@H]1OC(=O)C=C]
RM-83

Table E shows example compounds which can preferably be used in the mixtures according to the invention as polymerisable compounds (reactive mesogenic compounds) for the preparation, for example, of PSV, PS-VA, PS-IPS or PS-FFS mixtures.

If the mixtures according to the invention comprise one or more mesogenic compounds, the mesogenic compound in a preferred embodiment is a compound selected from Table E.

The following examples are intended to explain the invention without limiting it.

EXAMPLES

Above and below, percentage data denote percent by weight. All temperatures are indicated in degrees Celsius. m.p. denotes melting point, cl.p.=clearing point. Furthermore, C=crystalline state, N=nematic phase, S=smectic phase and I=isotropic phase. The data between these symbols represent the transition temperatures. Furthermore, Δn denotes the optical anisotropy at 589 nm and 20° C.,
$\gamma_1$ denotes the rotational viscosity (mPa·s) at 20° C.,
Δ∈ denotes the dielectric anisotropy at 20° C. and 1 kHz (Δ∈=∈$_\parallel$-∈$_\perp$, where ∈$_\parallel$ denotes the dielectric constant parallel to the longitudinal axes of the molecules and ∈$_\perp$ denotes the dielectric constant perpendicular thereto),
$V_{10}$ denotes the voltage (V) for 10% transmission (viewing angle perpendicular to the plate surface), (threshold voltage), determined in a TN cell (90 degree twist) at the 1st minimum (i.e. at a dΔn value of 0.5 µm) at 20° C.,
$V_0$ denotes the capacitively determined Freedericks threshold voltage in an antiparallel-rubbed cell at 20° C.

All physical properties are determined in accordance with "Merck Liquid Crystals, Physical Properties of Liquid Crystals", status November 1997, Merck KGaA, Germany, and apply for a temperature of 20° C., unless explicitly indicated otherwise.

Example 1

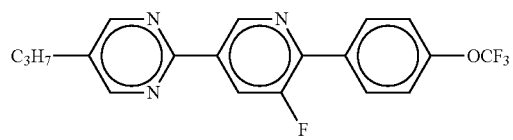

Step 1

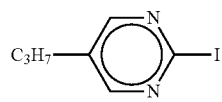

150 ml of 57% hydroiodic acid are added at 0° C. to 160 mmol of 2-chloro-5-propylpyrimidine, and the mixture is stirred at 0° C. for 1 hour. The mixture is then neutralised at 0° C. using soda solution, and sodium sulfite solution is added for decolorisation. The batch is extracted with methyl tert-butyl ether, and the organic phase is washed with water, dried using sodium sulfate and evaporated. The residue is chromatographed on silica gel with dichloromethane.
Step 2

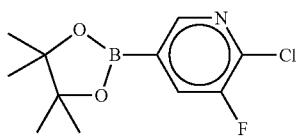

190 mmol of 5-bromo-2-chloro-3-fluoropyridine and 190 mmol of bis-pinacolatodiboron are dissolved in 500 ml of dioxane, and 580 mmol of potassium acetate and 6 mmol of Pd(DPPF)Cl$_2$ are added. The mixture is heated at 100° C. for 17 hours with stirring. Water and methyl tert-butyl ether are added to the reaction solution, and the organic phase is washed with saturated NaCl solution, dried using sodium sulfate and evaporated. The residue is purified by chromatography on silica gel with dichloromethane/MTB ether 95/5, giving 2-chloro-3-fluoro-5-(4,4,5,5-tetraethyl-1,3,2-dioxaborolan-2-yl)pyridine.
Step 3

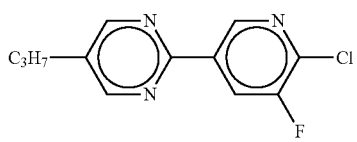

65 mmol of 2-iodo-5-propylpyrimidine and 65 mmol of 2-chloro-3-fluoro-5-(4,4,5,5-tetraethyl-1,3,2-dioxaborolan-2-yl)pyridine are dissolved in 155 ml of dioxane, and 130 mmol of tripotassium phosphate and 2 mmol of tetrakis(triphenylphosphine)palladium catalyst are added. The mixture is heated at 100° C. for 17 hours with stirring. Water and methyl tert-butyl ether are added to the reaction solution, and the organic phase is washed with water, dried using sodium sulfate and evaporated. The residue is purified by chromatography on silica gel with dichloromethane/MTB ether 90/10, giving 2-(6-chloro-5-fluoropyridin-3-yl)-5-propylpyrimidine.
Step 4

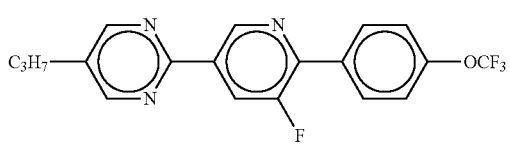

10.2 mmol of 2-(6-chloro-5-fluoropyridin-3-yl)-5-propylpyrimidine and 10.2 mmol of 4,4,5,5-tetramethyl-2-(4-trifluoromethoxyphenyl)-1,3,2-dioxaborolane are dissolved in 30 ml of dioxane, and 20.4 mmol of caesium fluoride and 0.5 mmol of bis(tricyclohexylphosphine)palladium dichloride catalyst are added. The mixture is heated at 100° C. for 18 hours with stirring. Water and MTB ether are added to the batch, and the organic phase is washed with water, dried using sodium sulfate and evaporated. The residue is purified by chromatography on silica gel with heptane/MTB ether 2/1 and recrystallised from isopropanol, giving 2-[5-fluoro-6-(4-trifluoromethoxyphenyl)pyridin-3-yl]-5-propylpyrimidine.

C 108 S$_A$ 173 I; Δn=0.238; Δε=30.5; γ$_1$=83

The following compounds of the formula

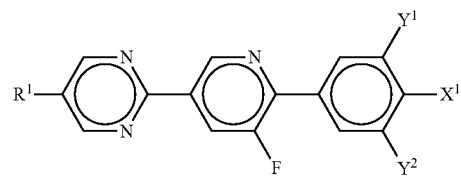

are prepared analogously:

| R$^1$ | X$^1$ | Y$^1$ | Y$^2$ |
|---|---|---|---|
| CH$_3$ | OCF$_3$ | H | H |
| C$_2$H$_5$ | OCF$_3$ | H | H |
| n-C$_4$H$_9$ | OCF$_3$ | H | H |
| n-C$_5$H$_{11}$ | OCF$_3$ | H | H |
| CH$_3$ | OCF$_3$ | F | H |
| C$_2$H$_5$ | OCF$_3$ | F | H |
| n-C$_3$H$_7$ | OCF$_3$ | F | H |
| n-C$_4$H$_9$ | OCF$_3$ | F | H |
| n-C$_5$H$_{11}$ | OCF$_3$ | F | H |
| n-C$_5$H$_{11}$ | OCF$_3$ | F | H |
| CH$_3$ | OCF$_3$ | F | F |
| C$_2$H$_5$ | OCF$_3$ | F | F |
| n-C$_3$H$_7$ | OCF$_3$ | F | F |
| n-C$_4$H$_9$ | OCF$_3$ | F | F |
| n-C$_5$H$_{11}$ | OCF$_3$ | F | F |
| CH$_3$ | F | H | H |
| C$_2$H$_5$ | F | H | H |
| n-C$_3$H$_7$ | F | H | H |
| n-C$_4$H$_9$ | F | H | H |
| n-C$_3$H$_7$ | F | H | H |
| n-C$_3$H$_7$ | F | F | H |
| n-C$_5$H$_{11}$ | F | F | F |
| n-C$_3$H$_7$ | CN | F | H |
| n-C$_5$H$_{11}$ | Cl | H | H |
| n-C$_5$H$_{11}$ | OCHF$_2$ | H | H |

MIXTURE EXAMPLES

Example M1

| | | | |
|---|---|---|---|
| PUQU-3-F | 7.0% | Clearing point [° C.]: | 69.0 |
| CC-3-V1 | 7.0% | Δn [589 nm, 20° C.]: | 0.1001 |
| CC-3-V | 48.0% | Δε [1 kHz, 20° C.]: | 3.0 |
| CCP-V-1 | 13.5% | ε$_∥$ [1 kHz, 20° C.]: | 5.6 |

-continued

| | | | |
|---|---|---|---|
| PP-1-2V1 | 6.5% | $\epsilon_\perp$ [1 kHz, 20° C.]: | 2.6 |
| PGP-2-3 | 4.0% | $K_3$ [pN, 20° C.]: | 13.0 |
| PGP-2-4 | 5.0% | $K_3/K_1$ [20° C.]: | 1.02 |
| CCP-30CF3 | 4.0% | $\gamma_1$ [mPa·s, 20° C.]: | 42 |
| | 5.0% | $V_0$ [V]: | 2.23 |

Example M2

| | | | |
|---|---|---|---|
| PGP-2-3 | 2.0% | Clearing point [° C.]: | 74.5 |
| PGP-2-4 | 5.0% | $\Delta n$ [589 nm, 20° C.]: | 0.1030 |
| CCP-V-1 | 9.0% | $\Delta\epsilon$ [1 kHz, 20° C.]: | 7.0 |
| CC-3-V | 48.0% | $\epsilon_\parallel$ [1 kHz, 20° C.]: | 10.1 |
| CC-3-V1 | 8.0% | $\epsilon_\perp$ [1 kHz, 20° C.]: | 3.1 |
| PUQU-3-F | 6.0% | $K_3$ [pN, 20° C.]: | 13.3 |
| APUQU-2-F | 7.0% | $K_3/K_1$ [20° C.]: | 0.99 |
| APUQU-3-F | 7.0% | $\gamma_1$ [mPa·s, 20° C.]: | 50 |
| | 8.0% | $V_0$ [V]: | 1.46 |

Example M3

| | | | |
|---|---|---|---|
| CC-3-V | 41.0% | Clearing point [° C.]: | 75.0 |
| CC-3-V1 | 8.0% | $\Delta n$ [589 nm, 20° C.]: | 0.1321 |
| CCP-V2-1 | 3.0% | $\Delta\epsilon$ [1 kHz, 20° C.]: | 4.4 |
| CPGU-3-OT | 6.0% | $\epsilon_\parallel$ [1 kHz, 20° C.]: | 7.2 |
| PGP-2-2V | 18.0% | $\epsilon_\perp$ [1 kHz, 20° C.]: | 2.8 |
| PP-1-2V1 | 10.5% | $\gamma_1$ [mPa·s, 20° C.]: | 49 |
| PUQU-3-F | 6.0% | | |
| | 7.5% | | |

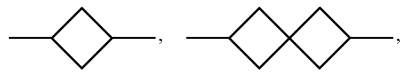

The invention claimed is:

1. A liquid-crystalline medium, comprising one or more compounds of formula I,

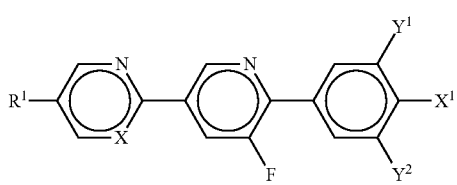

in which

R¹ denotes a halogenated or unsubstituted alkyl or alkoxy radical having 1 to 15 C atoms, in which one or more $CH_2$ groups are optionally replaced, independently of one another, by —C≡C—, —$CF_2$O—, —CH=CH—, —O—, —CO—O— or —O—CO— in such a way that O atoms are not linked directly to one another, X¹ denotes F, Cl, CN, $SF_5$, SCN, NCS, a halogenated alkyl radical, a halogenated alkenyl radical, a halogenated alkoxy radical or a halogenated alkenyloxy radical, each having up to 6 C atoms, X is C—H or N, and Y¹ and Y² each, independently of one another, denote H or F.

2. The liquid-crystalline medium according to claim 1, wherein the one or more compounds of formula I are selected from the compounds of formulae I-1 to I-15,

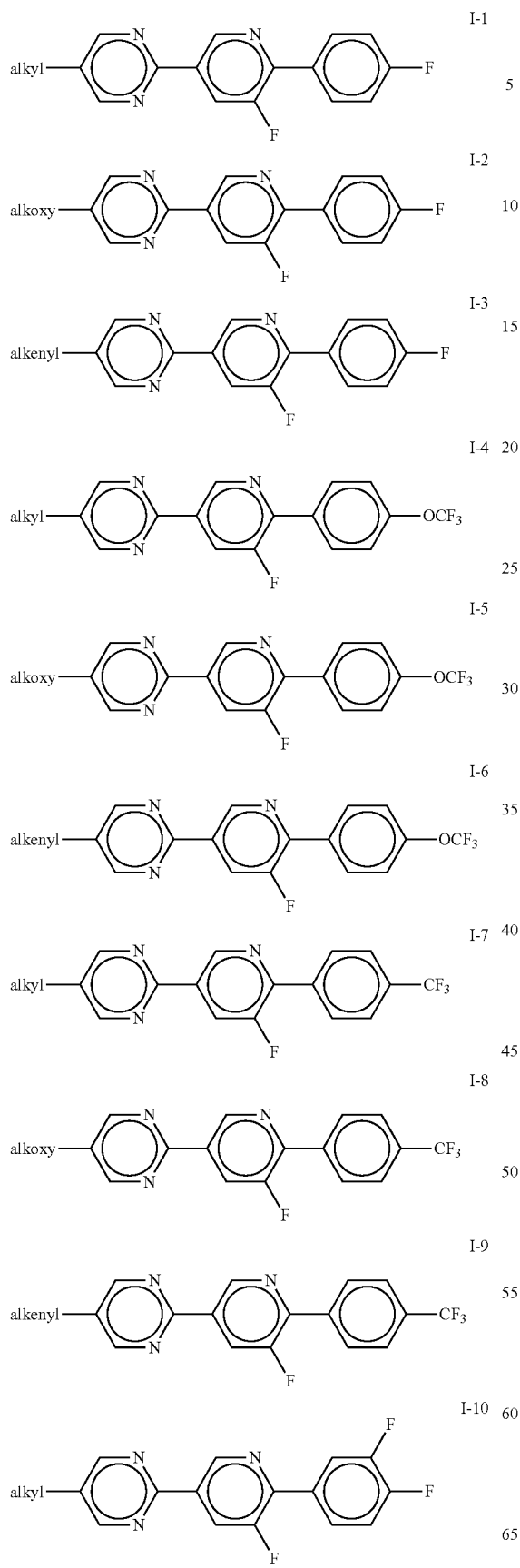
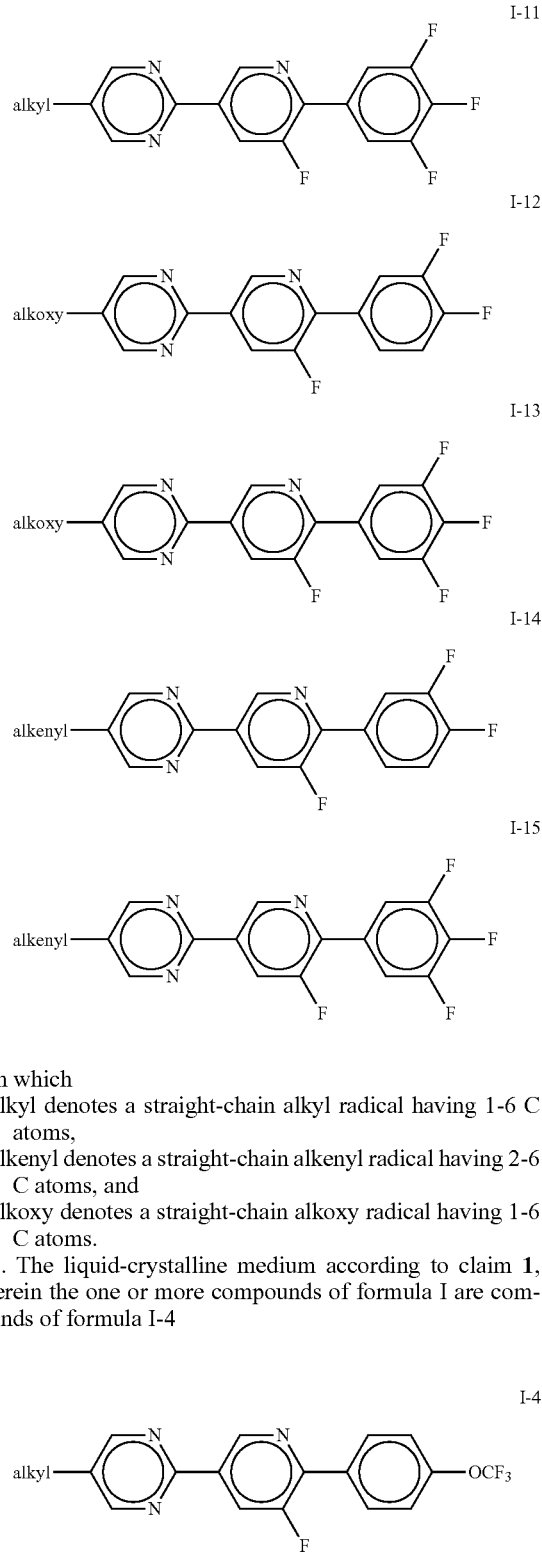

in which
alkyl denotes a straight-chain alkyl radical having 1-6 C atoms,
alkenyl denotes a straight-chain alkenyl radical having 2-6 C atoms, and
alkoxy denotes a straight-chain alkoxy radical having 1-6 C atoms.

3. The liquid-crystalline medium according to claim 1, wherein the one or more compounds of formula I are compounds of formula I-4

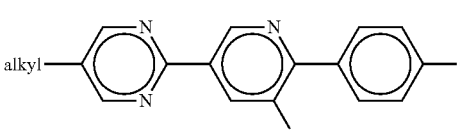

in which
alkyl denotes a straight-chain alkyl radical having 1-6 C atom.

4. The liquid-crystalline medium according to claim 1, which additionally comprises one or more compounds of formulae II and/or III,

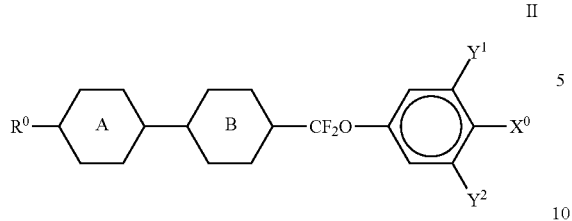

II

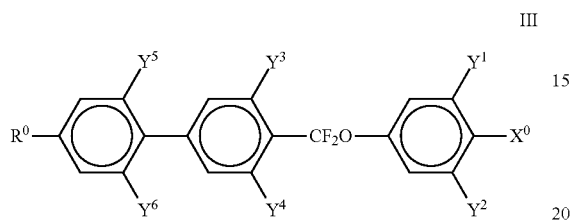

III in which

R⁰ denotes a halogenated or unsubstituted alkyl or alkoxy radical having 1 to 15 C atoms, in which one or more CH$_2$ groups are optionally replaced, independently of one another, by —C≡C—, —CF$_2$O—, —CH=CH—,

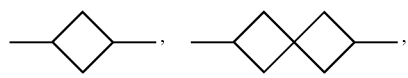

—O—, —CO—O— or —O—CO— in such a way that O atoms are not linked directly to one another, X⁰ denotes F, Cl, CN, SF$_5$, SCN, NCS, a halogenated alkyl radical, a halogenated alkenyl radical, a halogenated alkoxy radical or a halogenated alkenyloxy radical, each having up to 6 C atoms, Y$^{1-6}$ each, independently of one another, denote H or F, and

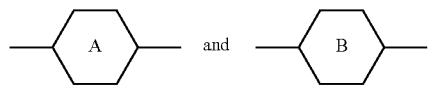

each, independently of one another, denote

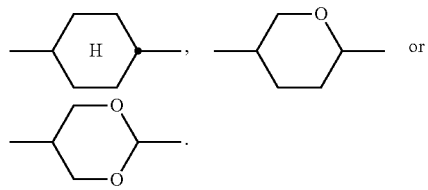

5. The liquid-crystalline medium according to claim 1, which additionally comprises one or more compounds of formulae IV to VIII,

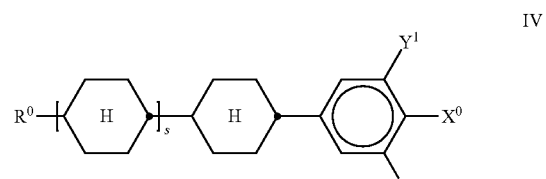

IV

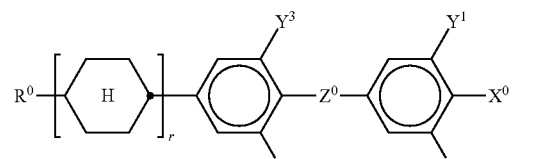

V

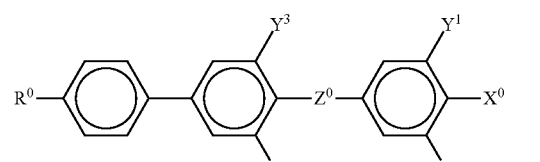

VI

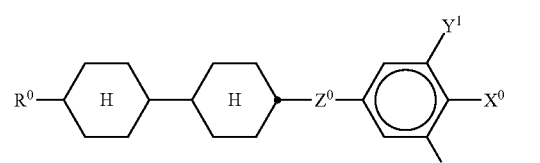

VII

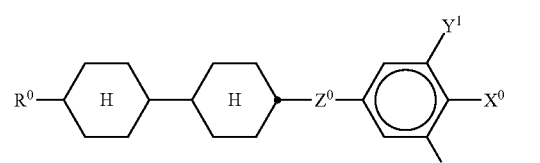

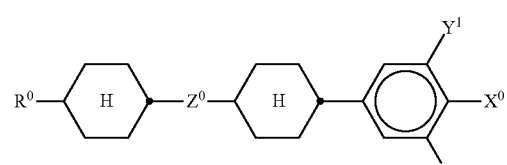

VIII in which

R⁰ denotes a halogenated or unsubstituted alkyl or alkoxy radical having 1 to 15 C atoms, in which one or more CH$_2$ groups are optionally replaced, independently of one another, by —C≡C—, —CF$_2$O—, —CH=CH—,

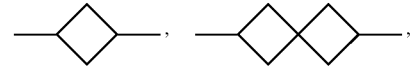

—O—, —CO—O— or —O—CO— in such a way that O atoms are not linked directly to one another, X⁰ denotes F, Cl, CN, SF$_5$, SCN, NCS, a halogenated alkyl radical, a halogenated alkenyl radical, a halogenated alkoxy radical or a halogenated alkenyloxy radical, each having up to 6 C atoms, Y$^{1-4}$ each, independently of one another, denote H or F, Z⁰ denotes —C$_2$H$_4$—, —(CH$_2$)$_4$—, —CH=CH—, —CF=CF—, —C$_2$F$_4$—, —CH$_2$CF$_2$—, —CF$_2$CH$_2$—, —CH$_2$O—, —OCH$_2$—, —COO—, —CF$_2$O— or —OCF$_2$—, in formulae V and VI also a single bond, r denotes 0 or 1, and s denotes 0 or 1.

6. The liquid-crystalline medium according to claim 1, which additionally comprises one or more compounds of formulae IX to XII,

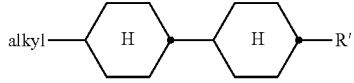
IX

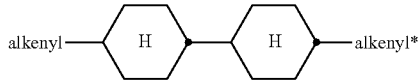
X

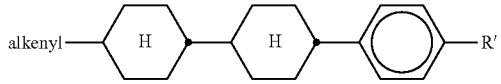
XI

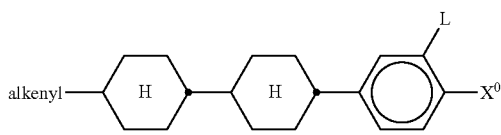
XII

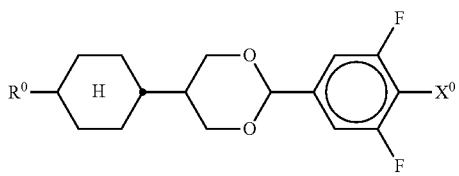
XXVII

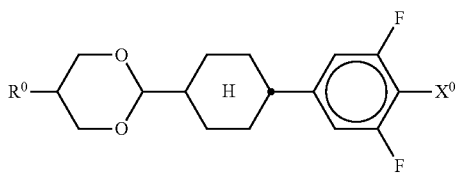
XXVIII

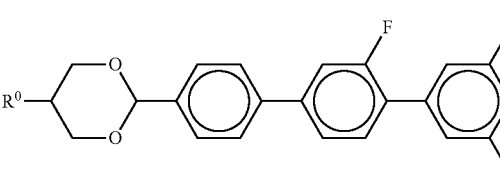
XXIX in which
$X^0$ denotes F, Cl, CN, $SF_5$, SCN, NCS, a halogenated alkyl radical, a halogenated alkenyl radical, a halogenated alkoxy radical or a halogenated alkenyloxy radical, each having up to 6 C atoms,
L denotes H or F,
"alkyl" denotes $C_{1-6}$-alkyl,
R' denotes $C_{1-6}$-alkyl, $C_{1-6}$-alkoxy or $C_{2-6}$-alkenyl, and
"alkenyl" and "alkenyl*" each, independently of one another, denote $C_{2-6}$-alkenyl.

7. The liquid-crystalline medium according to claim 1, which additionally comprises one or more compounds of formula XIII,

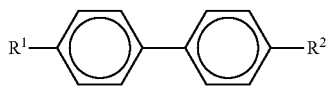
XIII in which $R^1$ and $R^2$ each, independently of one another, denote n-alkyl, alkoxy, oxaalkyl, fluoroalkyl or alkenyl, each having up to 6 C atoms.

8. The liquid-crystalline medium according to claim 1, which additionally comprises one or more compounds of formula XVII,

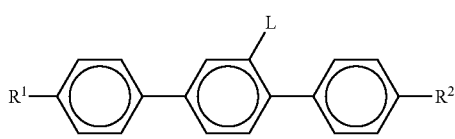
XVII in which $R^1$ and $R^2$ each, independently of one another, denote n-alkyl, alkoxy, oxaalkyl, fluoroalkyl or alkenyl, each having up to 8 C atoms, and L denotes H or F.

9. The liquid-crystalline medium according to claim 1, which additionally comprises one or more compounds of formulae XXVII, XXVIII and/or XXIX, in which
$R^0$ denotes a halogenated or unsubstituted alkyl or alkoxy radical having 1 to 15 C atoms, in which one or more $CH_2$ groups are optionally replaced, independently of one another, by —C≡C—, —$CF_2$O—, —CH=CH—,

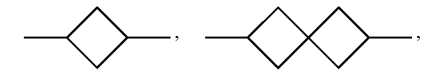

—O—, —CO—O— or —O—CO— in such a way that O atoms are not linked directly to one another, and
$X^0$ denotes F, Cl, CN, $SF_5$, SCN, NCS, a halogenated alkyl radical, a halogenated alkenyl radical, a halogenated alkoxy radical or a halogenated alkenyloxy radical, each having up to 6 C atoms.

10. The liquid-crystalline medium according to claim 1, which additionally comprises one or more compounds of formulae XIX, XX, XXI, XXII, XXIII and/or XXIV,

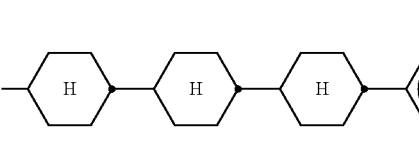
XIX

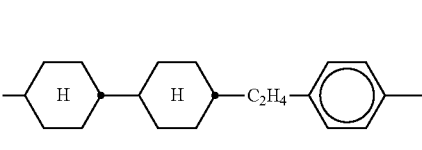
XX

-continued

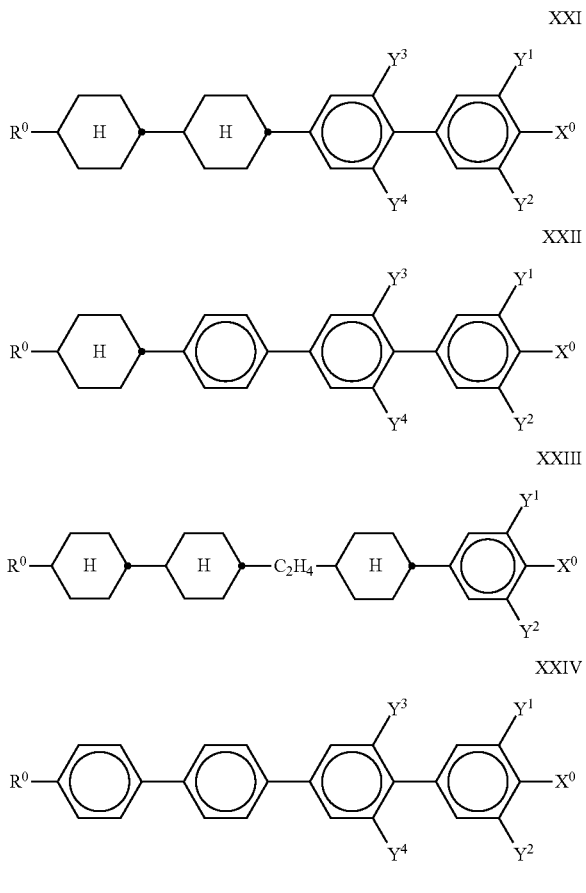

in which
R⁰ denotes a halogenated or unsubstituted alkyl or alkoxy radical having 1 to 15 C atoms, in which one or more CH₂ groups are optionally replaced, independently of one another, by —C≡C—, —CF₂O—, —CH=CH—,

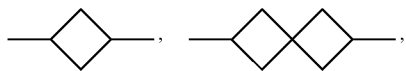

—O—, —CO—O— or —O—CO— in such a way that O atoms are not linked directly to one another,
X⁰ denotes F, Cl, CN, SF₅, SCN, NCS, a halogenated alkyl radical, a halogenated alkenyl radical, a halogenated alkoxy radical or a halogenated alkenyloxy radical, each having up to 6 C atoms, and
Y¹⁻⁴ each, independently of one another, denote H or F.

11. The liquid-crystalline medium according to claim 1, which additionally it comprises ≥20% by weight of the compound of the formula IXb,

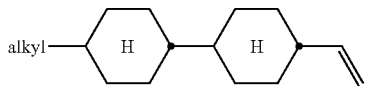

in which alkyl denotes $C_{1-6}$-alkyl.

12. The liquid-crystalline medium according to claim 1, which additionally comprises one or more additives selected from the group consisting of UV stabilisers, dopants and antioxidants.

13. The liquid-crystalline medium according to claim 1, which additionally comprises one or more polymerisable compounds.

14. A process for preparing the liquid-crystalline medium according to claim 1, comprising mixing together one or more compounds of formula I with further liquid-crystalline compounds and optionally also with one or more additives and/or at least one polymerisable compound.

15. An electro-optical application, comprising a medium according to claim 1.

16. A product selected from the group consisting of shutter glasses, 3D applications, TN, PS-TN, STN, TN-TFT, OCB, IPS, PS-IPS, FFS, PS-FFS and PS-VA-IPS displays, comprising a medium according to claim 1.

17. An electro-optical liquid-crystal display containing a liquid-crystalline medium according to claim 1.

18. A compound of formula I

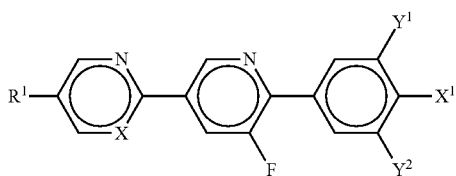

in which
R¹ denotes a halogenated or unsubstituted alkyl or alkoxy radical having 1 to 15 C atoms, in which one or more CH₂ groups are optionally replaced, independently of one another, by —C≡C—, —CF₂O—, —CH=CH—,

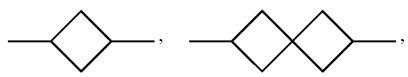

—O—, —CO—O— or —O—CO— in such a way that O atoms are not linked directly to one another,
X¹ denotes F, Cl, CN, SF₅, SCN, NCS, a halogenated alkyl radical, a halogenated alkenyl radical, a halogenated alkoxy radical or a halogenated alkenyloxy radical, each having up to 6 C atoms,
X denotes C—H or N, and
Y¹ and Y² each, independently of one another, denote H or F.

* * * * *